US010000752B2

(12) United States Patent
Collard et al.

(10) Patent No.: US 10,000,752 B2
(45) Date of Patent: *Jun. 19, 2018

(54) ANTAGONAT COMPOSITIONS AND METHODS OF USE

(75) Inventors: Joseph Collard, Delray Beach, FL (US); Olga Khorkova Sherman, Tequesta, FL (US); Belinda De Leon, San Francisco, CA (US)

(73) Assignee: CuRNA, Inc., Miami, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/988,063

(22) PCT Filed: Nov. 17, 2011

(86) PCT No.: PCT/US2011/061137

§ 371 (c)(1),
(2), (4) Date: May 17, 2013

(87) PCT Pub. No.: WO2012/068340

PCT Pub. Date: May 24, 2012

(65) Prior Publication Data

US 2013/0245099 A1 Sep. 19, 2013

Related U.S. Application Data

(60) Provisional application No. 61/415,307, filed on Nov. 18, 2010, provisional application No. 61/415,858, filed on Nov. 21, 2010.

(51) Int. Cl.

| | |
|---|---|
| ***C12N 15/11*** | (2006.01) |
| ***C12N 15/113*** | (2010.01) |
| ***A61K 31/00*** | (2006.01) |
| ***A61K 31/7088*** | (2006.01) |
| ***A61K 31/7115*** | (2006.01) |

(52) U.S. Cl.

CPC ............ *C12N 15/113* (2013.01); *A61K 31/00* (2013.01); *A61K 31/7088* (2013.01); *A61K 31/7115* (2013.01); *C12N 15/111* (2013.01); *C12N 2310/113* (2013.01); *C12N 2310/3231* (2013.01); *C12N 2310/3341* (2013.01); *C12N 2310/344* (2013.01)

(58) Field of Classification Search

CPC ............ C12N 15/113; C12N 2310/321; C12N 2310/11; C12N 2310/113; C12N 2310/14; C12N 2310/3525

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,754,065 | A | 6/1988 | Levenson et al. |
| 4,800,159 | A | 1/1989 | Mullis et al. |
| 5,034,506 | A | 7/1991 | Summerton et al. |
| 5,138,045 | A | 8/1992 | Cook et al. |
| 5,218,105 | A | 6/1993 | Cook et al. |
| 5,288,512 | A | 2/1994 | Seiden |
| 5,288,514 | A | 2/1994 | Ellman |
| 5,319,080 | A | 6/1994 | Leumann |
| 5,393,878 | A | 2/1995 | Leumann |
| 5,432,272 | A | 7/1995 | Benner et al. |
| 5,457,189 | A | 10/1995 | Crooke et al. |
| 5,459,255 | A | 10/1995 | Cook et al. |
| 5,474,796 | A | 12/1995 | Brennan |
| 5,491,084 | A | 2/1996 | Chalfie et al. |
| 5,506,337 | A | 4/1996 | Summerton et al. |
| 5,519,134 | A | 5/1996 | Acevedo et al. |
| 5,525,735 | A | 6/1996 | Gallop et al. |
| 5,539,083 | A | 7/1996 | Cook et al. |
| 5,549,974 | A | 8/1996 | Holmes |
| 5,569,588 | A | 10/1996 | Ashby et al. |
| 5,576,302 | A | 11/1996 | Cook et al. |
| 5,593,853 | A | 1/1997 | Chen et al. |
| 5,605,662 | A | 2/1997 | Heller et al. |
| 5,661,134 | A | 8/1997 | Cook et al. |
| 5,708,161 | A | 1/1998 | Reese |
| 5,739,119 | A | 4/1998 | Galli et al. |
| 5,739,311 | A | 4/1998 | Lackey et al. |
| 5,756,710 | A | 5/1998 | Stein et al. |
| 5,849,902 | A | 12/1998 | Arrow et al. |
| 5,891,725 | A | 4/1999 | Soreq et al. |
| 5,902,880 | A | 5/1999 | Thompson |
| 5,908,779 | A | 6/1999 | Carmichael et al. |
| 5,965,721 | A | 10/1999 | Cook et al. |
| 5,985,663 | A | 11/1999 | Bennett et al. |
| 6,005,095 | A | 12/1999 | Capaccioli et al. |
| 6,013,639 | A | 1/2000 | Peyman et al. |
| 6,013,786 | A | 1/2000 | Chen et al. |
| 6,034,233 | A | 3/2000 | Ecker et al. |

(Continued)

FOREIGN PATENT DOCUMENTS

| | | |
|---|---|---|
| CA | 2686933 | 4/2008 |
| EP | 335451 A3 | 3/1988 |

(Continued)

OTHER PUBLICATIONS

Jepsen et al, LNA-Antisense rivals siRNA for gene silencing, 2004, Current Opinion in Drug Discovery and Development, 2004, 7(2): 188-194.*

(Continued)

*Primary Examiner* — Ekaterina Poliakova-Georgantas

(74) *Attorney, Agent, or Firm* — CuRNA, Inc.; Monte R. Browder

(57) ABSTRACT

Provided herein are compositions, compounds, and methods of modulating gene expression. In certain embodiments described herein is a composition, wherein the composition comprises an antagoNAT. In some embodiments, the antagoNAT is an oligonucleotide comprising modified and unmodified sugar subunits, wherein the antagoNAT hybridizes with a natural antisense transcript. Certain embodiments of the present invention provide a method for modulating gene expression in a cell comprising contacting the cell with an antagoNAT. In some embodiments, the method includes forming a hybrid comprising the antagoNAT and a natural antisense transcript of the gene, wherein the hybrid sterically blocks the normal function of the natural antisense transcript.

27 Claims, 10 Drawing Sheets

(56) References Cited

U.S. PATENT DOCUMENTS 6,100,090 A 8/2000 Monia et al.
6,140,492 A 10/2000 Morelli et al.
6,147,200 A 11/2000 Manoharan et al.
6,165,712 A 12/2000 Foulkes et al.
6,165,990 A 12/2000 Singh et al.
6,175,409 B1 1/2001 Nielsen et al.
6,221,587 B1 4/2001 Ecker et al.
6,239,265 B1 5/2001 Cook
6,242,589 B1 6/2001 Cook et al.
6,268,490 B1 7/2001 Imanishi et al.
6,303,374 B1 10/2001 Zhang et al.
6,307,040 B1 10/2001 Cook et al.
6,316,198 B1 11/2001 Skouv et al.
6,335,434 B1 1/2002 Guzaev et al.
6,376,541 B1 4/2002 Nixon et al.
6,403,566 B1 6/2002 Wang
6,444,464 B1 9/2002 Wyatt
6,451,991 B1 9/2002 Martin et al.
6,525,191 B1 2/2003 Ramassamy
6,528,262 B1 3/2003 Gilad et al.
6,528,631 B1 3/2003 Cook et al.
6,617,122 B1 9/2003 Hayden et al.
6,617,442 B1 9/2003 Crooke et al.
6,630,315 B1 10/2003 Miwa et al.
6,639,059 B1 10/2003 Kochkine et al.
6,656,730 B1 12/2003 Manoharan
6,667,337 B2 12/2003 Wilson
6,670,461 B1 12/2003 Wengel et al.
6,710,174 B2 3/2004 Bennett et al.
6,734,291 B2 5/2004 Kochkine et al.
6,762,169 B1 7/2004 Manoharan
6,794,499 B2 9/2004 Wengel et al.
6,833,361 B2 12/2004 Hong et al.
6,861,514 B2 3/2005 Cook et al.
6,867,294 B1 3/2005 Sanghvi et al.
6,936,467 B2 8/2005 Kmiec et al.
6,936,593 B1 8/2005 Agrawal et al.
6,977,295 B2 12/2005 Belotserkovskii et al.
6,986,988 B2 1/2006 Gilad et al.
7,034,133 B2 4/2006 Wengel et al.
7,034,145 B2 5/2006 Shen et al.
7,053,195 B1 5/2006 Goff
7,053,199 B2 5/2006 Imanishi et al.
7,053,207 B2 5/2006 Wengel
7,060,580 B2 6/2006 Wengel et al.
7,084,125 B2 8/2006 Wengel
7,087,589 B2 8/2006 Jacobson et al.
7,125,982 B1 10/2006 Frayne
7,144,995 B2 12/2006 Wise et al.
7,144,999 B2 12/2006 Ward et al.
7,148,204 B2 12/2006 Bennett et al.
7,153,954 B2 12/2006 Koch et al.
7,169,916 B2 1/2007 Krotz et al.
7,199,107 B2 4/2007 Dobie et al.
7,202,357 B2 4/2007 Crooke et al.
7,217,572 B2 5/2007 Ward et al.
7,220,549 B2 5/2007 Buzby
7,226,785 B2 6/2007 Kmiec et al.
7,229,974 B2 6/2007 Peyman et al.
7,229,976 B2 6/2007 Dobie et al.
7,235,534 B2 6/2007 Tauguay et al.
7,235,653 B2 6/2007 Bennett et al.
7,238,858 B2 7/2007 Marraccini et al.
7,276,599 B2 10/2007 Moore et al.
7,285,288 B1 10/2007 Tormo et al.
7,297,786 B2 11/2007 McCray et al.
7,314,923 B2 1/2008 Kaneko et al.
7,320,965 B2 1/2008 Sah et al.
7,321,828 B2 1/2008 Cowsert et al.
7,335,764 B2 2/2008 Crooke et al.
7,335,765 B2 2/2008 Kaneko et al.
7,339,051 B2 3/2008 Crooke et al.
7,371,583 B2 5/2008 Weiss
7,399,845 B2 7/2008 Seth et al.
7,402,434 B2 7/2008 Newman et al.
7,402,574 B2 7/2008 Iversen et al.
7,420,050 B2 9/2008 Park et al.
7,423,142 B2 9/2008 Vornlocher
7,425,545 B2 9/2008 Crooke et al.
7,427,675 B2 9/2008 Capaldi et al.
7,456,154 B2 11/2008 Soreq et al.
7,462,642 B2 12/2008 Wang et al.
7,468,431 B2 12/2008 Bhanot et al.
7,510,830 B2 3/2009 Baguley et al.
7,541,344 B2 6/2009 Bhat et al.
7,547,684 B2 6/2009 Seth et al.
7,569,575 B2 8/2009 Sorensen et al.
7,569,686 B1 8/2009 Bhat et al.
7,572,582 B2 8/2009 Wengel et al.
7,582,745 B2 9/2009 Sah et al.
7,585,893 B2 9/2009 Baguley et al.
7,589,190 B2 9/2009 Westergaard et al.
7,598,227 B2 10/2009 Crooke et al.
7,605,251 B2 10/2009 Tan et al.
7,622,453 B2 11/2009 Frieden et al.
7,662,948 B2 2/2010 Kurreck et al.
7,666,854 B2 2/2010 Seth et al.
7,674,895 B2 3/2010 Reich et al.
7,687,617 B2 3/2010 Thrue et al.
7,691,995 B2 4/2010 Zamore et al.
7,695,902 B2 4/2010 Crooke
7,696,345 B2 4/2010 Allerson et al.
7,709,456 B2 5/2010 Corey et al.
7,709,630 B2 5/2010 Gaarde et al.
7,713,738 B2 5/2010 Hansen et al.
7,718,629 B2 5/2010 Bamcrot et al.
7,723,508 B2 5/2010 Crooke et al.
7,732,422 B2 6/2010 Gleave et al.
7,732,590 B2 6/2010 Bhanot et al.
7,737,264 B2 6/2010 Thrue et al.
7,737,265 B2 6/2010 Akinc et al.
7,741,305 B2 6/2010 Crooke et al.
7,741,309 B2 6/2010 Hansen et al.
7,741,457 B2 6/2010 Seth et al.
7,745,609 B2 6/2010 Bennett et al.
7,749,978 B2 7/2010 Sah et al.
2003/0139359 A1 7/2003 Dobie
2003/0186920 A1 10/2003 Sirois
2003/0191075 A1 10/2003 Cook et al.
2003/0228618 A1 12/2003 Levanon et al.
2003/0233670 A1 12/2003 Edgerton et al.
2004/0006031 A1 1/2004 Dean et al.
2004/0033480 A1 2/2004 Wong
2004/0101858 A1 5/2004 Ward et al.
2004/0137423 A1 7/2004 Hayden et al.
2004/0138155 A1 7/2004 Baird et al.
2004/0175803 A1 9/2004 Meritet et al.
2004/0180336 A1 9/2004 Gilad et al.
2004/0254137 A1 12/2004 Ackermann et al.
2005/0009771 A1 1/2005 Levanon et al.
2005/0026160 A1 2/2005 Allerson et al.
2005/0113326 A1 5/2005 Siwkowski et al.
2005/0143357 A1 6/2005 Pousette et al.
2005/0153286 A1 7/2005 Clements
2005/0215504 A1 9/2005 Bennett et al.
2005/0222029 A1 10/2005 Bartel et al.
2006/0009410 A1 1/2006 Crooke et al.
2006/0142196 A1 6/2006 Klein et al.
2006/0178333 A1 8/2006 Soreq et al.
2007/0082848 A1 4/2007 Alitalo et al.
2007/0197459 A1 8/2007 Milner
2007/0213274 A1 9/2007 Salonen
2007/0213292 A1 9/2007 Stoffel et al.
2007/0231816 A1 10/2007 Chaussabel et al.
2007/0248590 A1 10/2007 Milne et al.
2008/0146788 A1 6/2008 Bhat et al.
2008/0221051 A1 9/2008 Becker et al.
2008/0293142 A1 11/2008 Liu et al.
2009/0092988 A1* 4/2009 Schwartz .............. C12N 15/111
435/6.16
2009/0191263 A1 7/2009 Reich et al.
2009/0192106 A1 7/2009 Dobie et al.
2009/0208479 A1 8/2009 Jaye et al.
2009/0258925 A1 10/2009 Wahlestedt

(56) References Cited

U.S. PATENT DOCUMENTS

| | | | |
|---|---|---|---|
| 2009/0318536 | A1 | 12/2009 | Freier et al. |
| 2009/0326041 | A1 | 12/2009 | Bhanot et al. |
| 2010/0105760 | A1 | 4/2010 | Collard et al. |

FOREIGN PATENT DOCUMENTS

| | | | | |
|---|---|---|---|---|
| EP | 335451 | A2 | | 10/1989 |
| WO | WO-1984/03564 | | | 9/1984 |
| WO | WO-1991/19735 | | | 12/1991 |
| WO | WO 1992/00091 | | | 1/1992 |
| WO | WO-1992/08796 | | | 5/1992 |
| WO | WO 1993/20242 | | | 10/1993 |
| WO | WO-1994-026887 | A1 | | 11/1994 |
| WO | WO-1994/28143 | | | 12/1994 |
| WO | WO-1995-015373 | A2 | | 6/1995 |
| WO | WO-1995/22618 | | | 8/1995 |
| WO | WO-1995/25116 | | | 10/1995 |
| WO | WO-1995/35505 | | | 12/1995 |
| WO | WO-1996-027663 | A2 | | 9/1996 |
| WO | WO-1997-039120 | A1 | | 10/1997 |
| WO | WO-1999-014226 | A1 | | 3/1999 |
| WO | WO-1999-039352 | A1 | | 8/1999 |
| WO | WO 2000-057837 | A1 | | 10/2000 |
| WO | WO 2000-061770 | A2 | | 10/2000 |
| WO | WO-2001-000669 | A2 | | 1/2001 |
| WO | WO 2001-21631 | A2 | | 3/2001 |
| WO | WO-2001-025488 | A2 | | 4/2001 |
| WO | WO-2001-051630 | A1 | | 7/2001 |
| WO | WO 2002-062840 | A1 | | 8/2002 |
| WO | WO-2002-068688 | A1 | | 9/2002 |
| WO | WO-2004-016255 | A1 | | 2/2004 |
| WO | WO-2004-024079 | A2 | | 3/2004 |
| WO | WO-2004-030750 | A1 | | 4/2004 |
| WO | WO 2004-041838 | A1 | | 5/2004 |
| WO | WO 2004-104161 | A2 | | 12/2004 |
| WO | WO-2005-045034 | A2 | | 5/2005 |
| WO | WO-2005-070136 | A2 | | 8/2005 |
| WO | WO-2005-079862 | A1 | | 9/2005 |
| WO | WO-2007-028065 | A2 | | 3/2007 |
| WO | WO-2007-071182 | A1 | | 6/2007 |
| WO | WO-2007-087113 | A2 | | 8/2007 |
| WO | WO-2007-138023 | A1 | | 12/2007 |
| WO | WO-2008-057556 | A2 | | 5/2008 |
| WO | WO 2008-066672 | A2 | | 6/2008 |
| WO | WO-2008-087561 | A2 | | 7/2008 |
| WO | WO 2009124295 | A2 | * | 10/2009 |
| WO | WO-2010-002984 | A1 | | 1/2010 |
| WO | WO-2010-040571 | A2 | | 4/2010 |
| WO | WO 2010040112 | A2 | * | 4/2010 |
| WO | WO-2010-054364 | A1 | | 5/2010 |
| WO | WO-2010-058227 | A2 | | 5/2010 |

OTHER PUBLICATIONS

Mahmoudi et al, Wrap53, a Natural p53 Antisense Transcript Required for p53 Induction upon DNA Damage, 2009, Molecular Cell, 33: 462-471.*

GenBank NM_010272.2, Mus musculus growth differentiation factor 11 mRNA, 2017, p. 1-5.*

Beletskii et al, PNA interference mapping demonstrates functional domains in the noncoding RNA Xist, 2001, PNAS, vol. 98, 16: 9215-9220.*

International Search Report corresponding to PCT/US2011/061137 dated May 22, 2012. (May 22, 2012).

Ausubel, Current Protocols in Molecular Biology vol. 1, 1994, 6.0.1-6.4.10.

Barak, et al., "A β-Arrestin/Green Fluorescent Protein Biosensor for Detecting G Protein-Coupled Receptor Activation," J. Biol. Chem. 272:27497-27500 (1997).

Barber, et al., "Delivery of membrane-impermeant fluorescent probes into living neural cell populations by lipotransfer," Neuroscience Letters 207:17-20 (1996).

Baum, "Solid-phase synthesis of benzodiazepines," C&EN News, Jan. 18, p. 33-34 (1993).

Bernstein, E., et al., "Role for a Bidentate Ribonuclease in the Initiation Step of RNA Interference," Nature 409:363-366 (2001).

Boutla, A., et al., "Short 5'-phosphorylated double-stranded RNAs induce RNA interference in *Drosophila*," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biology vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480:2-16 (2000).

Chabala, J.C., "Solid-phase combinatorial chemistry and novel tagging methods for identifying leads," Curr Opin Biotechnol. 6:632-639 (1995).

Cech, J., "Ribozymes and Their Medical Implications," American. Med Assoc. 260:3030-3035 (1988).

Chen, et al., "Expression of ssDNA in Mammalian Cells," BioTechniques 34:167-171 (2003).

Chen, et al., "Analogous Organic Synthesis of Small-Compound Libraries: Validation of Combinatorial Chemistry in Small-Molecule Synthesis," J. Amer. Chem. Soc. 116:2661-2662 (1994).

Cheng, J. et al., "Transcriptional maps of 10 human chromosomes at 5-nucleotide resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).

Cubitt et al., "Understanding, improving and using green fluorescent proteins," Trends in Biochemical Science 20:448-455 (1995).

Curiel, D. T. et al., "Adenovirus enhancement of transferrin-polylysine-mediated gene delivery," PNAS 88:8850-8854 (1991).

Dai et al., "SIRT1 Interacts With p73 and Suppresses p73-Dependent Transcriptional Activity," J Cell Physiol 210(1):161-165 (2007).

Davidson, et al., "A model system for in vivo gene transfer into the central nervous system using an adenoviral vector," Nat. Genet 3:219-223 (1993).

Davis, et al., "Direct Gene Transfer into Skeletal Muscle In Vivo: Factors Affecting Efficiency of Transfer and Stability of Expression," Hum Gene Ther 4:151-159 (1993).

De Mesmaeker, et al., "Antisense Oligonucleotides," Acc. Chem. Res. 28:366-374 (1995).

Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).

(56) References Cited

OTHER PUBLICATIONS

Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human β-Globin Alleles Differing by a Single Nucleotide Polymorphism," RNAS, vol. 103, No. 15, pp. 5953-5958, (2006).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type I vector," PNAS U.S.A. :90:7603-7607 (1993).
Geller, A.I., et al., "Infection of cultured central nervous system neurons with a defective herpes simplex virus I vector results in stable expression of *Escherichia coli* β-galactosidase," PNAS USA 87:1149-1153 (1990).
GenBank Accession No. NM_000559, *Homo sapiens* Hemoglobin, Gamma A (HBG1), mRNA, (2008).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and analysis of inflammatory disease-related genes using cDNA microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem., Soc., 114:9217-9218 (1992).
Hobbs-DeWitt, et al., "Diversomers: An approach to nonpeptide, nonoligomeric chemical diversity," Proc. Nat. Acad. Sci. USA 90:6909-6913 (1993).
Houghton AN, Gold JS, Blachere NE, Immunity against cancer: lessons learned front melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, 1980 pp. 75-77.
Larson, et al., "Rapid DNA Fingerprinting of Pathogens by Flow Cytometry," Cytometry, 2000, 41:203-208 (2000).
Larsson, et al., "High-throughput protein expression of cDNA products as a tool in functional genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, properties, and activity as inhibitors of replication of human immunodeficiency virus in cell culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).

(56) References Cited

OTHER PUBLICATIONS

Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense *bcl-2-IgH* transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Siuod, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genuine analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents—Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of SirtI by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamagno, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, KY, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).

(56) References Cited

OTHER PUBLICATIONS

Wahlestedt, C., "Antisense oligonucleotide strategies in neuropharmacology," Trends Pharmacol Sci 15:2:42-46 (1994).
Walsh, et al., "The role of cell-derived oligomers of Aβ in Alzheimer's disease and avenues for therapeutic intervention," Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Antisense (NOS3AS) Gene Encodes an Autophagy-Related Protein (APG9-like2) Highly Expressed in Trophoblast" (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; 1-10 (2012).
EP Application No. 06850393.7 Examination Report dated Oct. 18, 2011.
International Search Report and Written Opinion for PCT Application No. PCT/US2010/033078 dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
PCT/US96/10287 (WO97/000271) The Regents of the University of California Jan. 3, 1997.

* cited by examiner

FIG. 1
(SEQ ID NO: 40)

SEQ ID NO: 40

CAAAATGGCGTGCTACCCTGTCCAACCTTGTCTGTAGACAGAGTCAATTGAACACTGTCTTTGGA
CTTCCGTGCAACTGAGGTGGGCGGGCTTGAAGCACAAAGCTTTCAGGGAGAACCAAACTTTATGC
CCAAGCTGCTCTCTGCCACCCACAGGGTAAAtGAATCTCATACAGGAAAGGCAaGAGACATGTGAC
ACTGTTGTTCTGaTGGTCACAAGTCAAGCTTTTTAAAAAGCAGCCTGATATTGTGAGCTAACATGGC
TTTCTGTAATTGAATGCAATGTATTTTCTATGCTTGTCTGGGTAAAGTTGACCTTGGTTTGATTTAG
CTCAAGCAATATTTCAACAGTGCACTGGGGCtctgccccctgactACTGTTTGaCTAGAGCCAGGCTCTGCC
CTGGATGGCAACCAACAGCCCAGGCTCTGGGGCACAGCCGGGCTTTGACAGGTCTGGGGAAATGT
TCAccGGAGATGAAAGGTTTCAAACTATgAAACTCTAAAATCTCAAGTCAAAACTTTTGACAAGCA
CACACAGGACATGAATTACAATCACCCGAAGATTTTTACAGGCTTCTCAaTTTTAATGACATGCTG
ACACGtGTCATCAGATCTCACAACAAGATGACACATGGGTGTCAGGTATGgcgCAGAAGACTAGAG
TCGGGGTGTAA

FIG. 2

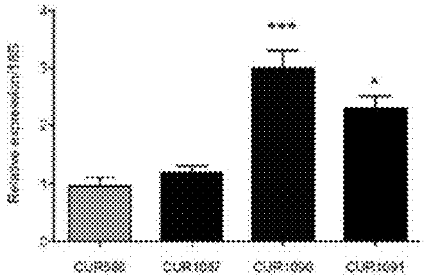

FIG. 3a

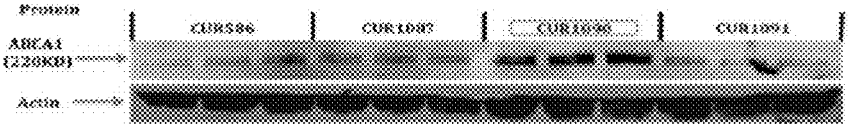

FIG. 3b

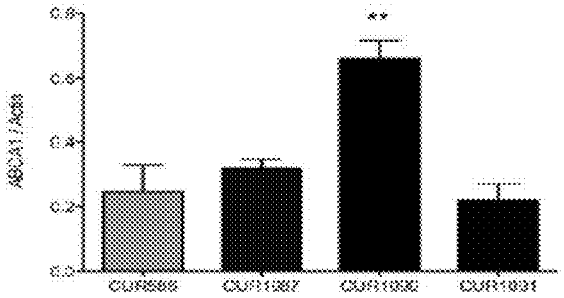

SEQUENCE LISTING

<160> NUMBER OF SEQ ID NOS: 40

<210> SEQ ID NO 1
<211> LENGTH: 10515
<212> TYPE: DNA
<213> ORGANISM: Homo sapiens

<400> SEQUENCE: 1

```
ggaggaggga gagcacaggc tttgaccgat agtaacctct gcgctcggtg cagccgaatc     60
tataaaagga actagtcccg gcaaaaaccc cgtaattgcg agcgagagtg agtggggccg    120
ggacccgcag agccgagccg acccttctct cccgggctgc ggcagggcag ggcggggagc    180
tccgcgcacc aacagagccg gttctcaggg cgctttgctc cttgtttttt ccccggttct    240
gttttctccc cttctccgga aggcttgtca aggggtagga gaaagagacg caaacacaaa    300
agtggaaaac agttaatgac cagccacggc gtccctgctg tgagctctgg ccgctgcctt    360
ccagggctcc cgagccacac gctgggggtg ctggctgagg gaacatggct tgttggcctc    420
agctgaggtt gctgctgtgg aagaacctca ctttcagaag aagacaaaca tgtcagctgc    480
tgctggaagt ggcctggcct ctatttatct tcctgatcct gatctctgtt cggctgagct    540
acccacccta tgaacaacat gaatgccatt ttccaaataa agccatgccc tctgcaggaa    600
cacttccttg ggttcagggg attatctgta atgccaacaa cccctgtttc cgttacccga    660
ctcctgggga ggctcccgga gttgttggaa actttaacaa atccattgtg gctcgcctgt    720
tctcagatgc tcggaggctt cttttataca gccagaaaga caccagcatg aaggacatgc    780
gcaaagttct gagaacatta cagcagatca agaaatccag ctcaaacttg aagcttcaag    840
atttcctggt ggacaatgaa accttctctg ggttcctgta tcacaacctc tctctcccaa    900
agtctactgt ggacaagatg ctgagggctg atgtcattct ccacaaggta tttttgcaag    960
gctaccagtt acatttgaca agtctgtgca atggatcaaa atcagaagag atgattcaac   1020
ttggtgacca agaagtttct gagctttgtg gcctaccaag ggagaaactg gctgcagcag   1080
agcgagtact tcgttccaac atggacatcc tgaagccaat cctgagaaca ctaaactcta   1140
catctccctt cccgagcaag gagctggctg aagccacaaa aacattgctg catagtcttg   1200
ggactctggc ccaggagctg ttcagcatga gaagctggag tgacatgcga caggaggtga   1260
tgtttctgac caatgtgaac agctccagct cctccaccca aatctaccag gctgtgtctc   1320
gtattgtctg cgggcatccc gagggagggg ggctgaagat caagtctctc aactggtatg   1380
aggacaacaa ctacaaagcc ctctttggag gcaatggcac tgaggaagat gctgaaacct   1440
tctatgacaa ctctacaact ccttactgca atgatttgat gaagaatttg gagtctagtc   1500
ctctttcccg cattatctgg aaagctctga agccgctgct cgttgggaag atcctgtata   1560
cacctgacac tccagccaca aggcaggtca tggctgaggt gaacaagacc ttccaggaac   1620
tggctgtgtt ccatgatctg gaaggcatgt gggaggaact cagccccaag atctggacct   1680
tcatggagaa cagccaagaa atggaccttg tccggatgct gttggacagc agggacaatg   1740
accacttttg ggaacagcag ttggatggct tagattggac agcccaagac atcgtggcgt   1800
ttttggccaa gcacccagag gatgtccagt ccagtaatgg ttctgtgtac acctggagag   1860
aagctttcaa cgagactaac caggcaatcc ggaccatatc tcgcttcatg gagtgtgtca   1920
acctgaacaa gctagaaccc atagcaacag aagtctggct catcaacaag tccatggagc   1980
tgctggatga gaggaagttc tgggctggta ttgtgttcac tggaattact ccaggcagca   2040
ttgagctgcc ccatcatgtc aagtacaaga tccgaatgga cattgacaat gtggagagga   2100
```

-continued

```
caaataaaat caaggatggg tactgggacc ctggtcctcg agctgacccc tttgaggaca   2160
tgcggtacgt ctgggggggc ttcgcctact tgcaggatgt ggtggagcag gcaatcatca   2220
gggtgctgac gggcaccgag aagaaaactg gtgtctatat gcaacagatg ccctatccct   2280
gttacgttga tgacatcttt ctgcgggtga tgagccggtc aatgcccctc ttcatgacgc   2340
tggcctggat ttactcagtg gctgtgatca tcaagggcat cgtgtatgag aaggaggcac   2400
ggctgaaaga gaccatgcgg atcatgggcc tggacaacag catcctctgg tttagctggt   2460
tcattagtag cctcattcct cttcttgtga gcgctggcct gctagtggtc atcctgaagt   2520
taggaaacct gctgccctac agtgatccca gcgtggtgtt tgtcttcctg tccgtgtttg   2580
ctgtggtgac aatcctgcag tgcttcctga ttagcacact cttctccaga gccaacctgg   2640
cagcagcctg tgggggcatc atctacttca cgctgtacct gccctacgtc ctgtgtgtgg   2700
catggcagga ctacgtgggc ttcacactca agatcttcgc tagcctgctg tctcctgtgg   2760
cttttgggtt tggctgtgag tactttgccc tttttgagga gcagggcatt ggagtgcagt   2820
gggacaacct gtttgagagt cctgtggagg aagatggctt caatctcacc acttcggtct   2880
ccatgatgct gtttgacacc ttcctctatg gggtgatgac ctggtacatt gaggctgtct   2940
ttccaggcca gtacggaatt cccaggccct ggtattttcc ttgcaccaag tcctactggt   3000
ttggcgagga aagtgatgag aagagccacc ctggttccaa ccagaagaga atatcagaaa   3060
tctgcatgga ggaggaaccc acccacttga agctgggcgt gtccattcag aacctggtaa   3120
aagtctaccg agatgggatg aaggtggctg tcgatggcct ggcactgaat ttttatgagg   3180
gccagatcac ctccttcctg ggccacaatg gagcggggaa gacgaccacc atgtcaatcc   3240
tgaccgggtt gttccccccg acctcgggca ccgcctacat cctgggaaaa gacattcgct   3300
ctgagatgag caccatccgg cagaacctgg gggtctgtcc ccagcataac gtgctgtttg   3360
acatgctgac tgtcgaagaa cacatctggt tctatgcccg cttgaaaggg ctctctgaga   3420
agcacgtgaa ggcggagatg gagcagatgg ccctggatgt tggtttgcca tcaagcaagc   3480
tgaaaagcaa aacaagccag ctgtcaggtg gaatgcagag aaagctatct gtggccttgg   3540
cctttgtcgg gggatctaag gttgtcattc tggatgaacc cacagctggt gtggaccctt   3600
actcccgcag gggaatatgg gagctgctgc tgaaataccg acaaggccgc accattattc   3660
tctctacaca ccacatggat gaagcggacg tcctggggga caggattgcc atcatctccc   3720
atgggaagct gtgctgtgtg ggctcctccc tgtttctgaa gaaccagctg ggaacaggct   3780
actacctgac cttggtcaag aaagatgtgg aatcctccct cagttcctgc agaaacagta   3840
gtagcactgt gtcatacctg aaaaaggagg acagtgtttc tcagagcagt tctgatgctg   3900
gcctgggcag cgaccatgag agtgacacgc tgaccatcga tgtctctgct atctccaacc   3960
tcatcaggaa gcatgtgtct gaagcccggc tggtggaaga catagggcat gagctgacct   4020
atgtgctgcc atatgaagct gctaaggagg gagcctttgt ggaactcttt catgagattg   4080
atgaccggct ctcagacctg ggcatttcta gttatggcat ctcagagacg accctggaag   4140
aaatattcct caaggtggcc gaagagagtg gggtggatgc tgagacctca gatggtacct   4200
tgccagcaag acgaaacagg cgggccttcg ggacaagca gagctgtctt cgcccgttca   4260
ctgaagatga tgctgctgat ccaaatgatt ctgacataga cccagaatcc agagagacag   4320
acttgctcag tgggatggat ggcaaagggt cctaccaggt gaaaggctgg aaacttacac   4380
agcaacagtt tgtggccctt ttgtggaaga gactgctaat tgccagacgg agtcggaaag   4440
```

-continued gatttttgc tcagattgtc ttgccagctg tgtttgtctg cattgccctt gtgttcagcc 4500
tgatcgtgcc accctttggc aagtacccca gcctggaact tcagccctgg atgtacaacg 4560
aacagtacac atttgtcagc aatgatgctc ctgaggacac gggaaccctg gaactcttaa 4620
acgccctcac caaagaccct ggcttcggga cccgctgtat ggaaggaaac ccaatcccag 4680
acacgccctg ccaggcaggg gaggaagagt ggaccactgc cccagttccc cagaccatca 4740
tggacctctt ccagaatggg aactggacaa tgcagaaccc ttcacctgca tgccagtgta 4800
gcagcgacaa aatcaagaag atgctgcctg tgtgtccccc aggggcaggg gggctgcctc 4860
ctccacaaag aaaacaaaac actgcagata tccttcagga cctgacagga agaaacattt 4920
cggattatct ggtgaagacg tatgtgcaga tcatagccaa aagcttaaag aacaagatct 4980
gggtgaatga gtttaggtat ggcggctttt ccctgggtgt cagtaatact caagcacttc 5040
ctccgagtca agaagttaat gatgccatca aacaaatgaa gaaacaccta aagctggcca 5100
aggacagttc tgcagatcga tttctcaaca gcttgggaag atttatgaca ggactggaca 5160
ccaaaaataa tgtcaaggtg tggttcaata acaagggctg gcatgcaatc agctctttcc 5220
tgaatgtcat caacaatgcc attctccggg ccaacctgca aaagggagag aaccctagcc 5280
attatggaat tactgctttc aatcatcccc tgaatctcac caagcagcag ctctcagagg 5340
tggctctgat gaccacatca gtggatgtcc ttgtgtccat ctgtgtcatc tttgcaatgt 5400
ccttcgtccc agccagcttt gtcgtattcc tgatccagga gcgggtcagc aaagcaaaac 5460
acctgcagtt catcagtgga gtgaagcctg tcatctactg gctctctaat tttgtctggg 5520
atatgtgcaa ttacgttgtc cctgccacac tggtcattat catcttcatc tgcttccagc 5580
agaagtccta tgtgtcctcc accaatctgc ctgtgctagc ccttctactt ttgctgtatg 5640
ggtggtcaat cacacctctc atgtacccag cctcctttgt gttcaagatc cccagcacag 5700
cctatgtggt gctcaccagc gtgaacctct tcattggcat taatggcagc gtggccacct 5760
ttgtgctgga gctgttcacc gacaataagc tgaataatat caatgatatc ctgaagtccg 5820
tgttcttgat cttcccacat ttttgcctgg gacgagggct catcgacatg gtgaaaaacc 5880
aggcaatggc tgatgccctg gaaaggtttg gggagaatcg ctttgtgtca ccattatctt 5940
gggacttggt gggacgaaac ctcttcgcca tggccgtgga aggggtggtg ttcttcctca 6000
ttactgttct gatccagtac agattcttca tcaggcccag acctgtaaat gcaaagctat 6060
ctcctctgaa tgatgaagat gaagatgtga ggcgggaaag acagagaatt cttgatggtg 6120
gaggccagaa tgacatctta gaaatcaagg agttgacgaa gatatataga aggaagcgga 6180
agcctgctgt tgacaggatt tgcgtgggca ttcctcctgg tgagtgcttt gggctcctgg 6240
gagttaatgg ggctggaaaa tcatcaactt tcaagatgtt aacaggagat accactgtta 6300
ccagaggaga tgctttcctt aacaaaaata gtatcttatc aaacatccat gaagtacatc 6360
agaacatggg ctactgccct cagtttgatg ccatcacaga gctgttgact gggagagaac 6420
acgtggagtt ctttgccctt ttgagaggag tcccagagaa agaagttggc aaggttggtg 6480
agtgggcgat tcggaaactg ggcctcgtga agtatggaga aaaatatgct ggtaactata 6540
gtggaggcaa caaacgcaag ctctctacag ccatggcttt gatcggcggg cctcctgtgg 6600
tgtttctgga tgaacccacc acaggcatgg atcccaaagc ccggcggttc ttgtggaatt 6660
gtgccctaag tgttgtcaag gaggggagat cagtagtgct tacatctcat agtatggaag 6720
aatgtgaagc tctttgcact aggatggcaa tcatggtcaa tggaaggttc aggtgccttg 6780
gcagtgtcca gcatctaaaa aataggtttg gagatggtta tacaatagtt gtacgaatag 6840

```
cagggtccaa cccggacctg aagcctgtcc aggatttctt tggacttgca tttcctggaa   6900
gtgttctaaa agagaaacac cggaacatgc tacaatacca gcttccatct tcattatctt   6960
ctctggccag gatattcagc atcctctccc agagcaaaaa gcgactccac atagaagact   7020
actctgtttc tcagacaaca cttgaccaag tatttgtgaa ctttgccaag gaccaaagtg   7080
atgatgacca cttaaaagac ctctcattac acaaaaacca gacagtagtg gacgttgcag   7140
ttctcacatc ttttctacag gatgagaaag tgaaagaaag ctatgtatga agaatcctgt   7200
tcatacgggg tggctgaaag taaagaggaa ctagactttc ctttgcacca tgtgaagtgt   7260
tgtggagaaa agagccagaa gttgatgtgg gaagaagtaa actggatact gtactgatac   7320
tattcaatgc aatgcaattc aatgcaatga aaacaaaatt ccattacagg ggcagtgcct   7380
ttgtagccta tgtcttgtat ggctctcaag tgaaagactt gaatttagtt ttttacctat   7440
acctatgtga aactctatta tggaacccaa tggacatatg ggtttgaact cacacttttt   7500
ttttttttt tgttcctgtg tattctcatt ggggttgcaa caataattca tcaagtaatc   7560
atggccagcg attattgatc aaaatcaaaa ggtaatgcac atcctcattc actaagccat   7620
gccatgccca ggagactggt ttcccggtga cacatccatt gctggcaatg agtgtgccag   7680
agttattagt gccaagtttt tcagaaagtt tgaagcacca tggtgtgtca tgctcacttt   7740
tgtgaaagct gctctgctca gagtctatca acattgaata tcagttgaca gaatggtgcc   7800
atgcgtggct aacatcctgc tttgattccc tctgataagc tgttctggtg gcagtaacat   7860
gcaacaaaaa tgtgggtgtc tccaggcacg ggaaacttgg ttccattgtt atattgtcct   7920
atgcttcgag ccatgggtct acagggtcat ccttatgaga ctcttaaata tacttagatc   7980
ctggtaagag gcaaagaatc aacagccaaa ctgctggggc tgcaagctgc tgaagccagg   8040
gcatgggatt aaagagattg tgcgttcaaa cctagggaag cctgtgccca tttgtcctga   8100
ctgtctgcta acatggtaca ctgcatctca agatgtttat ctgacacaag tgtattattt   8160
ctggcttttt gaattaatct agaaaatgaa aagatggagt tgtattttga caaaaatgtt   8220
tgtacttttt aatgttattt ggaattttaa gttctatcag tgacttctga atccttagaa   8280
tggcctcttt gtagaaccct gtggtataga ggagtatggc cactgcccca ctatttttat   8340
tttcttatgt aagtttgcat atcagtcatg actagtgcct agaaagcaat gtgatggtca   8400
ggatctcatg acattatatt tgagtttctt tcagatcatt taggatactc ttaatctcac   8460
ttcatcaatc aaatattttt tgagtgtatg ctgtagctga aagagtatgt acgtacgtat   8520
aagactagag agatattaag tctcagtaca cttcctgtgc catgttattc agctcactgg   8580
tttacaaata taggttgtct tgtggttgta ggagcccact gtaacaatac tgggcagcct   8640
ttttttttt ttttttaatt gcaacaatgc aaaagccaag aaagtataag ggtcacaagt   8700
ctaaacaatg aattcttcaa cagggaaaac agctagcttg aaaacttgct gaaaaacaca   8760
acttgtgttt atggcattta gtaccttcaa ataattggct ttgcagatat tggatacccc   8820
attaaatctg acagtctcaa atttttcatc tcttcaatca ctagtcaaga aaaatataaa   8880
aacaacaaat acttccatat ggagcatttt tcagagtttt ctaacccagt cttatttttc   8940
tagtcagtaa acatttgtaa aaatactgtt tcactaatac ttactgttaa ctgtcttgag   9000
agaaaagaaa aatatgagag aactattgtt tggggaagtt caagtgatct ttcaatatca   9060
ttactaactt cttccacttt ttccagaatt tgaatattaa cgctaaaggt gtaagacttc   9120
agatttcaaa ttaatctttc tatatttttt aaatttacag aatattatat aacccactgc   9180
```

```
tgaaaaagaa aaaaatgatt gttttagaag ttaaagtcaa tattgatttt aaatataagt   9240
aatgaaggca tatttccaat aactagtgat atggcatcgt tgcattttac agtatcttca   9300
aaaatacaga atttatagaa taatttctcc tcatttaata tttttcaaaa tcaaagttat   9360
ggtttcctca ttttactaaa atcgtattct aattcttcat tatagtaaat ctatgagcaa   9420
ctccttactt cggttcctct gatttcaagg ccatatttta aaaaatcaaa aggcactgtg   9480
aactattttg aagaaaacac aacattttaa tacagattga aaggacctct tctgaagcta   9540
gaaacaatct atagttatac atcttcatta atactgtgtt accttttaaa atagtaattt   9600
tttacatttt cctgtgtaaa cctaattgtg gtagaaattt ttaccaactc tatactcaat   9660
caagcaaaat ttctgtatat tccctgtgga atgtacctat gtgagtttca gaaattctca   9720
aaatacgtgt tcaaaaattt ctgcttttgc atctttggga cacctcagaa aacttattaa   9780
caactgtgaa tatgagaaat acagaagaaa ataataagcc ctctatacat aaatgcccag   9840
cacaattcat tgttaaaaaa caaccaaacc tcacactact gtatttcatt atctgtactg   9900
aaagcaaatg ctttgtgact attaaatgtt gcacatcatt cattcactgt atagtaatca   9960
ttgactaaag ccatttgtct gtgttttctt cttgtggttg tatatatcag gtaaaatatt  10020
ttccaaagag ccatgtgtca tgtaatactg aaccactttg atattgagac attaatttgt  10080
acccttgtta ttatctacta gtaataatgt aatactgtag aaatattgct ctaattcttt  10140
tcaaaattgt tgcatccccc ttagaatgtt tctatttcca taaggattta ggtatgctat  10200
tatcccttct tataccctaa gatgaagctg tttttgtgct ctttgttcat cattggccct  10260
cattccaagc actttacgct gtctgtaatg ggatctattt ttgcactgga atatctgaga  10320
attgcaaaac tagacaaaag tttcacaaca gatttctaag ttaaatcatt ttcattaaaa  10380
ggaaaaaaga aaaaaaattt tgtatgtcaa taactttata tgaagtatta aaatgcatat  10440
ttctatgttg taatataatg agtcacaaaa taaagctgtg acagttctgt tggtctacag  10500
aaaaaaaaaa aaaaa                                                     10515
```

<210> SEQ ID NO 2
<211> LENGTH: 8133
<212> TYPE: DNA
<213> ORGANISM: Homo sapiens

<400> SEQUENCE: 2

```
aatgtgcagg atgacaagat ggagcaaaca gtgcttgtac caccaggacc tgacagcttc     60
aacttcttca ccagagaatc tcttgcggct attgaaagac gcattgcaga agaaaaggca    120
aagaatccca aaccagacaa aaaagatgac gacgaaaatg gcccaaagcc aaatagtgac    180
ttggaagctg gaaagaacct tccatttatt tatggagaca ttcctccaga gatggtgtca    240
gagcccctgg aggacctgga cccctactat atcaataaga aaacttttat agtattgaat    300
aaagggaagg ccatcttccg gttcagtgcc acctctgccc tgtacatttt aactcccttc    360
aatcctctta ggaaaatagc tattaagatt ttggtacatt cattattcag catgctaatt    420
atgtgcacta ttttgacaaa ctgtgtgttt atgacaatga gtaaccctcc tgattggaca    480
aagaatgtag aatacacctt cacaggaata tatacttttg aatcacttat aaaaaattatt    540
gcaaggggat tctgtttaga agattttact ttccttcggg atccatggaa ctggctcgat    600
ttcactgtca ttacatttgc gtacgtcaca gagtttgtgg acctgggcaa tgtctcggca    660
ttgagaacat tcagagttct ccgagcattg aagacgattt cagtcattcc aggcctgaaa    720
accattgtgg gagccctgat ccagtctgtg aagaagctct cagatgtaat gatcctgact    780
```

```
gtgttctgtc tgagcgtatt tgctctaatt gggctgcagc tgttcatggg caacctgagg    840
aataaatgta tacaatggcc tcccaccaat gcttccttgg aggaacatag tatagaaaag    900
aatataactg tgaattataa tggtacactt ataaatgaaa ctgtctttga gtttgactgg    960
aagtcatata ttcaagattc aagatatcat tatttcctgg agggtttttt agatgcacta   1020
ctatgtggaa atagctctga tgcaggccaa tgtccagagg gatatatgtg tgtgaaagct   1080
ggtagaaatc ccaattatgg ctacacaagc tttgatacct tcagttgggc ttttttgtcc   1140
ttgtttcgac taatgactca ggacttctgg gaaaatcttt atcaactgac attacgtgct   1200
gctgggaaaa cgtacatgat attttttgta ttggtcattt tcttgggctc attctaccta   1260
ataaatttga tcctggctgt ggtggccatg gcctacgagg aacagaatca ggccaccttg   1320
gaagaagcag aacagaaaga ggccgaattt cagcagatga ttgaacagct taaaaagcaa   1380
caggaggcag ctcagcaggc agcaacggca actgcctcag aacattccag agagcccagt   1440
gcagcaggca ggctctcaga cagctcatct gaagcctcta agttgagttc caagagtgct   1500
aaggaaagaa gaaatcggag gaagaaaaga aaacagaaag agcagtctgg tggggaagag   1560
aaagatgagg atgaattcca aaaatctgaa tctgaggaca gcatcaggag gaaaggtttt   1620
cgcttctcca ttgaagggaa ccgattgaca tatgaaaaga ggtactcctc cccacaccag   1680
tctttgttga gcatccgtgg ctccctattt tcaccaaggc gaaatagcag aacaagcctt   1740
ttcagcttta gagggcgagc aaaggatgtg ggatctgaga acgacttcgc agatgatgag   1800
cacagcacct ttgaggataa cgagagccgt agagattcct tgtttgtgcc ccgacgacac   1860
ggagagagac gcaacagcaa cctgagtcag accagtaggt catcccggat gctggcagtg   1920
tttccagcga atgggaagat gcacagcact gtggattgca atggtgtggt ttccttggtt   1980
ggtggacctt cagttcctac atcgcctgtt ggacagcttc tgccagaggt gataatagat   2040
aagccagcta ctgatgacaa tggaacaacc actgaaactg aaatgagaaa gagaaggtca   2100
agttctttcc acgtttccat ggactttcta gaagatcctt cccaaaggca acgagcaatg   2160
agtatagcca gcattctaac aaatacagta gaagaacttg aagaatccag gcagaaatgc   2220
ccaccctgtt ggtataaatt ttccaacata ttcttaatct gggactgttc tccatattgg   2280
ttaaaagtga aacatgttgt caacctggtt gtgatggacc catttgttga cctggccatc   2340
accatctgta ttgtcttaaa tactcttttc atggccatgg agcactatcc aatgacggac   2400
catttcaata atgtgcttac agtaggaaac ttggttttca ctgggatctt tacagcagaa   2460
atgtttctga aaattattgc catggatcct tactattatt tccaagaagg ctggaatatc   2520
tttgacggtt ttattgtgac gcttagcctg gtagaacttg gactcgccaa tgtggaagga   2580
ttatctgttc tccgttcatt tcgattgctg cgagttttca agttggcaaa atcttggcca   2640
acgttaaata tgctaataaa gatcatcggc aattccgtgg gggctctggg aaatttaacc   2700
ctcgtcttgg ccatcatcgt cttcattttt gccgtggtcg gcatgcagct ctttggtaaa   2760
agctacaaag attgtgtctg caagatcgcc agtgattgtc aactcccacg ctggcacatg   2820
aatgacttct tccactcctt cctgattgtg ttccgcgtgc tgtgtgggga gtggatagag   2880
accatgtggg actgtatgga ggttgctggt caagccatgt gccttactgt cttcatgatg   2940
gtcatggtga ttggaaacct agtggtcctg aatctctttc tggccttgct tctgagctca   3000
tttagtgcag acaaccttgc agccactgat gatgataatg aaatgaataa tctccaaatt   3060
gctgtggata ggatgcacaa aggagtagct tatgtgaaaa gaaaaatata tgaatttatt   3120
```

caacagtcct tcattaggaa acaaaagatt ttagatgaaa ttaaaccact tgatgatcta 3180
aacaacaaga aagacagttg tatgtccaat catacagcag aaattgggaa agatcttgac 3240
tatcttaaag atgtaaatgg aactacaagt ggtataggaa ctggcagcag tgttgaaaaa 3300
tacattattg atgaaagtga ttacatgtca ttcataaaca accccagtct tactgtgact 3360
gtaccaattg ctgtaggaga atctgacttt gaaaatttaa acacggaaga ctttagtagt 3420
gaatcggatc tggaagaaag caaagagaaa ctgaatgaaa gcagtagctc atcagaaggt 3480
agcactgtgg acatcggcgc acctgtagaa gaacagcccg tagtggaacc tgaagaaact 3540
cttgaaccag aagcttgttt cactgaaggc tgtgtacaaa gattcaagtg ttgtcaaatc 3600
aatgtggaag aaggcagagg aaaacaatgg tggaacctga gaaggacgtg tttccgaata 3660
gttgaacata actggtttga gaccttcatt gttttcatga ttctccttag tagtggtgct 3720
ctggcatttg aagatatata tattgatcag cgaaagacga ttaagacgat gttggaatat 3780
gctgacaagg ttttcactta cattttcatt ctggaaatgc ttctaaaatg ggtggcatat 3840
ggctatcaaa catatttcac caatgcctgg tgttggctgg acttcttaat tgttgatgtt 3900
tcattggtca gtttaacagc aaatgccttg ggttactcag aacttggagc catcaaatct 3960
ctcaggacac taagagctct gagacctcta agagccttat ctcgatttga agggatgagg 4020
gtggttgtga atgccctttt aggagcaatt ccatccatca tgaatgtgct tctggtttgt 4080
cttatattct ggctaatttt cagcatcatg ggcgtaaatt tgtttgctgg caaattctac 4140
cactgtatta acaccacaac tggtgacagg tttgacatcg aagacgtgaa taatcatact 4200
gattgcctaa aactaataga aagaaatgag actgctcgat ggaaaaatgt gaaagtaaac 4260
tttgataatg taggatttgg gtatctctct ttgcttcaag ttgccacatt caaaggatgg 4320
atggatataa tgtatgcagc agttgattcc agaaatgtgg aactccagcc taagtatgaa 4380
gaaagtctgt acatgtatct ttactttgtt attttcatca tctttgggtc cttcttcacc 4440
ttgaacctgt ttattggtgt catcatagat aatttcaacc agcagaaaaa gaagtttgga 4500
ggtcaagaca tctttatgac agaagaacag aagaaatact ataatgcaat gaaaaaatta 4560
ggatcgaaaa aaccgcaaaa gcctatacct cgaccaggaa acaaatttca aggaatggtc 4620
tttgacttcg taaccagaca agtttttgac ataagcatca tgattctcat ctgtcttaac 4680
atggtcacaa tgatggtgga aacagatgac cagagtgaat atgtgactac cattttgtca 4740
cgcatcaatc tggtgttcat tgtgctattt actggagagt gtgtactgaa actcatctct 4800
ctacgccatt attattttac cattggatgg aatatttttg attttgtggt tgtcattctc 4860
tccattgtag gtatgtttct tgccgagctg atagaaaagt atttcgtgtc ccctaccctg 4920
ttccgagtga tccgtcttgc taggattggc cgaatcctac gtctgatcaa aggagcaaag 4980
gggatccgca cgctgctctt tgctttgatg atgtcccttc ctgcgttgtt taacatcggc 5040
ctcctactct tcctagtcat gttcatctac gccatctttg ggatgtccaa ctttgcctat 5100
gttaagaggg aagttgggat cgatgacatg ttcaactttg agacctttgg caacagcatg 5160
atctgcctat tccaaattac aacctctgct ggctgggatg gattgctagc acccattctc 5220
aacagtaagc cacccgactg tgaccctaat aaagttaacc ctggaagctc agttaaggga 5280
gactgtggga acccatctgt tggaattttc ttttttgtca gttacatcat catatccttc 5340
ctggttgtgg tgaacatgta catcgcggtc atcctggaga acttcagtgt tgctactgaa 5400
gaaagtgcag agcctctgag tgaggatgac tttgagatgt tctatgaggt ttgggagaag 5460
tttgatcccg atgcaactca gttcatggaa tttgaaaaat tatctcagtt tgcagctgcg 5520

```
cttgaaccgc ctctcaatct gccacaacca aacaaactcc agctcattgc catggatttg   5580
cccatggtga gtggtgaccg gatccactgt cttgatatct tatttgcttt tacaaagcgg   5640
gttctaggag agagtggaga gatggatgct ctacgaatac agatggaaga gcgattcatg   5700
gcttccaatc cttccaaggt ctcctatcag ccaatcacta ctactttaaa acgaaaacaa   5760
gaggaagtat ctgctgtcat tattcagcgt gcttacagac gccacctttt aaagcgaact   5820
gtaaaacaag cttcctttac gtacaataaa aacaaaatca aaggtggggc taatcttctt   5880
ataaaagaag acatgataat tgacagaata aatgaaaact ctattacaga aaaaactgat   5940
ctgaccatgt ccactgcagc ttgtccacct tcctatgacc gggtgacaaa gccaattgtg   6000
gaaaaacatg agcaagaagg caaagatgaa aaagccaaag ggaaataaat gaaaataaat   6060
aaaaataatt gggtgacaaa ttgtttacag cctgtgaagg tgatgtattt ttatcaacag   6120
gactccttta ggaggtcaat gccaaactga ctgtttttac acaaatctcc ttaaggtcag   6180
tgcctacaat aagacagtga ccccttgtca gcaaactgtg actctgtgta aaggggagat   6240
gaccttgaca ggaggttact gttctcacta ccagctgaca ctgctgaaga taagatgcac   6300
aatggctagt cagactgtag ggaccagttt caaggggtgc aaacctgtga ttttggggtt   6360
gtttaacatg aaacacttta gtgtagtaat tgtatccact gtttgcattt caactgccac   6420
atttgtcaca tttttatgga atctgttagt ggattcatct tttgttaat ccatgtgttt    6480
attatatgtg actatttttg taaacgaagt ttctgttgag aaataggcta aggacctcta   6540
taacaggtat gccacctggg ggtatggca accacatggc cctcccagct acacaaagtc    6600
gtggtttgca tgagggcatg ctgcacttag agatcatgca tgagaaaaag tcacaagaaa   6660
aacaaattct taaatttcac catatttctg ggaggggtaa ttgggtgata agtggaggtg   6720
ctttgttgat cttgttttgc gaaatccagc ccctagacca agtagattat ttgtgggtag   6780
gccagtaaat cttagcaggt gcaaacttca ttcaaatgtt tggagtcata aatgttatgt   6840
ttctttttgt tgtattaaaa aaaaaacctg aatagtgaat attgcccctc accctccacc   6900
gccagaagac tgaattgacc aaaattactc tttataaatt tctgcttttt cctgcacttt   6960
gtttagccat cttcggctct cagcaaggtt gacactgtat atgttaatga aatgctattt   7020
attatgtaaa tagtcatttt accctgtggt gcacgtttga gcaaacaaat aatgacctaa   7080
gcacagtatt tattgcatca aatatgtacc acaagaaatg tagagtgcaa gctttacaca   7140
ggtaataaaa tgtattctgt accatttata gatagtttgg atgctatcaa tgcatgttta   7200
tattaccatg ctgctgtatc tggtttctct cactgctcag aatctcattt atgagaaacc   7260
atatgtcagt ggtaaagtca aggaaattgt tcaacagatc tcatttattt aagtcattaa   7320
gcaatagttt gcagcacttt aacagctttt tggttatttt tacattttaa gtggataaca   7380
tatggtatat agccagactg tacagacatg tttaaaaaaa cacactgctt aacctattaa   7440
atatgtgttt agaattttat aagcaaatat aaatactgta aaaagtcact ttattttatt   7500
tttcagcatt atgtacataa atatgaagag gaaattatct tcaggttgat atcacaatca   7560
cttttcttac tttctgtcca tagtactttt tcatgaaaga aatttgctaa ataagacatg   7620
aaaacaagac tgggtagttg tagatttctg ctttttaaat tacatttgct aattttagat   7680
tatttcacaa ttttaaggag caaaataggt tcacgattca tatccaaatt atgctttgca   7740
attggaaaag ggtttaaaat tttatttata tttctggtag tacctgcact aactgaattg   7800
aaggtagtgc ttatgttatt tttgttcttt ttttctgact tcggtttatg ttttcatttc   7860
```

-continued

```
tttggagtaa tgctgctcta gattgttcta aatagaatgt gggcttcata attttttttt   7920

ccacaaaaac agagtagtca acttatatag tcaattacat caggacattt tgtgtttctt   7980

acagaagcaa accataggct cctcttttcc ttaaaactac ttagataaac tgtattcgtg   8040

aactgcatgc tggaaaatgc tactattatg ctaaataatg ctaaccaaca tttaaaatgt   8100

gcaaaactaa taaagattac attttttatt tta                                 8133
```

<210> SEQ ID NO 3
<211> LENGTH: 8100
<212> TYPE: DNA
<213> ORGANISM: Homo sapiens

<400> SEQUENCE: 3

```
aatgtgcagg atgacaagat ggagcaaaca gtgcttgtac caccaggacc tgacagcttc     60

aacttcttca ccagagaatc tcttgcggct attgaaagac gcattgcaga agaaaaggca    120

aagaatccca aaccagacaa aaaagatgac gacgaaaatg gcccaaagcc aaatagtgac    180

ttggaagctg gaaagaacct tccatttatt tatggagaca ttcctccaga gatggtgtca    240

gagcccctgg aggacctgga cccctactat atcaataaga aaacttttat agtattgaat    300

aaagggaagg ccatcttccg gttcagtgcc acctctgccc tgtacatttt aactcccttc    360

aatcctctta ggaaaatagc tattaagatt ttggtacatt cattattcag catgctaatt    420

atgtgcacta ttttgacaaa ctgtgtgttt atgacaatga gtaaccctcc tgattggaca    480

aagaatgtag aatacacctt cacaggaata tatacttttg aatcacttat aaaaattatt    540

gcaaggggat tctgtttaga agattttact ttccttcggg atccatggaa ctggctcgat    600

ttcactgtca ttacatttgc gtacgtcaca gagtttgtgg acctgggcaa tgtctcggca    660

ttgagaacat tcagagttct ccgagcattg aagacgattt cagtcattcc aggcctgaaa    720

accattgtgg gagccctgat ccagtctgtg aagaagctct cagatgtaat gatcctgact    780

gtgttctgtc tgagcgtatt tgctctaatt gggctgcagc tgttcatggg caacctgagg    840

aataaatgta tacaatggcc tcccaccaat gcttccttgg aggaacatag tatagaaaag    900

aatataactg tgaattataa tggtacactt ataaatgaaa ctgtctttga gtttgactgg    960

aagtcatata ttcaagattc aagatatcat tatttcctgg agggtttttt agatgcacta   1020

ctatgtggaa atagctctga tgcaggccaa tgtccagagg gatatatgtg tgtgaaagct   1080

ggtagaaatc ccaattatgg ctacacaagc tttgatacct tcagttgggc tttttttgtcc  1140

ttgtttcgac taatgactca ggacttctgg gaaaatcttt atcaactgac attacgtgct   1200

gctgggaaaa cgtacatgat atttttttgta ttggtcattt tcttgggctc attctaccta  1260

ataaatttga tcctggctgt ggtggccatg gcctacgagg aacagaatca ggccaccttg   1320

gaagaagcag aacagaaaga ggccgaattt cagcagatga ttgaacagct taaaaagcaa   1380

caggaggcag ctcagcaggc agcaacggca actgcctcag aacattccag agagcccagt   1440

gcagcaggca ggctctcaga cagctcatct gaagcctcta agttgagttc caagagtgct   1500

aaggaaagaa gaaatcggag gaagaaaaga aaacagaaag agcagtctgg tggggaagag   1560

aaagatgagg atgaattcca aaaatctgaa tctgaggaca gcatcaggag gaaaggtttt   1620

cgcttctcca ttgaagggaa ccgattgaca tatgaaaaga ggtactcctc cccacaccag   1680

tctttgttga gcatccgtgg ctccctattt tcaccaaggc gaaatagcag aacaagcctt   1740

ttcagcttta gagggcgagc aaaggatgtg ggatctgaga acgacttcgc agatgatgag   1800

cacagcacct ttgaggataa cgagagccgt agagattcct tgtttgtgcc ccgacgacac   1860
```

-continued

```
ggagagagac gcaacagcaa cctgagtcag accagtaggt catcccggat gctggcagtg   1920
tttccagcga atgggaagat gcacagcact gtggattgca atggtgtggt ttccttggtt   1980
ggtggacctt cagttcctac atcgcctgtt ggacagcttc tgccagaggg aacaaccact   2040
gaaactgaaa tgagaaagag aaggtcaagt tctttccacg tttccatgga ctttctagaa   2100
gatccttccc aaaggcaacg agcaatgagt atagccagca ttctaacaaa tacagtagaa   2160
gaacttgaag aatccaggca gaaatgccca ccctgttggt ataaattttc caacatattc   2220
ttaatctggg actgttctcc atattggtta aaagtgaaac atgttgtcaa cctggttgtg   2280
atggacccat ttgttgacct ggccatcacc atctgtattg tcttaaatac tcttttcatg   2340
gccatggagc actatccaat gacggaccat ttcaataatg tgcttacagt aggaaacttg   2400
gttttcactg ggatctttac agcagaaatg tttctgaaaa ttattgccat ggatccttac   2460
tattatttcc aagaaggctg gaatatcttt gacggtttta ttgtgacgct tagcctggta   2520
gaacttggac tcgccaatgt ggaaggatta tctgttctcc gttcatttcg attgctgcga   2580
gttttcaagt tggcaaaatc ttggccaacg ttaaatatgc taataaagat catcggcaat   2640
tccgtggggg ctctgggaaa tttaaccctc gtcttggcca tcatcgtctt catttttgcc   2700
gtggtcggca tgcagctctt tggtaaaagc tacaaagatt gtgtctgcaa gatcgccagt   2760
gattgtcaac tcccacgctg gcacatgaat gacttcttcc actccttcct gattgtgttc   2820
cgcgtgctgt gtggggagtg gatagagacc atgtgggact gtatggaggt tgctggtcaa   2880
gccatgtgcc ttactgtctt catgatggtc atggtgattg gaaacctagt ggtcctgaat   2940
ctctttctgg ccttgcttct gagctcattt agtgcagaca accttgcagc cactgatgat   3000
gataatgaaa tgaataatct ccaaattgct gtggatagga tgcacaaagg agtagcttat   3060
gtgaaaagaa aaatatatga atttattcaa cagtccttca ttaggaaaca aaagatttta   3120
gatgaaatta aaccacttga tgatctaaac aacaagaaag acagttgtat gtccaatcat   3180
acagcagaaa ttgggaaaga tcttgactat cttaaagatg taaatggaac tacaagtggt   3240
ataggaactg gcagcagtgt tgaaaaatac attattgatg aaagtgatta catgtcattc   3300
ataaacaacc ccagtcttac tgtgactgta ccaattgctg taggagaatc tgactttgaa   3360
aatttaaaca cggaagactt tagtagtgaa tcggatctgg aagaaagcaa agagaaactg   3420
aatgaaagca gtagctcatc agaaggtagc actgtggaca tcggcgcacc tgtagaagaa   3480
cagcccgtag tggaacctga agaaactctt gaaccagaag cttgtttcac tgaaggctgt   3540
gtacaaagat tcaagtgttg tcaaatcaat gtggaagaag gcagaggaaa acaatggtgg   3600
aacctgagaa ggacgtgttt ccgaatagtt gaacataact ggtttgagac cttcattgtt   3660
ttcatgattc tccttagtag tggtgctctg gcatttgaag atatatatat tgatcagcga   3720
aagacgatta agacgatgtt ggaatatgct gacaaggttt tcacttacat tttcattctg   3780
gaaatgcttc taaaatgggt ggcatatggc tatcaaacat atttcaccaa tgcctggtgt   3840
tggctggact tcttaattgt tgatgtttca ttggtcagtt taacagcaaa tgccttgggt   3900
tactcagaac ttggagccat caaatctctc aggacactaa gagctctgag acctctaaga   3960
gccttatctc gatttgaagg gatgagggtg gttgtgaatg ccctttttagg agcaattcca   4020
tccatcatga atgtgcttct ggtttgtctt atattctggc taattttcag catcatgggc   4080
gtaaatttgt ttgctggcaa attctaccac tgtattaaca ccacaactgg tgacaggttt   4140
gacatcgaag acgtgaataa tcatactgat tgcctaaaac taatagaaag aaatgagact   4200
```

gctcgatgga aaaatgtgaa agtaaacttt gataatgtag gatttgggta tctctctttg 4260
cttcaagttg ccacattcaa aggatggatg gatataatgt atgcagcagt tgattccaga 4320
aatgtggaac tccagcctaa gtatgaagaa agtctgtaca tgtatcttta ctttgttatt 4380
ttcatcatct ttgggtcctt cttcaccttg aacctgttta ttggtgtcat catagataat 4440
ttcaaccagc agaaaaagaa gtttggaggt caagacatct ttatgacaga agaacagaag 4500
aaatactata atgcaatgaa aaaattagga tcgaaaaaac cgcaaaagcc tatacctcga 4560
ccaggaaaca aatttcaagg aatggtcttt gacttcgtaa ccagacaagt ttttgacata 4620
agcatcatga ttctcatctg tcttaacatg gtcacaatga tggtggaaac agatgaccag 4680
agtgaatatg tgactaccat tttgtcacgc atcaatctgg tgttcattgt gctatttact 4740
ggagagtgtg tactgaaact catctctcta cgccattatt attttaccat tggatggaat 4800
atttttgatt ttgtggttgt cattctctcc attgtaggta tgtttcttgc cgagctgata 4860
gaaaagtatt tcgtgtcccc taccctgttc cgagtgatcc gtcttgctag gattggccga 4920
atcctacgtc tgatcaaagg agcaaagggg atccgcacgc tgctctttgc tttgatgatg 4980
tcccttcctg cgttgtttaa catcggcctc ctactcttcc tagtcatgtt catctacgcc 5040
atctttggga tgtccaactt tgcctatgtt aagagggaag ttgggatcga tgacatgttc 5100
aactttgaga cctttggcaa cagcatgatc tgcctattcc aaattacaac ctctgctggc 5160
tgggatggat tgctagcacc cattctcaac agtaagccac ccgactgtga ccctaataaa 5220
gttaaccctg gaagctcagt taagggagac tgtgggaacc catctgttgg aatttttctt 5280
tttgtcagtt acatcatcat atccttcctg gttgtggtga acatgtacat cgcggtcatc 5340
ctggagaact tcagtgttgc tactgaagaa agtgcagagc ctctgagtga ggatgacttt 5400
gagatgttct atgaggtttg ggagaagttt gatcccgatg caactcagtt catggaattt 5460
gaaaaattat ctcagtttgc agctgcgctt gaaccgcctc tcaatctgcc acaaccaaac 5520
aaactccagc tcattgccat ggatttgccc atggtgagtg gtgaccggat ccactgtctt 5580
gatatcttat ttgcttttac aaagcgggtt ctaggagaga gtggagagat ggatgctcta 5640
cgaatacaga tggaagagcg attcatggct tccaatcctt ccaaggtctc ctatcagcca 5700
atcactacta ctttaaaacg aaaacaagag gaagtatctg ctgtcattat tcagcgtgct 5760
tacagacgcc accttttaaa gcgaactgta aaacaagctt cctttacgta caataaaaac 5820
aaaatcaaag gtggggctaa tcttcttata aaagaagaca tgataattga cagaataaat 5880
gaaaactcta ttacagaaaa aactgatctg accatgtcca ctgcagcttg tccaccttcc 5940
tatgaccggg tgacaaagcc aattgtggaa aaacatgagc aagaaggcaa agatgaaaaa 6000
gccaaaggga aataaatgaa aataaataaa aataattggg tgacaaattg tttacagcct 6060
gtgaaggtga tgtattttta tcaacaggac tcctttagga ggtcaatgcc aaactgactg 6120
tttttacaca aatctcctta aggtcagtgc ctacaataag acagtgaccc cttgtcagca 6180
aactgtgact ctgtgtaaag gggagatgac cttgacagga ggttactgtt ctcactacca 6240
gctgacactg ctgaagataa gatgcacaat ggctagtcag actgtaggga ccagtttcaa 6300
ggggtgcaaa cctgtgattt tggggttgtt taacatgaaa cactttagtg tagtaattgt 6360
atccactgtt tgcatttcaa ctgccacatt tgtcacattt ttatggaatc tgttagtgga 6420
ttcatctttt tgttaatcca tgtgtttatt atatgtgact atttttgtaa acgaagtttc 6480
tgttgagaaa taggctaagg acctctataa caggtatgcc acctgggggg tatggcaacc 6540
acatggccct cccagctaca caaagtcgtg gtttgcatga gggcatgctg cacttagaga 6600

-continued

```
tcatgcatga gaaaaagtca caagaaaaac aaattcttaa atttcaccat atttctggga   6660
ggggtaattg ggtgataagt ggaggtgctt tgttgatctt gttttgcgaa atccagcccc   6720
tagaccaagt agattatttg tgggtaggcc agtaaatctt agcaggtgca aacttcattc   6780
aaatgtttgg agtcataaat gttatgtttc tttttgttgt attaaaaaaa aaacctgaat   6840
agtgaatatt gcccctcacc ctccaccgcc agaagactga attgaccaaa attactcttt   6900
ataaatttct gctttttcct gcactttgtt tagccatctt cggctctcag caaggttgac   6960
actgtatatg ttaatgaaat gctatttatt atgtaaatag tcattttacc ctgtggtgca   7020
cgtttgagca aacaaataat gacctaagca cagtatttat tgcatcaaat atgtaccaca   7080
agaaatgtag agtgcaagct ttacacaggt aataaaatgt attctgtacc atttatagat   7140
agtttggatg ctatcaatgc atgtttatat taccatgctg ctgtatctgg tttctctcac   7200
tgctcagaat ctcatttatg agaaaccata tgtcagtggt aaagtcaagg aaattgttca   7260
acagatctca tttatttaag tcattaagca atagtttgca gcactttaac agctttttgg   7320
ttatttttac attttaagtg gataacatat ggtatatagc cagactgtac agacatgttt   7380
aaaaaaacac actgcttaac ctattaaata tgtgtttaga attttataag caaatataaa   7440
tactgtaaaa agtcacttta ttttattttt cagcattatg tacataaata tgaagaggaa   7500
attatcttca ggttgatatc acaatcactt ttcttacttt ctgtccatag tacttttttca   7560
tgaaagaaat ttgctaaata agacatgaaa acaagactgg gtagttgtag atttctgctt   7620
tttaaattac atttgctaat tttagattat ttcacaattt taaggagcaa aataggttca   7680
cgattcatat ccaaattatg ctttgcaatt ggaaaagggt ttaaaatttt atttatattt   7740
ctggtagtac ctgcactaac tgaattgaag gtagtgctta tgttattttt gttctttttt   7800
tctgacttcg gtttatgttt tcatttcttt ggagtaatgc tgctctagat tgttctaaat   7860
agaatgtggg cttcataatt ttttttccca caaaaacaga gtagtcaact tatatagtca   7920
attacatcag gacattttgt gtttcttaca gaagcaaacc ataggctcct cttttcctta   7980
aaactactta gataaactgt attcgtgaac tgcatgctgg aaaatgctac tattatgcta   8040
aataatgcta accaacattt aaaatgtgca aaactaataa agattacatt ttttatttta   8100
```

<210> SEQ ID NO 4
<211> LENGTH: 8049
<212> TYPE: DNA
<213> ORGANISM: Homo sapiens

<400> SEQUENCE: 4

```
aatgtgcagg atgacaagat ggagcaaaca gtgcttgtac caccaggacc tgacagcttc     60
aacttcttca ccagagaatc tcttgcggct attgaaagac gcattgcaga agaaaaggca    120
aagaatccca aaccagacaa aaaagatgac gacgaaaatg gcccaaagcc aaatagtgac    180
ttggaagctg gaaagaacct tccatttatt tatggagaca ttcctccaga gatggtgtca    240
gagcccctgg aggacctgga cccctactat atcaataaga aaacttttat agtattgaat    300
aaagggaagg ccatcttccg gttcagtgcc acctctgccc tgtacatttt aactcccttc    360
aatcctctta ggaaaatagc tattaagatt ttggtacatt cattattcag catgctaatt    420
atgtgcacta ttttgacaaa ctgtgtgttt atgacaatga gtaaccctcc tgattggaca    480
aagaatgtag aatacacctt cacaggaata tatacttttg aatcacttat aaaaaattatt    540
gcaaggggat tctgtttaga agattttact ttccttcggg atccatggaa ctggctcgat    600
```

```
ttcactgtca ttacatttgc gtacgtcaca gagtttgtgg acctgggcaa tgtctcggca    660
ttgagaacat tcagagttct ccgagcattg aagacgattt cagtcattcc aggcctgaaa    720
accattgtgg gagccctgat ccagtctgtg aagaagctct cagatgtaat gatcctgact    780
gtgttctgtc tgagcgtatt tgctctaatt gggctgcagc tgttcatggg caacctgagg    840
aataaatgta tacaatggcc tcccaccaat gcttccttgg aggaacatag tatagaaaag    900
aatataactg tgaattataa tggtacactt ataaatgaaa ctgtctttga gtttgactgg    960
aagtcatata ttcaagattc aagatatcat tatttcctgg agggtttttt agatgcacta   1020
ctatgtggaa atagctctga tgcaggccaa tgtccagagg gatatatgtg tgtgaaagct   1080
ggtagaaatc ccaattatgg ctacacaagc tttgatacct tcagttgggc tttttttgtcc  1140
ttgtttcgac taatgactca ggacttctgg gaaaatcttt atcaactgac attacgtgct   1200
gctgggaaaa cgtacatgat atttttttgta ttggtcattt tcttgggctc attctaccta  1260
ataaatttga tcctggctgt ggtggccatg gcctacgagg aacagaatca ggccaccttg   1320
gaagaagcag aacagaaaga ggccgaattt cagcagatga ttgaacagct taaaaagcaa   1380
caggaggcag ctcagcaggc agcaacggca actgcctcag aacattccag agagcccagt   1440
gcagcaggca ggctctcaga cagctcatct gaagcctcta agttgagttc caagagtgct   1500
aaggaaagaa gaaatcggag gaagaaaaga aaacagaaag agcagtctgg tggggaagag   1560
aaagatgagg atgaattcca aaaatctgaa tctgaggaca gcatcaggag gaaaggtttt   1620
cgcttctcca ttgaagggaa ccgattgaca tatgaaaaga ggtactcctc cccacaccag   1680
tctttgttga gcatccgtgg ctccctattt tcaccaaggc gaaatagcag aacaagcctt   1740
ttcagcttta gagggcgagc aaaggatgtg ggatctgaga acgacttcgc agatgatgag   1800
cacagcacct ttgaggataa cgagagccgt agagattcct tgtttgtgcc ccgacgacac   1860
ggagagagac gcaacagcaa cctgagtcag accagtaggt catcccggat gctggcagtg   1920
tttccagcga atgggaagat gcacagcact gtggattgca atggtgtggt ttccttggga   1980
acaaccactg aaactgaaat gagaaagaga aggtcaagtt ctttccacgt ttccatggac   2040
tttctagaag atccttccca aaggcaacga gcaatgagta tagccagcat tctaacaaat   2100
acagtagaag aacttgaaga atccaggcag aaatgcccac cctgttggta taaattttcc   2160
aacatattct taatctggga ctgttctcca tattggttaa aagtgaaaca tgttgtcaac   2220
ctggttgtga tggacccatt tgttgacctg gccatcacca tctgtattgt cttaaatact   2280
cttttcatgg ccatggagca ctatccaatg acggaccatt tcaataatgt gcttacagta   2340
ggaaacttgg ttttcactgg gatctttaca gcagaaatgt ttctgaaaat tattgccatg   2400
gatccttact attatttcca agaaggctgg aatatctttg acggttttat tgtgacgctt   2460
agcctggtag aacttggact cgccaatgtg gaaggattat ctgttctccg ttcatttcga   2520
ttgctgcgag ttttcaagtt ggcaaaatct tggccaacgt taaatatgct aataaagatc   2580
atcggcaatt ccgtgggggc tctgggaaat ttaaccctcg tcttggccat catcgtcttc   2640
atttttgccg tggtcggcat gcagctcttt ggtaaaagct acaaagattg tgtctgcaag   2700
atcgccagtg attgtcaact cccacgctgg cacatgaatg acttcttcca ctccttcctg   2760
attgtgttcc gcgtgctgtg tggggagtgg atagagacca tgtgggactg tatggaggtt   2820
gctggtcaag ccatgtgcct tactgtcttc atgatggtca tggtgattgg aaacctagtg   2880
gtcctgaatc tctttctggc cttgcttctg agctcattta gtgcagacaa ccttgcagcc   2940
actgatgatg ataatgaaat gaataatctc caaattgctg tggataggat gcacaaagga   3000
```

-continued

```
gtagcttatg tgaaaagaaa aatatatgaa tttattcaac agtccttcat taggaaacaa   3060
aagattttag atgaaattaa accacttgat gatctaaaca acaagaaaga cagttgtatg   3120
tccaatcata cagcagaaat tgggaaagat cttgactatc ttaaagatgt aaatggaact   3180
acaagtggta taggaactgg cagcagtgtt gaaaaataca ttattgatga aagtgattac   3240
atgtcattca taaacaaccc cagtcttact gtgactgtac caattgctgt aggagaatct   3300
gactttgaaa atttaaacac ggaagacttt agtagtgaat cggatctgga agaaagcaaa   3360
gagaaactga atgaaagcag tagctcatca gaaggtagca ctgtggacat cggcgcacct   3420
gtagaagaac agcccgtagt ggaacctgaa gaaactcttg aaccagaagc ttgtttcact   3480
gaaggctgtg tacaaagatt caagtgttgt caaatcaatg tggaagaagg cagaggaaaa   3540
caatggtgga acctgagaag gacgtgtttc cgaatagttg aacataactg gtttgagacc   3600
ttcattgttt tcatgattct ccttagtagt ggtgctctgg catttgaaga tatatatatt   3660
gatcagcgaa agacgattaa gacgatgttg gaatatgctg acaaggtttt cacttacatt   3720
ttcattctgg aaatgcttct aaaatgggtg gcatatggct atcaaacata tttcaccaat   3780
gcctggtgtt ggctggactt cttaattgtt gatgtttcat tggtcagttt aacagcaaat   3840
gccttgggtt actcagaact tggagccatc aaatctctca ggacactaag agctctgaga   3900
cctctaagag ccttatctcg atttgaaggg atgagggtgg ttgtgaatgc ccttttagga   3960
gcaattccat ccatcatgaa tgtgcttctg gtttgtctta tattctggct aattttcagc   4020
atcatgggcg taaatttgtt tgctggcaaa ttctaccact gtattaacac cacaactggt   4080
gacaggtttg acatcgaaga cgtgaataat catactgatt gcctaaaact aatagaaaga   4140
aatgagactg ctcgatggaa aaatgtgaaa gtaaactttg ataatgtagg atttgggtat   4200
ctctctttgc ttcaagttgc cacattcaaa ggatggatgg atataatgta tgcagcagtt   4260
gattccagaa atgtggaact ccagcctaag tatgaagaaa gtctgtacat gtatctttac   4320
tttgttattt tcatcatctt tgggtccttc ttcaccttga acctgtttat tggtgtcatc   4380
atagataatt tcaaccagca gaaaaagaag tttggaggtc aagacatctt tatgacagaa   4440
gaacagaaga aatactataa tgcaatgaaa aaattaggat cgaaaaaacc gcaaaagcct   4500
atacctcgac caggaaacaa atttcaagga atggtctttg acttcgtaac cagacaagtt   4560
tttgacataa gcatcatgat tctcatctgt cttaacatgg tcacaatgat ggtggaaaca   4620
gatgaccaga gtgaatatgt gactaccatt ttgtcacgca tcaatctggt gttcattgtg   4680
ctatttactg gagagtgtgt actgaaactc atctctctac gccattatta ttttaccatt   4740
ggatggaata tttttgattt tgtggttgtc attctctcca ttgtaggtat gtttcttgcc   4800
gagctgatag aaaagtattt cgtgtcccct accctgttcc gagtgatccg tcttgctagg   4860
attggccgaa tcctacgtct gatcaaagga gcaaagggga tccgcacgct gctctttgct   4920
ttgatgatgt cccttcctgc gttgtttaac atcggcctcc tactcttcct agtcatgttc   4980
atctacgcca tctttgggat gtccaacttt gcctatgtta agagggaagt tgggatcgat   5040
gacatgttca actttgagac ctttggcaac agcatgatct gcctattcca aattacaacc   5100
tctgctggct gggatggatt gctagcaccc attctcaaca gtaagccacc cgactgtgac   5160
cctaataaag ttaaccctgg aagctcagtt aagggagact gtgggaaccc atctgttgga   5220
attttctttt ttgtcagtta catcatcata tccttcctgg ttgtggtgaa catgtacatc   5280
gcggtcatcc tggagaactt cagtgttgct actgaagaaa gtgcagagcc tctgagtgag   5340
```

-continued

```
gatgactttg agatgttcta tgaggtttgg gagaagtttg atcccgatgc aactcagttc   5400
atggaatttg aaaaattatc tcagtttgca gctgcgcttg aaccgcctct caatctgcca   5460
caaccaaaca aactccagct cattgccatg gatttgccca tggtgagtgg tgaccggatc   5520
cactgtcttg atatcttatt tgcttttaca aagcgggttc taggagagag tggagagatg   5580
gatgctctac gaatacagat ggaagagcga ttcatggctt ccaatccttc caaggtctcc   5640
tatcagccaa tcactactac tttaaaacga aaacaagagg aagtatctgc tgtcattatt   5700
cagcgtgctt acagacgcca ccttttaaag cgaactgtaa aacaagcttc ctttacgtac   5760
aataaaaaca aaatcaaagg tggggctaat cttcttataa aagaagacat gataattgac   5820
agaataaatg aaaactctat tacagaaaaa actgatctga ccatgtccac tgcagcttgt   5880
ccaccttcct atgaccgggt gacaaagcca attgtggaaa aacatgagca agaaggcaaa   5940
gatgaaaaag ccaaagggaa ataaatgaaa ataaataaaa ataattgggt gacaaattgt   6000
ttacagcctg tgaaggtgat gtatttttat caacaggact cctttaggag gtcaatgcca   6060
aactgactgt tttacacaa atctccttaa ggtcagtgcc tacaataaga cagtgacccc   6120
ttgtcagcaa actgtgactc tgtgtaaagg ggagatgacc ttgacaggag gttactgttc   6180
tcactaccag ctgacactgc tgaagataag atgcacaatg gctagtcaga ctgtagggac   6240
cagtttcaag ggtgcaaac ctgtgatttt ggggttgttt aacatgaaac actttagtgt   6300
agtaattgta tccactgttt gcatttcaac tgccacattt gtcacatttt tatggaatct   6360
gttagtggat tcatcttttt gttaatccat gtgtttatta tatgtgacta tttttgtaaa   6420
cgaagtttct gttgagaaat aggctaagga cctctataac aggtatgcca cctggggggt   6480
atggcaacca catggccctc ccagctacac aaagtcgtgg tttgcatgag ggcatgctgc   6540
acttagagat catgcatgag aaaaagtcac aagaaaaaca aattcttaaa tttcaccata   6600
tttctgggag gggtaattgg gtgataagtg gaggtgcttt gttgatcttg ttttgcgaaa   6660
tccagcccct agaccaagta gattatttgt gggtaggcca gtaaatctta gcaggtgcaa   6720
acttcattca aatgtttgga gtcataaatg ttatgtttct ttttgttgta ttaaaaaaaa   6780
aacctgaata gtgaatattg cccctcaccc tccaccgcca gaagactgaa ttgaccaaaa   6840
ttactcttta taaatttctg ctttttcctg cactttgttt agccatcttc ggctctcagc   6900
aaggttgaca ctgtatatgt taatgaaatg ctatttatta tgtaaatagt cattttaccc   6960
tgtggtgcac gtttgagcaa acaaataatg acctaagcac agtatttatt gcatcaaata   7020
tgtaccacaa gaaatgtaga gtgcaagctt tacacaggta ataaaatgta ttctgtacca   7080
tttatagata gtttggatgc tatcaatgca tgtttatatt accatgctgc tgtatctggt   7140
ttctctcact gctcagaatc tcatttatga gaaaccatat gtcagtggta aagtcaagga   7200
aattgttcaa cagatctcat ttatttaagt cattaagcaa tagtttgcag cactttaaca   7260
gctttttggt tatttttaca ttttaagtgg ataacatatg gtatatagcc agactgtaca   7320
gacatgttta aaaaaacaca ctgcttaacc tattaaatat gtgtttagaa ttttataagc   7380
aaatataaat actgtaaaaa gtcactttat tttattttc agcattatgt acataaatat   7440
gaagaggaaa ttatcttcag gttgatatca caatcacttt tcttactttc tgtccatagt   7500
actttttcat gaaagaaatt tgctaaataa gacatgaaaa caagactggg tagttgtaga   7560
tttctgcttt ttaaattaca tttgctaatt ttagattatt tcacaatttt aaggagcaaa   7620
ataggttcac gattcatatc caaattatgc tttgcaattg gaaaagggtt taaaatttta   7680
tttatatttc tggtagtacc tgcactaact gaattgaagg tagtgcttat gttatttttg   7740
```

-continued ttcttttttt ctgacttcgg tttatgtttt catttctttg gagtaatgct gctctagatt 7800
gttctaaata gaatgtgggc ttcataattt ttttttccac aaaaacagag tagtcaactt 7860
atatagtcaa ttacatcagg acattttgtg tttcttacag aagcaaacca taggctcctc 7920
ttttccttaa aactacttag ataaactgta ttcgtgaact gcatgctgga aaatgctact 7980
attatgctaa ataatgctaa ccaacattta aaatgtgcaa aactaataaa gattacattt 8040
tttattta 8049

<210> SEQ ID NO 5
<211> LENGTH: 8342
<212> TYPE: DNA
<213> ORGANISM: Homo sapiens

<400> SEQUENCE: 5
gaaactcatg gaactgttcc tccagattaa cacttcaggg gttatggaag ctggaggaag 60
ctgagctttt actacatctt ttgggggttt gggcaattat gaataaggct gctgtataca 120
tccgtgtgca ggattttgtg tggacataag ttttcaactc ctttggttaa atcctaagga 180
atttcatatg cagaataaat ggtaattaaa atgtgcagga tgacaagatg gagcaaacag 240
tgcttgtacc accaggacct gacagcttca acttcttcac cagagaatct cttgcggcta 300
ttgaaagacg cattgcagaa gaaaaggcaa agaatcccaa accagacaaa aaagatgacg 360
acgaaaatgg cccaaagcca aatagtgact tggaagctgg aaagaacctt ccatttattt 420
atggagacat tcctccagag atggtgtcag agcccctgga ggacctggac ccctactata 480
tcaataagaa aacttttata gtattgaata aagggaaggc catcttccgg ttcagtgcca 540
cctctgccct gtacatttta actcccttca atcctcttag gaaaatagct attaagattt 600
tggtacattc attattcagc atgctaatta tgtgcactat tttgacaaac tgtgtgttta 660
tgacaatgag taaccctcct gattggacaa agaatgtaga atacaccttc acaggaatat 720
atacttttga atcacttata aaaattattg caaggggatt ctgtttagaa gattttactt 780
tccttcggga tccatggaac tggctcgatt tcactgtcat tacatttgcg tacgtcacag 840
agtttgtgga cctgggcaat gtctcggcat tgagaacatt cagagttctc cgagcattga 900
agacgatttc agtcattcca ggcctgaaaa ccattgtggg agccctgatc cagtctgtga 960
agaagctctc agatgtaatg atcctgactg tgttctgtct gagcgtattt gctctaattg 1020
ggctgcagct gttcatgggc aacctgagga ataaatgtat acaatggcct cccaccaatg 1080
cttccttgga ggaacatagt atagaaaaga atataactgt gaattataat ggtacactta 1140
taaatgaaac tgtctttgag tttgactgga agtcatatat tcaagattca agatatcatt 1200
atttcctgga gggtttttta gatgcactac tatgtggaaa tagctctgat gcaggccaat 1260
gtccagaggg atatatgtgt gtgaaagctg gtagaaatcc caattatggc tacacaagct 1320
ttgatacctt cagttgggct tttttgtcct tgtttcgact aatgactcag gacttctggg 1380
aaaatcttta tcaactgaca ttacgtgctg ctgggaaaac gtacatgata ttttttgtat 1440
tggtcatttt cttgggctca ttctacctaa taaatttgat cctggctgtg gtggccatgg 1500
cctacgagga acagaatcag gccaccttgg aagaagcaga acagaaagag gccgaatttc 1560
agcagatgat tgaacagctt aaaaagcaac aggaggcagc tcagcaggca gcaacggcaa 1620
ctgcctcaga acattccaga gagcccagtg cagcaggcag gctctcagac agctcatctg 1680
aagcctctaa gttgagttcc aagagtgcta aggaaagaag aaatcggagg aagaaaagaa 1740

```
aacagaaaga gcagtctggt ggggaagaga aagatgagga tgaattccaa aaatctgaat   1800
ctgaggacag catcaggagg aaaggttttc gcttctccat tgaagggaac cgattgacat   1860
atgaaaagag gtactcctcc ccacaccagt ctttgttgag catccgtggc tccctatttt   1920
caccaaggcg aaatagcaga acaagccttt tcagctttag agggcgagca aaggatgtgg   1980
gatctgagaa cgacttcgca gatgatgagc acagcacctt tgaggataac gagagccgta   2040
gagattcctt gtttgtgccc cgacgacacg gagagagacg caacagcaac ctgagtcaga   2100
ccagtaggtc atcccggatg ctggcagtgt ttccagcgaa tgggaagatg cacagcactg   2160
tggattgcaa tggtgtggtt tccttggttg gtggaccttc agttcctaca tcgcctgttg   2220
gacagcttct gccagaggtg ataatagata agccagctac tgatgacaat ggaacaacca   2280
ctgaaactga aatgagaaag agaaggtcaa gttctttcca cgtttccatg gactttctag   2340
aagatccttc ccaaaggcaa cgagcaatga gtatagccag cattctaaca aatacagtag   2400
aagaacttga agaatccagg cagaaatgcc caccctgttg gtataaattt tccaacatat   2460
tcttaatctg ggactgttct ccatattggt taaaagtgaa acatgttgtc aacctggttg   2520
tgatggaccc atttgttgac ctggccatca ccatctgtat tgtcttaaat actcttttca   2580
tggccatgga gcactatcca atgacggacc atttcaataa tgtgcttaca gtaggaaact   2640
tggttttcac tgggatcttt acagcagaaa tgtttctgaa aattattgcc atggatcctt   2700
actattattt ccaagaaggc tggaatatct ttgacggttt tattgtgacg cttagcctgg   2760
tagaacttgg actcgccaat gtggaaggat tatctgttct ccgttcattt cgattgctgc   2820
gagttttcaa gttggcaaaa tcttggccaa cgttaaatat gctaataaag atcatcggca   2880
attccgtggg ggctctggga aatttaaccc tcgtcttggc catcatcgtc ttcatttttg   2940
ccgtggtcgg catgcagctc tttggtaaaa gctacaaaga ttgtgtctgc aagatcgcca   3000
gtgattgtca actcccacgc tggcacatga atgacttctt ccactccttc ctgattgtgt   3060
tccgcgtgct gtgtggggag tggatagaga ccatgtggga ctgtatggag gttgctggtc   3120
aagccatgtg ccttactgtc ttcatgatgg tcatggtgat tggaaaccta gtggtcctga   3180
atctctttct ggccttgctt ctgagctcat ttagtgcaga caaccttgca gccactgatg   3240
atgataatga aatgaataat ctccaaattg ctgtggatag gatgcacaaa ggagtagctt   3300
atgtgaaaag aaaaatatat gaatttattc aacagtcctt cattaggaaa caaaagattt   3360
tagatgaaat taaaccactt gatgatctaa acaacaagaa agacagttgt atgtccaatc   3420
atacagcaga aattgggaaa gatcttgact atcttaaaga tgtaaatgga actacaagtg   3480
gtataggaac tggcagcagt gttgaaaaat acattattga tgaaagtgat tacatgtcat   3540
tcataaacaa ccccagtctt actgtgactg taccaattgc tgtaggagaa tctgactttg   3600
aaaatttaaa cacggaagac tttagtagtg aatcggatct ggaagaaagc aaagagaaac   3660
tgaatgaaag cagtagctca tcagaaggta gcactgtgga catcggcgca cctgtagaag   3720
aacagcccgt agtggaacct gaagaaactc ttgaaccaga agcttgtttc actgaaggct   3780
gtgtacaaag attcaagtgt tgtcaaatca atgtggaaga aggcagagga aaacaatggt   3840
ggaacctgag aaggacgtgt ttccgaatag ttgaacataa ctggtttgag accttcattg   3900
ttttcatgat tctccttagt agtggtgctc tggcatttga agatatatat attgatcagc   3960
gaaagacgat taagacgatg ttggaatatg ctgacaaggt tttcacttac attttcattc   4020
tggaaatgct tctaaaatgg gtggcatatg gctatcaaac atatttcacc aatgcctggt   4080
gttggctgga cttcttaatt gttgatgttt cattggtcag tttaacagca aatgccttgg   4140
```

-continued

```
gttactcaga acttggagcc atcaaatctc tcaggacact aagagctctg agacctctaa   4200
gagccttatc tcgatttgaa gggatgaggg tggttgtgaa tgccctttta ggagcaattc   4260
catccatcat gaatgtgctt ctggtttgtc ttatattctg gctaattttc agcatcatgg   4320
gcgtaaattt gtttgctggc aaattctacc actgtattaa caccacaact ggtgacaggt   4380
ttgacatcga agacgtgaat aatcatactg attgcctaaa actaatagaa agaaatgaga   4440
ctgctcgatg gaaaaatgtg aaagtaaact ttgataatgt aggatttggg tatctctctt   4500
tgcttcaagt tgccacattc aaaggatgga tggatataat gtatgcagca gttgattcca   4560
gaaatgtgga actccagcct aagtatgaag aaagtctgta catgtatctt tactttgtta   4620
ttttcatcat ctttgggtcc ttcttcacct tgaacctgtt tattggtgtc atcatagata   4680
atttcaacca gcagaaaaag aagtttggag gtcaagacat ctttatgaca gaagaacaga   4740
agaaatacta taatgcaatg aaaaaattag gatcgaaaaa accgcaaaag cctataccte   4800
gaccaggaaa caaatttcaa ggaatggtct ttgacttcgt aaccagacaa gtttttgaca   4860
taagcatcat gattctcatc tgtcttaaca tggtcacaat gatggtggaa acagatgacc   4920
agagtgaata tgtgactacc attttgtcac gcatcaatct ggtgttcatt gtgctattta   4980
ctggagagtg tgtactgaaa ctcatctctc tacgccatta ttattttacc attggatgga   5040
atatttttga ttttgtggtt gtcattctct ccattgtagg tatgtttctt gccgagctga   5100
tagaaaagta tttcgtgtcc cctaccctgt tccgagtgat ccgtcttgct aggattggcc   5160
gaatcctacg tctgatcaaa ggagcaaagg ggatccgcac gctgctcttt gctttgatga   5220
tgtcccttcc tgcgttgttt aacatcggcc tcctactctt cctagtcatg ttcatctacg   5280
ccatctttgg gatgtccaac tttgcctatg ttaagaggga agttgggatc gatgacatgt   5340
tcaactttga gacctttggc aacagcatga tctgcctatt ccaaattaca acctctgctg   5400
gctgggatgg attgctagca cccattctca acagtaagcc acccgactgt gaccctaata   5460
aagttaaccc tggaagctca gttaagggag actgtgggaa cccatctgtt ggaattttct   5520
tttttgtcag ttacatcatc atatccttcc tggttgtggt gaacatgtac atcgcggtca   5580
tcctggagaa cttcagtgtt gctactgaag aaagtgcaga gcctctgagt gaggatgact   5640
ttgagatgtt ctatgaggtt tgggagaagt ttgatcccga tgcaactcag ttcatggaat   5700
ttgaaaaatt atctcagttt gcagctgcgc ttgaaccgcc tctcaatctg ccacaaccaa   5760
acaaactcca gctcattgcc atggatttgc ccatggtgag tggtgaccgg atccactgtc   5820
ttgatatctt atttgctttt acaaagcggg ttctaggaga gagtggagag atggatgctc   5880
tacgaataca gatggaagag cgattcatgg cttccaatcc ttccaaggtc tcctatcagc   5940
caatcactac tactttaaaa cgaaaacaag aggaagtatc tgctgtcatt attcagcgtg   6000
cttacagacg ccacctttta aagcgaactg taaaacaagc ttcctttacg tacaataaaa   6060
acaaaatcaa aggtggggct aatcttctta taaaagaaga catgataatt gacagaataa   6120
atgaaaactc tattacagaa aaaactgatc tgaccatgtc cactgcagct tgtccacctt   6180
cctatgaccg ggtgacaaag ccaattgtgg aaaaacatga gcaagaaggc aaagatgaaa   6240
aagccaaagg gaaataaatg aaaataaata aaaataattg ggtgacaaat tgtttacagc   6300
ctgtgaaggt gatgtatttt tatcaacagg actcctttag gaggtcaatg ccaaactgac   6360
tgtttttaca caaatctcct taaggtcagt gcctacaata agacagtgac cccttgtcag   6420
caaactgtga ctctgtgtaa aggggagatg accttgacag gaggttactg ttctcactac   6480
```

-continued cagctgacac tgctgaagat aagatgcaca atggctagtc agactgtagg gaccagtttc 6540
aaggggtgca aacctgtgat tttggggttg tttaacatga aacactttag tgtagtaatt 6600
gtatccactg tttgcatttc aactgccaca tttgtcacat ttttatggaa tctgttagtg 6660
gattcatctt tttgttaatc catgtgttta ttatatgtga ctatttttgt aaacgaagtt 6720
tctgttgaga aataggctaa ggacctctat aacaggtatg ccacctgggg ggtatggcaa 6780
ccacatggcc ctcccagcta cacaaagtcg tggtttgcat gagggcatgc tgcacttaga 6840
gatcatgcat gagaaaaagt cacaagaaaa acaaattctt aaatttcacc atatttctgg 6900
gaggggtaat tgggtgataa gtggaggtgc tttgttgatc ttgttttgcg aaatccagcc 6960
cctagaccaa gtagattatt tgtgggtagg ccagtaaatc ttagcaggtg caaacttcat 7020
tcaaatgttt ggagtcataa atgttatgtt tctttttgtt gtattaaaaa aaaaacctga 7080
atagtgaata ttgcccctca ccctccaccg ccagaagact gaattgacca aaattactct 7140
ttataaattt ctgcttttc ctgcactttg tttagccatc ttcggctctc agcaaggttg 7200
acactgtata tgttaatgaa atgctattta ttatgtaaat agtcatttta ccctgtggtg 7260
cacgtttgag caaacaaata atgacctaag cacagtattt attgcatcaa atatgtacca 7320
caagaaatgt agagtgcaag ctttacacag gtaataaaat gtattctgta ccatttatag 7380
atagtttgga tgctatcaat gcatgtttat attaccatgc tgctgtatct ggtttctctc 7440
actgctcaga atctcattta tgagaaacca tatgtcagtg gtaaagtcaa ggaaattgtt 7500
caacagatct catttattta agtcattaag caatagtttg cagcacttta acagcttttt 7560
ggttattttt acattttaag tggataacat atggtatata gccagactgt acagacatgt 7620
ttaaaaaaac acactgctta acctattaaa tatgtgttta gaattttata agcaaatata 7680
aatactgtaa aaagtcactt tattttattt ttcagcatta tgtacataaa tatgaagagg 7740
aaattatctt caggttgata tcacaatcac ttttcttact ttctgtccat agtacttttt 7800
catgaaagaa atttgctaaa taagacatga aaacaagact gggtagttgt agatttctgc 7860
tttttaaatt acatttgcta attttagatt atttcacaat tttaaggagc aaaataggtt 7920
cacgattcat atccaaatta tgctttgcaa ttggaaaagg gtttaaaatt ttatttatat 7980
ttctggtagt acctgcacta actgaattga aggtagtgct tatgttattt ttgttctttt 8040
tttctgactt cggtttatgt tttcatttct ttggagtaat gctgctctag attgttctaa 8100
atagaatgtg ggcttcataa tttttttttc cacaaaaaca gagtagtcaa cttatatagt 8160
caattacatc aggacatttt gtgtttctta cagaagcaaa ccataggctc ctcttttcct 8220
taaaactact tagataaact gtattcgtga actgcatgct ggaaaatgct actattatgc 8280
taaataatgc taaccaacat ttaaaatgtg caaaactaat aaagattaca tttttttattt 8340 ta 8342

<210> SEQ ID NO 6
<211> LENGTH: 3806
<212> TYPE: DNA
<213> ORGANISM: Mus musculus

<400> SEQUENCE: 6
gccagtgccg cgcgtcgagc ggagcagagg aggcgagggc ggagggccag agaggcagtt 60
ggaagatggc ggacgaggtg gcgctcgccc ttcaggccgc cggctcccct tccgcggcgg 120
ccgccatgga ggccgcgtcg cagccggcgg acgagccgct ccgcaagagg ccccgccgag 180
acgggcctgg cctcgggcgc agcccgggcg agccgagcgc agcagtggcg ccggcggccg 240

```
cggggtgtga ggcggcgagc gccgcggccc cggcggcgct gtggcgggag gcggcagggg    300
cggcggcgag cgcggagcgg gaggccccgg cgacggccgt ggccggggac ggagacaatg    360
ggtccggcct gcggcgggag ccgagggcgg ctgacgactt cgacgacgac gagggcgagg    420
aggaggacga ggcggcggcg gcagcggcgg cggcagcgat cggctaccga ggtccatata    480
cttttgttca gcaacatctc atgattggca ccgatcctcg aacaattctt aaagatttat    540
taccagaaac aattcctcca cctgagctgg atgatatgac gctgtggcag attgttatta    600
atatcctttc agaaccacca aagcggaaaa aaagaaaaga tatcaataca attgaagatg    660
ctgtgaagtt actgcaggag tgtaaaaaga taatagttct gactggagct ggggtttctg    720
tctcctgtgg gattcctgac ttcagatcaa gagacggtat ctatgctcgc cttgcggtgg    780
acttcccaga cctcccagac cctcaagcca tgtttgatat tgagtatttt agaaaagacc    840
caagaccatt cttcaagttt gcaaaggaaa tatatcccgg acagttccag ccgtctctgt    900
gtcacaaatt catagctttg tcagataagg aaggaaaact acttcgaaat tatactcaaa    960
atatagatac cttggagcag gttgcaggaa tccaaaggat ccttcagtgt catggttcct   1020
ttgcaacagc atcttgcctg atttgtaaat acaaagttga ttgtgaagct gttcgtggag   1080
acatttttaa tcaggtagtt cctcggtgcc ctaggtgccc agctgatgag ccacttgcca   1140
tcatgaagcc agagattgtc ttctttggtg aaaacttacc agaacagttt catagagcca   1200
tgaagtatga caaagatgaa gttgacctcc tcattgttat tggatcttct ctgaaagtga   1260
gaccagtagc actaattcca agttctatac cccatgaagt gcctcaaata ttaataaata   1320
gggaaccttt gcctcatcta cattttgatg tagagctcct tggagactgc gatgttataa   1380
ttaatgagtt gtgtcatagg ctaggtggtg aatatgccaa actttgttgt aaccctgtaa   1440
agctttcaga aattactgaa aaacctccac gcccacaaaa ggaattggtt catttatcag   1500
agttgccacc aacacctctt catatttcgg aagactcaag ttcacctgaa agaactgtac   1560
cacaagactc ttctgtgatt gctacacttg tagaccaagc aacaaacaac aatgttaatg   1620
atttagaagt atctgaatca agttgtgtgg aagaaaaacc acaagaagta cagactagta   1680
ggaatgttga gaacattaat gtggaaaatc cagattttaa ggctgttggt tccagtactg   1740
cagacaaaaa tgaaagaact tcagttgcag aaacagtgag aaaatgctgg cctaatagac   1800
ttgcaaagga gcagattagt aagcggcttg agggtaatca atacctgttt gtaccaccaa   1860
atcgttacat attccacggt gctgaggtat actcagactc tgaagatgac gtcttgtcct   1920
ctagttcctg tggcagtaac agtgacagtg gcacatgcca gagtccaagt ttagaagaac   1980
ccttggaaga tgaaagtgaa attgaagaat tctacaatgg cttggaagat gatacggaga   2040
ggcccgaatg tgctggagga tctggatttg gagctgatgg aggggatcaa gaggttgtta   2100
atgaagctat agctacaaga caggaattga cagatgtaaa ctatccatca gacaaatcat   2160
aacactattg aagctgtccg gattcaggaa ttgctccacc agcattggga actttagcat   2220
gtcaaaaaat gaatgtttac ttgtgaactt gaacaaggaa atctgaaaga tgtattattt   2280
atagactgga aaatagattg tcttcttgga taatttctaa agttccatca tttctgtttg   2340
tacttgtaca ttcaacactg ttggttgact tcatcttcct ttcaaggttc atttgtatga   2400
tacattcgta tgtatgtata attttgtttt ttgcctaatg agtttcaacc ttttaaagtt   2460
ttcaaaagcc attggaatgt taatgtaaag ggaacagctt atctagacca aagaatggta   2520
tttcacactt ttttgtttgt aacattgaat agtttaaagc cctcaatttc tgttctgctg   2580
```

```
aacttttatt tttaggacag ttaacttttt aaacactggc attttccaaa acttgtggca   2640
gctaactttt taaaatcaca gatgacttgt aatgtgagga gtcagcaccg tgtctggagc   2700
actcaaaact tggtgctcag tgtgtgaagc gtacttactg catcgttttt gtacttgctg   2760
cagacgtggt aatgtccaaa caggcccctg agactaatct gataaatgat ttggaaatgt   2820
gtttcagttg ttctagaaac aatagtgcct gtctatatag gtccccttag tttgaatatt   2880
tgccattgtt taattaaata cctatcactg tggtagagcc tgcatagatc ttcaccacaa   2940
atactgccaa gatgtgaata tgcaaagcct ttctgaatct aataatggta cttctactgg   3000
ggagagtgta atattttgga ctgctgtttt tccattaatg aggaaagcaa taggcctctt   3060
aattaaagtc ccaaagtcat aagataaatt gtagctcaac cagaaagtac actgttgcct   3120
gttgaggatt tggtgtaatg tatcccaagg tgttagcctt gtattatgga gatgaataca   3180
gatccaatag tcaaatgaaa ctagttctta gttatttaaa agcttagctt gccttaaaac   3240
tagggatcaa ttttctcaac tgcagaaact tttagccttt caaacagttc acacctcaga   3300
aagtcagtat ttattttaca gacttctttg gaacattgcc cccaaattta aatattcatg   3360
tgggtttagt atttattaca aaaaaatgat ttgaaatata gctgttcttt atgcataaaa   3420
tacccagtta ggaccattac tgccagagga gaaaagtatt aagtagctca tttccctacc   3480
taaaagataa ctgaatttat ttggctacac taaagaatgc agtatattta gttttccatt   3540
tgcatgatgt gtttgtgcta tagacaatat tttaaattga aaaatttgtt ttaaattatt   3600
tttacagtga agactgtttt cagctctttt tatattgtac atagactttt atgtaatctg   3660
gcatatgttt tgtagaccgt ttaatgactg gattatcttc ctccaacttt tgaaatacaa   3720
aaacagtgtt ttatacttgt atcttgtttt aaagtcttat attaaaattg tcatttgact   3780
tttttcccgt taaaaaaaaa aaaaaa                                          3806
```

```
<210> SEQ ID NO 7
<211> LENGTH: 3920
<212> TYPE: DNA
<213> ORGANISM: Mus musculus

<400> SEQUENCE: 7
```

```
agtgccgcgc gtcgagcgga gcagaggagg cgagggcgga gggccagaga ggcagttgga     60
agatggcgga cgaggtggcg ctcgcccttc aggccgccgg ctccccttcc gcggcggccg    120
ccatggaggc cgcgtcgcag ccggcggacg agccgctccg caagaggccc cgccgagacg    180
ggcctggcct cgggcgcagc ccgggcgagc cgagcgcagc agtggcgccg gcggccgcgg    240
ggtgtgaggc ggcgagcgcc gcggccccgg cggcgctgtg gcgggaggcg gcaggggcgg    300
cggcgagcgc ggagcgggag gccccggcga cggccgtggc cggggacgga gacaatgggt    360
ccggcctgcg gcgggagccg agggcggctg acgacttcga cgacgacgag ggcgaggagg    420
aggacgaggc ggcggcggca gcggcggcgg cagcgatcgg ctaccgagac aacctcctgt    480
tgaccgatgg actcctcact aatggctttc attcctgtga aagtgatgac gatgacagaa    540
cgtcacacgc cagctctagt gactggactc cgcggccgcg gataggtcca tatacttttg    600
ttcagcaaca tctcatgatt ggcaccgatc ctcgaacaat tcttaaagat ttattaccag    660
aaacaattcc tccacctgag ctggatgata tgacgctgtg gcagattgtt attaatatcc    720
tttcagaacc accaaagcgg aaaaaaagaa aagatatcaa tacaattgaa gatgctgtga    780
agttactgca ggagtgtaaa aagataatag ttctgactgg agctggggtt tctgtctcct    840
gtgggattcc tgacttcaga tcaagagacg gtatctatgc tcgccttgcg gtggacttcc    900
```

-continued

```
cagacctccc agaccctcaa gccatgtttg atattgagta ttttagaaaa gacccaagac    960
cattcttcaa gtttgcaaag gaaatatatc ccggacagtt ccagccgtct ctgtgtcaca   1020
aattcatagc tttgtcagat aaggaaggaa aactacttcg aaattatact caaaatatag   1080
ataccttgga gcaggttgca ggaatccaaa ggatccttca gtgtcatggt tcctttgcaa   1140
cagcatcttg cctgatttgt aaatacaaag ttgattgtga agctgttcgt ggagacattt   1200
ttaatcaggt agttcctcgg tgccctaggt gcccagctga tgagccactt gccatcatga   1260
agccagagat tgtcttcttt ggtgaaaact taccagaaca gtttcataga gccatgaagt   1320
atgacaaaga tgaagttgac ctcctcattg ttattggatc ttctctgaaa gtgagaccag   1380
tagcactaat tccaagttct ataccccatg aagtgcctca aatattaata aatagggaac   1440
ctttgcctca tctacatttt gatgtagagc tccttggaga ctgcgatgtt ataattaatg   1500
agttgtgtca taggctaggt ggtgaatatg ccaaactttg ttgtaaccct gtaaagcttt   1560
cagaaattac tgaaaaacct ccacgcccac aaaaggaatt ggttcattta tcagagttgc   1620
caccaacacc tcttcatatt tcggaagact caagttcacc tgaaagaact gtaccacaag   1680
actcttctgt gattgctaca cttgtagacc aagcaacaaa caacaatgtt aatgatttag   1740
aagtatctga atcaagttgt gtggaagaaa aaccacaaga agtacagact agtaggaatg   1800
ttgagaacat taatgtggaa aatccagatt ttaaggctgt tggttccagt actgcagaca   1860
aaaatgaaag aacttcagtt gcagaaacag tgagaaaatg ctggcctaat agacttgcaa   1920
aggagcagat tagtaagcgg cttgagggta atcaatacct gtttgtacca ccaaatcgtt   1980
acatattcca cggtgctgag gtatactcag actctgaaga tgacgtcttg tcctctagtt   2040
cctgtggcag taacagtgac agtggcacat gccagagtcc aagtttagaa gaacccttgg   2100
aagatgaaag tgaaattgaa gaattctaca atggcttgga agatgatacg gagaggcccg   2160
aatgtgctgg aggatctgga tttggagctg atggagggga tcaagaggtt gttaatgaag   2220
ctatagctac aagacaggaa ttgacagatg taaactatcc atcagacaaa tcataacact   2280
attgaagctg tccggattca ggaattgctc caccagcatt gggaacttta gcatgtcaaa   2340
aaatgaatgt ttacttgtga acttgaacaa ggaaatctga aagatgtatt atttatagac   2400
tggaaaatag attgtcttct tggataattt ctaaagttcc atcatttctg tttgtacttg   2460
tacattcaac actgttggtt gacttcatct tcctttcaag gttcatttgt atgatacatt   2520
cgtatgtatg tataatttg tttttgcct aatgagtttc aaccttttaa agttttcaaa   2580
agccattgga atgttaatgt aaagggaaca gcttatctag accaaagaat ggtatttcac   2640
acttttttgt ttgtaacatt gaatagttta aagccctcaa tttctgttct gctgaacttt   2700
tatttttagg acagttaact ttttaaacac tggcattttc caaaacttgt ggcagctaac   2760
tttttaaaat cacagatgac ttgtaatgtg aggagtcagc accgtgtctg gagcactcaa   2820
aacttggtgc tcagtgtgtg aagcgtactt actgcatcgt ttttgtactt gctgcagacg   2880
tggtaatgtc caaacaggcc cctgagacta atctgataaa tgatttggaa atgtgtttca   2940
gttgttctag aaacaatagt gcctgtctat ataggtcccc ttagtttgaa tatttgccat   3000
tgtttaatta aatacctatc actgtggtag agcctgcata gatcttcacc acaaatactg   3060
ccaagatgtg aatatgcaaa gcctttctga atctaataat ggtacttcta ctggggagag   3120
tgtaatattt tggactgctg tttttccatt aatgaggaaa gcaataggcc tcttaattaa   3180
agtcccaaag tcataagata aattgtagct caaccagaaa gtacactgtt gcctgttgag   3240
```

-continued

```
gatttggtgt aatgtatccc aaggtgttag ccttgtatta tggagatgaa tacagatcca   3300

atagtcaaat gaaactagtt cttagttatt taaaagctta gcttgcctta aaactaggga   3360

tcaattttct caactgcaga aacttttagc ctttcaaaca gttcacacct cagaaagtca   3420

gtatttattt tacagacttc tttggaacat tgcccccaaa tttaaatatt catgtgggtt   3480

tagtatttat tacaaaaaaa tgatttgaaa tatagctgtt ctttatgcat aaaataccca   3540

gttaggacca ttactgccag aggagaaaag tattaagtag ctcatttccc tacctaaaag   3600

ataactgaat ttatttggct acactaaaga atgcagtata tttagttttc catttgcatg   3660

atgtgtttgt gctatagaca atattttaaa ttgaaaaatt tgttttaaat tatttttaca   3720

gtgaagactg ttttcagctc tttttatatt gtacatagac ttttatgtaa tctggcatat   3780

gttttgtaga ccgtttaatg actggattat cttcctccaa cttttgaaat acaaaaacag   3840

tgttttatac ttgtatcttg ttttaaagtc ttatattaaa attgtcattt gacttttttc   3900

ccgttaaaaa aaaaaaaaaa                                               3920
```

<210> SEQ ID NO 8
<211> LENGTH: 3400
<212> TYPE: DNA
<213> ORGANISM: Mus musculus

<400> SEQUENCE: 8

```
ggagggccag agaggcagtt ggaagatggc ggcggcagcg gcggcggcag cgatcggcta     60

ccgaggtcca tatacttttg ttcagcaaca tctcatgatt ggcaccgatc ctcgaacaat    120

tcttaaagat ttattaccag aaacaattcc tccacctgag ctggatgata tgacgctgtg    180

gcagattgtt attaatatcc tttcagaacc accaaagcgg aaaaaaagaa aagatatcaa    240

tacaattgaa gatgctgtga agttactgca ggagtgtaaa aagataatag ttctgactgg    300

agctggggtt tctgtctcct gtgggattcc tgacttcaga tcaagagacg gtatctatgc    360

tcgccttgcg gtggacttcc cagacctccc agaccctcaa gccatgtttg atattgagta    420

ttttagaaaa gacccaagac cattcttcaa gtttgcaaag gaaatatatc ccggacagtt    480

ccagccgtct ctgtgtcaca aattcatagc tttgtcagat aaggaaggaa aactacttcg    540

aaattatact caaaatatag ataccttgga gcaggttgca ggaatccaaa ggatccttca    600

gtgtcatggt tcctttgcaa cagcatcttg cctgatttgt aaatacaaag ttgattgtga    660

agctgttcgt ggagacattt ttaatcaggt agttcctcgg tgccctaggt gcccagctga    720

tgagccactt gccatcatga agccagagat tgtcttcttt ggtgaaaact taccagaaca    780

gtttcataga gccatgaagt atgacaaaga tgaagttgac ctcctcattg ttattggatc    840

ttctctgaaa gtgagaccag tagcactaat tccaagttct ataccccatg aagtgcctca    900

aatattaata aatagggaac ctttgcctca tctacatttt gatgtagagc tccttggaga    960

ctgcgatgtt ataattaatg agttgtgtca taggctaggt ggtgaatatg ccaaactttg   1020

ttgtaaccct gtaaagcttt cagaaattac tgaaaaacct ccacgcccac aaaaggaatt   1080

ggttcattta tcagagttgc caccaacacc tcttcatatt tcggaagact caagttcacc   1140

tgaaagaact gtaccacaag actcttctgt gattgctaca cttgtagacc aagcaacaaa   1200

caacaatgtt aatgatttag aagtatctga atcaagttgt gtggaagaaa aaccacaaga   1260

agtacagact agtaggaatg ttgagaacat taatgtggaa aatccagatt ttaaggctgt   1320

tggttccagt actgcagaca aaaatgaaag aacttcagtt gcagaaacag tgagaaaatg   1380

ctggcctaat agacttgcaa aggagcagat tagtaagcgg cttgagggta atcaatacct   1440
```

```
gtttgtacca ccaaatcgtt acatattcca cggtgctgag gtatactcag actctgaaga   1500
tgacgtcttg tcctctagtt cctgtggcag taacagtgac agtggcacat gccagagtcc   1560
aagtttagaa gaacccttgg aagatgaaag tgaaattgaa gaattctaca atggcttgga   1620
agatgatacg gagaggcccg aatgtgctgg aggatctgga tttggagctg atggagggga   1680
tcaagaggtt gttaatgaag ctatagctac aagacaggaa ttgacagatg taaactatcc   1740
atcagacaaa tcataacact attgaagctg tccggattca ggaattgctc caccagcatt   1800
gggaacttta gcatgtcaaa aaatgaatgt ttacttgtga acttgaacaa ggaaatctga   1860
aagatgtatt atttatagac tggaaaatag attgtcttct tggataattt ctaaagttcc   1920
atcatttctg tttgtacttg tacattcaac actgttggtt gacttcatct tcctttcaag   1980
gttcatttgt atgatacatt cgtatgtatg tataattttg ttttttgcct aatgagtttc   2040
aaccttttaa agttttcaaa agccattgga atgttaatgt aaagggaaca gcttatctag   2100
accaaagaat ggtatttcac acttttttgt ttgtaacatt gaatagttta aagccctcaa   2160
tttctgttct gctgaacttt tatttttagg acagttaact ttttaaacac tggcattttc   2220
caaaacttgt ggcagctaac tttttaaaat cacagatgac ttgtaatgtg aggagtcagc   2280
accgtgtctg gagcactcaa aacttggtgc tcagtgtgtg aagcgtactt actgcatcgt   2340
ttttgtactt gctgcagacg tggtaatgtc caaacaggcc cctgagacta atctgataaa   2400
tgatttggaa atgtgtttca gttgttctag aaacaatagt gcctgtctat ataggtcccc   2460
ttagtttgaa tatttgccat tgtttaatta aatacctatc actgtggtag agcctgcata   2520
gatcttcacc acaaatactg ccaagatgtg aatatgcaaa gcctttctga atctaataat   2580
ggtacttcta ctggggagag tgtaatattt tggactgctg tttttccatt aatgaggaaa   2640
gcaataggcc tcttaattaa agtcccaaag tcataagata aattgtagct caaccagaaa   2700
gtacactgtt gcctgttgag gatttggtgt aatgtatccc aaggtgttag ccttgtatta   2760
tggagatgaa tacagatcca atagtcaaat gaaactagtt cttagttatt taaaagctta   2820
gcttgcctta aaactaggga tcaattttct caactgcaga aactttttagc ctttcaaaca   2880
gttcacacct cagaaagtca gtatttattt tacagacttc tttggaacat tgcccccaaa   2940
tttaaatatt catgtgggtt tagtatttat tacaaaaaaa tgatttgaaa tatagctgtt   3000
ctttatgcat aaaataccca gttaggacca ttactgccag aggagaaaag tattaagtag   3060
ctcatttccc tacctaaaag ataactgaat ttatttggct acactaaaga atgcagtata   3120
tttagttttc catttgcatg atgtgtttgt gctatagaca atattttaaa ttgaaaaatt   3180
tgttttaaat tatttttaca gtgaagactg ttttcagctc tttttatatt gtacatagac   3240
ttttatgtaa tctggcatat gttttgtaga ccgtttaatg actggattat cttcctccaa   3300
cttttgaaat acaaaaacag tgttttatac ttgtatcttg ttttaaagtc ttatattaaa   3360
attgtcattt gactttttc ccgttaaaaa aaaaaaaaaa                        3400
```

<210> SEQ ID NO 9
<211> LENGTH: 1299
<212> TYPE: DNA
<213> ORGANISM: Mus musculus

<400> SEQUENCE: 9

```
acgcccggga acccccgacc cctctgagcc cggggtactg cgcccgggtc tccacgccca     60
gagatgctcc ccggtctcca ccgtcgggca agccccaagc gcagcagcgc agagtcctgg    120
```

-continued

```
ggtcaccaga gctcgtacta ggacatcgtc tccccattta acaccgcctc cggtcccatc    180
tgagttgcaa gtggtgggga tgtggggctc cggatcaaag tccccgaaac cgagcacttc    240
ccgaagcctc cttggcctcg aaacaaaaca ataacgccca actccatcat attccagaac    300
tcccaccacc tgcatacaga cattcagctg cacaagcccc ctccatgcta cagtcaacag    360
gatctccagg ccacggctca agcccaggta ctcacatcag tggttctatc aacactcagg    420
acagacccat agaagaggcc caagcaggcc ctggaagtgc atgtggaggc caccaggcaa    480
ggaattctgg agtcccaggt actcataact ctgggtggca tggccccttt gcaccatgga    540
ctgtttgccc ttagaaaggg atggatctga gctgggcgca gtggctcatg cctgtaatcc    600
cagcactttg ggaggccaag gtgggcagct cacctcaggt caggttggtc tcaaactcct    660
gacctcaggc gatccacctc agcctctcaa agtgctggaa ttataggtgt gagccactgt    720
gcccagccca aaatcattct ttttggaatt ttgaagcata taattccaaa aggtatgaag    780
gtaatcactt agattgctct aataagggaa tgggaacagt taagtcctat acaaataaga    840
caaagataag atactacaaa aaggggatga gcccaagaaa aaaatcaaag tcccagagag    900
agaacagcca ttgattctaa atacacaagt ctatggcccc aacccaaact tgtttcacta    960
agaacaacct gtggtttcga gaatctggtc atcccccaca gtgaatacat gaacacattg   1020
taatgtttga aatgtttatt tttcttgttg atttcttact gttagaagag ctaagtgatt   1080
tggcccaaag tggctaagtg attcggccag tttgtacaca gggatataag tttgctgaca   1140
ccaagctcat actttacaaa tgtaatatct tcataaaaca aaaatactgg gccgggcgcg   1200
gtggctcacg cctgtaatcc cagcattttg ggaggccgag gcgggcggat catgagatca   1260
ggagatcgag accatcctgg ctagcagggt gaagccccg                          1299
```

<210> SEQ ID NO 10
<211> LENGTH: 720
<212> TYPE: DNA
<213> ORGANISM: Homo sapiens

<400> SEQUENCE: 10

```
agcggggggt tcccgcccgc gcctctccct ccacacctcc ccgcaagcag agggagccgg     60
ctccggcctt ggccagccca gagacaggct cccacagtgc agcggcgggc tgaagggctc    120
ctcaagcact gccagagtgg acaccgaggc cgaggagacg ccaagagcga tgaaacaagc    180
ttctggttca agagtttctt caggttccac tacgggctgt tcttctacag gtgcgccgat    240
gtccacagtg ctaccttctg atgagctact gctttcattc agtttctgct gacttaatat    300
gtgagctgac agaatgcaga gaccacgttg tatatgaagc atccactttg ccttgtacac    360
cagggcattc aataaccact taataactac aaccctgatg atccgattca ctactaaagt    420
cttccgtgtt taaattttca aagtcagatt ctcctacagc aattggtaca gtcacagtaa    480
gactggggtt gtttatgaat gacatgtaat cactttcatc aataatgtat ttttcaacac    540
tgctgccagt tcctatacca cttgtagttc catttacatc tttaagatag tcaagatctt    600
tcccaatttc tgctgtatga ttggacatac aactgtcttt cttgttgttt agatcatcaa    660
gtggtttaat ttcatctaaa atcttttgtt tcctaatgaa ggactgttga ataaattcat    720
```

<210> SEQ ID NO 11
<211> LENGTH: 1123
<212> TYPE: DNA
<213> ORGANISM: Homo sapiens

<400> SEQUENCE: 11

-continued

```
agcggggggt tcccgcccgc gcctctccct ccacacctcc ccgcaagcag agggagccgg      60

ctccggcctt ggccagccca gagacaggct cccacagtgc agcggcgggc tgaagggctc     120

ctcaagcact gccagagtgg acaccgaggc cgaggagacg ccaagagcga tgaaacaagc     180

ttctggttca agagtttctt caggttccac tacgggctgt tcttctacag gtgcgccgat     240

gtccacagtg ctaccttctg atgagctact gctttcattc agtttctgct gacttaatat     300

gtgagctgac agaatgcaga gaccacgttg tatatgaagc atccactttg ccttgtacac     360

cagggcattc aataaccact taataactac aaccctgatg atccgattca ctactaaagt     420

cttccgtgtt taaattttca aagtcagatt ctcctacagc aattggtaca gtcacagtaa     480

gactggggtt gtttatgaat gacatgtaat cactttcatc aataatgtat ttttcaacac     540

tgctgccagt tcctatacca cttgtagttc catttacatc tttaagatag tcaagatctt     600

tcccaatttc tgctgtatga ttggacatac aactgtcttt cttgttgttt agatcatcaa     660

gtggtttaat ttcatctaaa atcttttgtt tcctaatgaa ggactgttga ataaattcat     720

atatttttct tttcacataa gctactcctt tgtgcatcct atccacagca atttggagat     780

tattcatttc attatcatca tcagtggctg caaggttgtc tgcactaaat gagctcagaa     840

gcaaggccag aaagagattc aggaccttaa aaacaacaaa aacatgatta taattttaca     900

ccaatgtagg gaagagcaga ttacaatcac ttattctttc ttttaagtgt ggaaaaaact     960

ctaagttcta aaacttgatg agaaggaaac accacagcat agtgattaga agatgggtga    1020

tctgaatttg tgactggctc aatagcacat ccttggacaa agacatgatt tctgttgctc    1080

tcaagttctc ccattcgtaa agtgaaattg aatgagctaa tct                      1123
```

```
<210> SEQ ID NO 12
<211> LENGTH: 1713
<212> TYPE: DNA
<213> ORGANISM: Mus musculus

<400> SEQUENCE: 12

gggctcccct cagcggcctc tggcgcctcc cgcccgcccg acccgttcgc tcgctcgctc      60

gctcgctcgc ttgctcgtcc gggatcgccg cggtggttca agtttgcgat ggcgccgcca     120

cttcccacct gggcctcacg cgtgcacctt gcctgcctgc gcctcttcgc ctcaagtcgg     180

cttttacctc aggggctctg gagagcccaa cctggccgac gccggccttc ctgaggagaa     240

ctcctccacc tgccttgccc ttgctctgtg acagctcttc ctcaggttac ccctgtggtc     300

tctcctcagg aagtttgcgc tctctcccaa tctcccttct caagtgcaat ggaatgccca     360

agccagccct cggggcctgt tgccctcctg gaaagatctg gcgattgagg acccgcccta     420

tctgctctct ggacccacca ggtcctctgt acctcgcttt agtctttggt aaaattcatc     480

tcttggggca gcaagagaga ggacagaagg gagagtggtt ggttctccac aaacttctgt     540

gttaagagtc agattgggcc tggctcttg tgacttgggc gattgactga accttttcta     600

agcccagttt ttaatcatct ctaaaatgac agggccagga ccgaaagaga ctgtagctca     660

gttgtaaagt cacgcttgcc agacaacccc gaagccctag agagagggag gaaggagggt     720

aagttgaagg taatctccaa ctacttagga agttcaaaaa aggcctggaa tacataagac     780

ctcgtctcaa aaacgaaatt taaaacgata gaccatgaga aatcagctag tcaggtttaa     840

agtaaatgac attagtttta aaatcctagg cagttgatgg tggcacaggc ctttaatccc     900

agcaagctgg aggagacagg aggaggttca ctaggacagc caaggctaca caaagaaacc     960
```

```
ctgtctcgaa aaaataatct tacttctaga attgtagaaa tggctctgta gttaacagca   1020

cttgttgctc ctgcagaggc cctaggtttg actcccatca tccacatgac agctcatacc   1080

ttcagatctg acacctgctt ttggtaaaca cagacatgta tggagccaaa agacccaaac   1140

acataaaaat cctctttgtt gttgttttat gagttagggt ttctctgtgt agccctggct   1200

gtccaggaac tctgtagatc aggctgtcct tgaactcaga ggccacctgc ctctgcttct   1260

tgaactgctg ggattaaaga tgtacaccag caagcccagc ataaaaatac atatttaaat   1320

aatttttaa ataatcctta gttccttcac aactctaagc cccttcactt tctagttacc   1380

atgaaattct gagcacctgt atccatttgg atcattaggg ctcaattgca catggttcaa   1440

ttacagtggg gtttccccag attttagagt tagaggcagc aggatcagaa aattaaatcc   1500

atttgcacta ggtaataaat ttgatcccac cctatctcaa aaacaaaaca ctagccacac   1560

gtggcagcac acacctttta caacaggact caggagcctg gcatgatggg acagaccttt   1620

actccctgca cttgaggcag atgcaggcaa atctaggcat cctggtgtac atatgaagtt   1680

caggcaagcc agggccacgt aggctcaaag acg                                1713


<210> SEQ ID NO 13
<211> LENGTH: 21
<212> TYPE: DNA
<213> ORGANISM: Artificial sequence
<220> FEATURE:
<223> OTHER INFORMATION: Antisense oligonucleotide

<400> SEQUENCE: 13

catgtctcct gcctttcctg t                                               21


<210> SEQ ID NO 14
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 14

ggacagggta gcaacgccat t                                               21


<210> SEQ ID NO 15
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 15

ccacctcagt tgcacggaa                                                  19


<210> SEQ ID NO 16
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 16

ggacagggta gcaacgccau u                                               21


<210> SEQ ID NO 17
<211> LENGTH: 21
<212> TYPE: DNA
<213> ORGANISM: Artificial Sequence
```

<220> FEATURE:
<223> OTHER INFORMATION: Antisense oligonucleotide

<400> SEQUENCE: 17
ggacagggua gcaacgccau u 21

<210> SEQ ID NO 18
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 18
ctgactacct cttga 15

<210> SEQ ID NO 19
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 19
accauggtgc gcgaaauggc a 21

<210> SEQ ID NO 20
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 20
accatggtgc gcgaaatggc a 21

<210> SEQ ID NO 21
<211> LENGTH: 21
<212> TYPE: DNA
<213> ORGANISM: Artificial sequence
<220> FEATURE:
<223> OTHER INFORMATION: Antisense oligonucleotide

<400> SEQUENCE: 21
accauggugc gcgaaauggc a 21

<210> SEQ ID NO 22
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 22
tctctctggg ac 12

<210> SEQ ID NO 23
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 23
ttaccttcat ac 12

<210> SEQ ID NO 24
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 24
aatcacttag ccact 15

<210> SEQ ID NO 25
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 25
gcctcttcta tgggtctguc 20

<210> SEQ ID NO 26
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 26
aaucaauggc ugttctcucu cugggac 27

<210> SEQ ID NO 27
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 27
gtggtatagg aactg 15

<210> SEQ ID NO 28
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 28
gugguauagg aactggcagc a 21

<210> SEQ ID NO 29
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 29
gccagtcaca aautcagauc a 21

<210> SEQ ID NO 30
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 30 acccteccttc ctccc 15

<210> SEQ ID NO 31
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 31
cagaauttca tggua 15

<210> SEQ ID NO 32
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 32
acaggugcuc agaau 15

<210> SEQ ID NO 33
<211> LENGTH: 23
<212> TYPE: DNA
<213> ORGANISM: Artificial Sequence
<220> FEATURE:
<223> OTHER INFORMATION: Antisense oligonucleotide

<400> SEQUENCE: 33
acaggugctc agaauttcau ggu 23

<210> SEQ ID NO 34
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 34
cagaatttca tggta 15

<210> SEQ ID NO 35
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 35
acaggtgctc agaat 15

<210> SEQ ID NO 36
<211> LENGTH: 24
<212> TYPE: DNA
<213> ORGANISM: Artificial Sequence
<220> FEATURE:
<223> OTHER INFORMATION: Antisense oligonucleotide

<400> SEQUENCE: 36
acaggugctc agaatttcau ggua 24

<210> SEQ ID NO 37

-continued

<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 37
acaggtgctc agaat 15

<210> SEQ ID NO 38
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 38
acaggugctc agaat 15

<210> SEQ ID NO 39
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 39
ccacgcgcga gtaca 15

<210> SEQ ID NO 40
<211> LENGTH: 676
<212> TYPE: DNA
<213> ORGANISM: Artificial Sequence
<220> FEATURE:
<223> OTHER INFORMATION: Antisense oligonucleotide

<400> SEQUENCE: 40
caaaatggcg tgctaccctg tccaaccttg tctgtagaca gagtcaattg aacactgtct 60
ttggacttcc gtgcaactga ggtgggcggg cttgaagcac aaagctttca gggagaacca 120
aactttatgc ccaagctgct ctctgccacc cacagggtaa atgaatctca tacaggaaag 180
gcaagagaca tgtgacactg ttgttctgat ggtcacaagt caagcttttt aaaaagcagc 240
ctgatattgt gagctaacat ggctttctgt aattgaatgc aatgtatttt ctatgcttgt 300
ctgggtaaag ttgaccttgg tttgatttag ctcaagcaat atttcaacag tgcactgggg 360
ctctgtcccc tgactactgt ttgactagag ccaggctctg ccctggatgg caaccaacag 420
cccaggctct ggggcacagc cgggctttga caggtctggg gaaatgttca ccggagatga 480
aaggtttcaa actatgaaac tctaaaatct caagtcaaaa cttttgacaa gcacacacag 540
gacatgaatt acaatcaccc gaagattttt acaggcttct caattttaat gacatgctga 600
cacgtgtcat cagatctcac aacaagatga cacatgggtg tcaggtatgg cgcagaagac 660
tagagtcggg gtgtaa 676

ANTAGONAT COMPOSITIONS AND METHODS OF USE

The present application claims the priority of U.S. Provisional Patent Application No. 61/415,307 filed Nov. 18, 2010, and U.S. Provisional Patent Application No. 61/415,858 filed Nov. 21, 2010 which is incorporated herein by reference in its entirety.

FIELD OF THE INVENTION

Embodiments of the invention comprise compositions, compounds, and methods of modulating gene expression.

BACKGROUND OF THE INVENTION

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides, or they can be expressed from endogenous genes as RNA molecules.

SUMMARY OF THE INVENTION

Provided herein are compositions, compounds, and methods of modulating the function of a polynucleotide in a cell. In certain embodiments described herein is a composition, wherein the composition comprises a pharmaceutically acceptable diluent or carrier and an antagoNAT. In some embodiments, the antagoNAT is a modified oligonucleotide that hybridizes with a natural antisense transcript. Certain embodiments of the present invention provide a method for modulating the function of a polynucleotide in a cell comprising contacting the cell with an antagoNAT. In some embodiments, the method includes forming a hybrid comprising the antagoNAT and the polynucleotide, wherein the hybrid sterically blocks the normal function of the polynucleotide.

Some embodiments of the present invention describe a composition comprising a pharmaceutically acceptable diluent or carrier and an antagoNAT, wherein the antagoNAT is 10 to 30 nucleoside subunits in length. In some embodiments, the antagoNAT hybridizes with a preselected natural antisense transcript. In other embodiments, the antagoNAT comprises at least one sugar modified nucleoside subunit at the 3' terminus and at least one sugar modified nucleoside subunit at the 5' terminus. In some embodiments, the antagoNAT further comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal nucleoside is modified. In further or additional embodiments, the antagoNAT comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal modified nucleoside is present between the internal sugar unmodified nucleoside subunits.

In some embodiments, the antagoNAT of a composition described herein comprises sugar modified and sugar unmodified nucleoside subunits, wherein the sugar modified and sugar unmodified nucleoside subunits each comprise a pyrimidine base or purine base. In other embodiments, the internal sugar modified nucleoside subunits each comprise a pyrimidine base or purine base. In further or additional embodiments, the internal sugar modified nucleoside subunits each comprise a pyrimidine base.

In other embodiments, the sugar modified nucleoside subunits are each substituted at the 2' position with alkoxy, alkyl, halogen, amino, thiol, alkylamine, alkylthiol, alkylester, or O-alkylene bound to the C4' carbon. In some embodiments, the sugar modified nucleoside subunits are each substituted at the 2' position with alkoxy, halogen, or O-alkylene bound to the C4' carbon. In specific embodiments, the sugar modified nucleoside subunits are each substituted at the 2' position with methoxy. In certain specific embodiments, the sugar modified nucleoside subunits are each substituted at the 2' position with O-methoxyethyl. In other embodiments of the present invention, the sugar modified nucleoside subunits are each substituted at the 2' position with O-methylene bound to the C4' carbon (2'-$OCH_2$-4') or O-ethylene bound to the C4' carbon (2'-$OCH_2CH_2$-4').

In some preferred compositions of the invention, each unmodified nucleoside subunit independently comprises a ribose or 2'-deoxyribose sugar.

In some embodiments of the composition, the antagoNAT of a composition described herein comprises a backbone of phosphodiester, phosphotriester, phosphorothioate, phosphorodithiate, alkylphosphonate, phosphoramidate, boranophosphate, carbonate, carbamate, acetamidate, thioether, thioformacetal intemucleotide linkages, or combinations thereof. In other embodiments, the antagoNAT comprises a backbone of phosphodiester and phosphorothioate internucleotide linkages. In specific embodiments, the antagoNAT comprises a backbone of phosphorothioate intemucleotide linkages.

In certain embodiments, the antagoNAT of a composition described herein is at least 50% complementary to the preselected natural antisense transcript.

In certain embodiments, the antagoNAT of a composition described herein does not include more than five consecutive internal unmodified nucleosides comprising 2'-deoxyribose sugars, wherein (a) the 3' terminus segment comprises a bicyclic 2'-modified sugar nucleoside and the 5' terminus segment comprises a non-bicyclic 2'-modified sugar nucleoside; or (b) the 3' terminus segment comprises a non-bicyclic 2'-modified sugar nucleoside and the 5' terminus segment comprises a bicyclic 2'-modified sugar nucleoside.

Some embodiments of the present invention describe an antagoNAT of Formula (I), or a salt thereof:

$$C\text{-}A_u\text{-}[B_v\text{-}A'_w]_x\text{-}B_y\text{-}A''_z\text{-}C \qquad \text{Formula (I)}$$

wherein:

each A, A', and A" independently has the structure of:

(Ia)

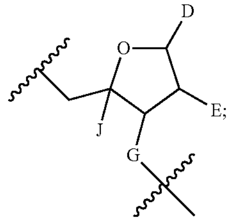

each B independently has the structure of:

(Ib)

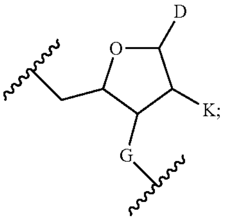

each C is independently hydroxy, phosphate, substituted or unsubstituted alkoxyl, or any suitable 5' or 3' terminus cap;

each u, v, w, x, y and z are independently integers greater than or equal to one;

each D is a heterocyclic base;

each E is independently selected from the group consisting of substituted or unsubstituted alkyl, substituted or unsubstituted alkoxy, substituted or unsubstituted amine, halogen, substituted or unsubstituted aminoalkoxy, substituted or unsubstituted alkenyl, or thiol;

each G is independently $—OP(O)_2O—$, —OP(O)(OR)O—, —OP(O)(S)O—, —OP(O)(SR)O—, $—OP(S)_2O—$, —OP(R)(O)O—, $—OP(NR_2)(O)O—$, —OC(O)O—, $—OCH_2C(O)NHCH_2—$, $—OCH_2S—$, $—CH_2SCH_2—$, $—OP(O)(BH_3)O—$, $—NP(O)_2O—$, —OP(R)(O)O—, or absent when (Ia) is connected to C;

each R is independently hydrogen or substituted or unsubstituted alkyl;

each J is hydrogen or J and E taken together form a ring structure that optionally includes an additional heteroatom selected from N or O; and each K is independently hydroxy or hydrogen.

In certain embodiments of the antagoNAT, each heterocyclic base of the antagoNAT described herein is independently selected from a purine or pyrimidine base. In other embodiments, each heterocyclic base is independently selected from adenine, guanine, uracil, thymine, cytosine, 2-aminoadenine, 5-methylcytosine, 5-bromouracil, or hypoxanthine. In certain specific embodiments, each heterocyclic base is independently selected from adenine, guanine, uracil, thymine, or cytosine. In other specific embodiments, the heterocyclic base of each A' is independently selected from uracil, thymine, or cytosine.

In some embodiments, an antagoNAT is described, wherein each A, A', or A" independently has the structure of:

(Ic)

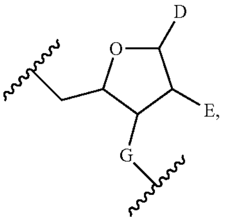

-continued (Id)

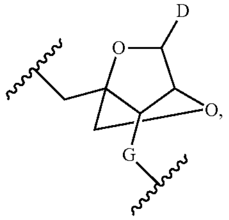

or (Ie)

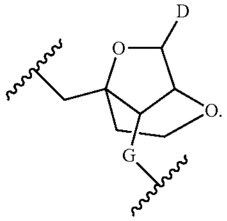

In some preferred compounds of the invention, each E is independently methoxy, ethoxy, O-methylethyl, or fluoro. In specific embodiments, each E is methoxy. In certain specific embodiments, each E is O-methylethyl.

In some embodiments of an antagoNAT described herein, each G is independently $—OP(O)_2O—$, —OP(O)(OR)O—, or —OP(O)(S)O—. In specific embodiments, each G is —OP(O)(S)O—.

In some embodiments of an antagoNAT described herein, each C is hydroxy or any suitable terminus cap structure.

In certain preferred antagoNATs of the invention, v and y are independently integers of 1, 2, or 3 when K is hydroxy and x is at least one. In other embodiments, v and y are independently integers of 1, 2, 3, 4, or 5 when K is hydrogen, and (a) wherein at least one A has the structure of (Id) or (Ie) and at least one A" has the structure of (Ic); or (b) wherein at least one A has the structure of (Ic) and at least one A" has the structure of (Id) or (Ie).

In certain embodiments, provided herein is a method for modulating expression of a gene in a cell. In some embodiments, the method includes contacting the cells with an antagoNAT described herein, wherein the antagoNAT is 10 to 30 nucleoside subunits in length. In some embodiments, the antagoNAT of a composition or used in a method described herein specifically hybridizes with a natural antisense transcript of the gene. In other embodiments, the antagoNAT includes at least one sugar modified nucleoside subunit at the 3' terminus and at least one sugar modified nucleoside subunit at the 5' terminus. In some embodiments, the antagoNAT further comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal nucleoside is modified. In specific embodiments, the antagoNAT additionally includes internal sugar modified nucleoside subunits and internal sugar unmodified nucleoside subunits between the 5' nucleoside subunit and the 3' nucleoside subunit, wherein no more than three internal ribonucleosides are consecutive and at least one internal modified nucleoside is present between the internal sugar unmodified nucleoside subunits.

In some embodiments, any method of modulating gene expression described herein further comprises forming a hybrid comprising the antagoNAT and the natural antisense transcript; thereby modulating the expression of said gene.

In some embodiments, any method of modulating gene expression described herein further comprises forming a hybrid comprising the antagoNAT and the natural antisense transcript, wherein the hybrid is not a substrate for ribonuclease cleavage. In certain embodiments, the method comprises sterically blocking the normal function of the natural antisense transcript. In some embodiments, the antagoNAT has at least 50% sequence identity to a complement of the natural antisense transcript. In other embodiments, expression of the gene is up-regulated in the cell with respect to a control. In certain embodiments, expression of the gene is down-regulated in the cell with respect to a control.

In some embodiments, the type of cell contacted with an antagoNAT according to a method described herein is a mammalian cell.

Further in accordance with certain embodiments of the present invention, there is provided a method of modulating function of a polynucleotide in a cell comprising contacting the cell with an antagoNAT. In some embodiments, the antagoNAT is 10 to 30 nucleoside subunits in length. In other embodiments, the antagoNAT hybridizes with the polynucleotide. In specific embodiments, the antagoNAT comprises at least one sugar modified nucleoside subunit at the 3' terminus and at least one sugar modified nucleoside subunit at the 5' terminus. In some embodiments, the antagoNAT further comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal nucleoside is modified. In further or additional embodiments, the antagoNAT comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal modified nucleoside is present between the internal sugar unmodified nucleoside subunits.

In some embodiments, the targeted polynucleotide according to a method described herein is a natural antisense strand to a sense strand. In certain embodiments, the antagoNAT has at least 50% sequence identity to a complement of the polynucleotide.

In some embodiments, any method of modulating function of a polynucleotide described herein further comprises forming a hybrid comprising the antagoNAT and the polynucleotide; thereby modulating said function of said polynucleotide. In certain embodiments, the hybrid is not a substrate for ribonuclease cleavage. In some embodiments, the method comprises sterically blocking the normal function of the polynucleotide. In certain embodiments, expression of the sense strand is elevated in the cell with respect to a control. In other embodiments, expression of the sense strand is decreased in the cell with respect to a control.

In some embodiments, the type of cell contacted with an antagoNAT according to a method described herein is a mammalian cell.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying figures of which:

FIG. 1—cDNA Sequence of BF133827 (SEQ ID NO: 40), a potential non-coding antisense transcript for mouse ABCA1. Specific target sites are highlighted.

FIG. 2—RT-PCR analysis of macrophage ABCA1 mRNA expression at 48 hours following treatment with ABCA1-AS antisense oligonucleotides (50 nM, n=3). Values represent mean±SEM. * indicates statistical significance compared to CUR586 control ($p<0.05$; 1-way ANOVA; n=3).

FIG. 3*a*—Western immunoblot analysis of macrophage ABCA1 protein expression at 48 hours following treatment with ABCA1-AS antisense oligonucleotides (50 nM, n=3), using ABCA1 primary polyclonal antibody (Novus).

FIG. 3*b*—Densitometric analysis of the macrophage Western immunoblot. Values represent mean±SEM. * indicates statistical significance compared to CUR586 control ($p<0.05$; 1-way ANOVA; n=3).

Figure 4:
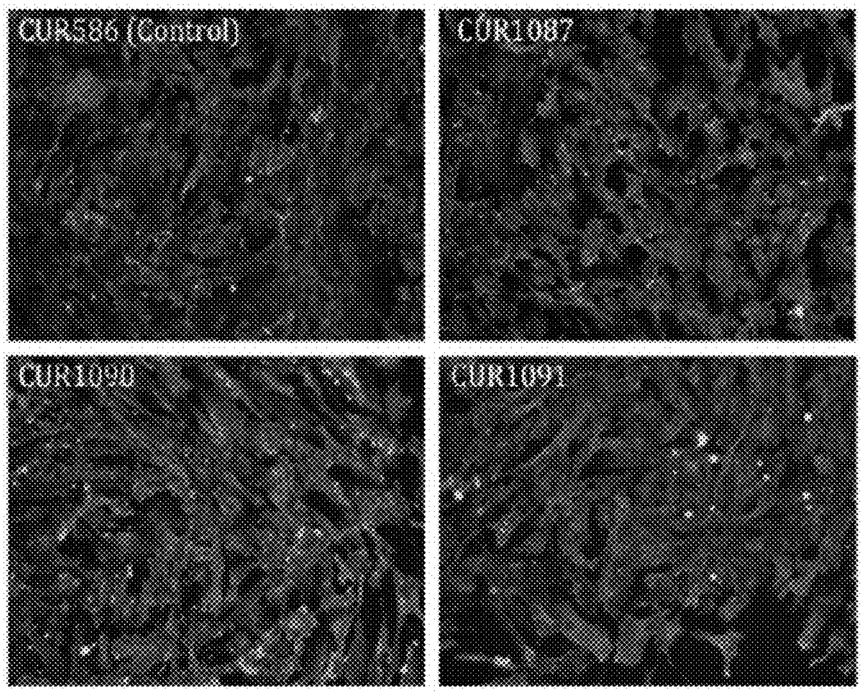
FIG. 4—Immunostaining of macrophage ABCA1 protein at 48 hours following treatment with ABCA1-AS antisense oligonucleotides (50 nM). Nuceli were stained with Hoechst 33258 while ABCA1 was visualized using an Alexa Fluor 488-conjugated secondary antibody.

Sequence Listing Description—SEQ ID NO: 1: *Homo sapiens* ATP-binding cassette, sub-family A (ABC1), member 1(ABCA1), mRNA (NCBI Accession No.: NM_005502); SEQ ID NO: 2: *Homo sapiens* sodium channel, voltage-gated, type I, alpha subunit (SCN1A), transcript variant 1, mRNA (NCBI Accession No.: NM_001165963); SEQ ID NO: 3: *Homo sapiens* sodium channel, voltage-gated, type I, alpha subunit (SCN1A), transcript variant 2, mRNA (NCBI Accession No.: NM_006920); SEQ ID NO: 4: *Homo sapiens* sodium channel, voltage-gated, type I, alpha subunit (SCN1A), transcript variant 3 mRNA (NCBI Accession No.: NM_001165964); SEQ ID NO: 5: *Homo sapiens* sodium channel, voltage-gated, type I, alpha subunit (SCN1A), transcript variant 4, mRNA (NCBI Accession No.: NM_001202435); SEQ ID NO: 6: *Mus musculus* sirtuin 1 (silent mating type information regulation 2, homolog) 1 (*S. cerevisiae*) (Sirt1), transcript variant 2, mRNA (NCBI Accession Number: NM_001159589); SEQ ID NO: 7 *Mus musculus* sirtuin 1 (silent mating type information regulation 2, homolog) 1 (*S. cerevisiae*) (Sirt1), transcript variant 1, mRNA (NCBI Accession Number: NM_019812); SEQ ID NO: 8 *Mus musculus* sirtuin 1 (silent mating type information regulation 2, homolog) 1 (*S. cerevisiae*) (Sirt1), transcript variant 3, mRNA (NCBI Accession Number: NM_001159590); SEQ ID NO: 9: Mouse Natural ABCA1 antisense sequence (AK311445); SEQ ID NO: 10 and 11: Natural SCN1A antisense sequence, original and extended respectively (BG724147); SEQ ID NO: 12: Mouse Natural SIRT1 antisense sequence (ak044604); SEQ ID NOs: 13 to 21: Sequences of 2'-Unmodified and 2'-Modified ABCA1-AS Antisense Oligonucleotides; SEQ ID NOs: 22 to 26: Sequences of AntagoNAT and Control Oligonucleotides Targeted to ABCA1-AS Antisense Oligonucleotides; SEQ ID NOs: 27 to 29: Sequences of Chemically Modified Oligonucleotides Targeted to SCN1A-AS Antisense Oligonucleotide; SEQ ID NOs: 30 to 39: Sequences of Chemically Modified Oligonucleotides Targeted to SIRT1 Antisense Oligonucleotide. * indicates phosphorothioate bond, +indicates 2'-bicyclic sugar modified nucleoside or LNA, and m indicates 2'-O-Methyl sugar modified nucleoside.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Certain Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "nucleoside" or "nucleoside subunit" means a glycosylamine comprising a nucleobase and a sugar. Nucleosides include, but are not limited to, natural nucleosides, abasic nucleosides, modified nucleosides, and nucleosides having mimetic bases and/or sugar groups.

As used herein, the term "unmodified nucleoside" or "natural nucleoside" means a nucleoside comprising a natural nucleobase and a natural sugar. Natural nucleosides include ribonucleic acid (RNA) and deoxyribonucleic acid (DNA) nucleosides.

As used herein, the term "unmodified sugar" or "sugar unmodified" refers to a sugar of a nucleoside that is unmodified from its naturally occurring form in RNA (2'-OH) or DNA (2'-H).

As used herein, the term "modified sugar", "2'-modified sugar" or "sugar unmodified" refers to a pentofuranosyl sugar of a nucleoside comprising a substituent at the 2' position other than H or OH. 2'-modified sugars include, but are not limited to, pentofuranosyl sugar substituted at the 2' position with alkoxy, alkyl, halogen, amino, thiol, alkylamine, alkylthiol, alkylester, or O-alkylene bound to the C4' carbon.

As used herein, the term "nucleobase" refers to the base portion of a nucleoside or nucleotide. A nucleobase may comprise any atom or group of atoms capable of hydrogen bonding to a base of another nucleic acid.

As used herein, the term "unmodified nucleobase" refers to a nucleobase that is unmodified from its naturally occurring form in RNA or DNA.

As used herein, the term "heterocyclic base" refers to a nucleobase comprising a heterocycle.

As used herein, the term "nucleotide" or "nucleotide subunit" refers to a nucleoside having a phosphate group covalently linked to the sugar. Nucleotides may be modified with any of a variety of substituents.

As used herein, "internucleoside linkage" refers to a covalent linkage between adjacent nucleosides.

As used herein, "natural internucleotide linkage" refers to a 3' to 5' phosphodiester linkage.

As used herein, the term "modified internucleoside linkage" refers to any linkage between nucleosides or nucleotides other than a naturally occurring internucleoside linkage.

The term "oligomeric compound" is meant to be inclusive of the terms oligonucleotides and oligonucleosides, either used singly or in combination, as well as other oligomeric compounds including chimeric compounds formed.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

In the context of this invention, "chimeric" compounds are oligonucleotides, which contain two or more chemical regions, for example, DNA region(s), RNA region(s), modified nucleotide regions, etc. Each chemical region is made up of at least one subunit, i.e., a nucleotide in the case of an oligonucleotide. These oligonucleotides typically comprise at least one region wherein the oligonucleotide is modified in order to exhibit one or more desired properties. The desired properties of the oligonucleotide include, but are not limited, for example, increased resistance to nuclease degradation, increased cellular uptake, reduced toxicity effects, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

As used herein, the term "antagoNAT" refers to a polymeric structure comprising two or more nucleoside structures and capable of hybridizing to a region of a nucleic acid molecule. In some embodiments, antagoNATs are chemically engineered oligonucleotides that are complementary to specific natural antisense molecules, wherein the oligonucleotides comprise sugar unmodified nucleoside subunits and sugar modified nucleoside subunits. In other embodiments, the antagoNAT includes at least one sugar modified nucleoside subunit at the 3' terminus and at least one sugar modified nucleoside subunit at the 5' terminus. In some embodiments, the antagoNAT further comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal nucleoside is modified. In some embodiments, the antagoNAT additionally includes internal sugar modified nucleoside subunits and internal sugar unmodified nucleoside subunits between the 5' nucleoside subunit and the 3' nucleoside subunit, wherein no more than three internal ribonucleosides are consecutive and at least one internal modified nucleoside is present between the internal sugar unmodified nucleoside subunits. In some embodiments, the antagoNAT hybridizes with a natural antisense transcript of a sense strand. In certain embodiments, antagoNATs are antisense oligonucleotides. In some embodiments, the specific hybridization of an antagoNAT and the target nucleic acid molecule interferes with the normal function of the nucleic acid molecule. In specific embodiments, the product of hybridization of a certain antagoNAT with the target molecule is not a substrate for ribonuclease cleavage. Oligomeric double-stranded compounds can be two strands hybridized to form double-stranded compounds or a single strand with sufficient self complementarity to allow for hybridization and formation of a fully or partially double-stranded compound.

As used herein, the term "mixed-backbone antagoNAT" refers to an antagoNAT wherein a least one internucleoside linkage of the antagoNAT is different from at least one other internucleotide linkage of the antagoNAT.

As used herein, the term "terminus segment", refers to a consecutive sequence of modified sugar nucleoside subunits at the 3' terminus and/or the 5' terminus of a chemically modified oligonucleotide.

As used herein, the term "antisense compound" or "antisense molecule" or "antisense transcript" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these. Such molecules include, for example, antisense RNA or DNA molecules, interference RNA (RNAi), micro RNA, decoy RNA molecules, short interfering RNA (siRNA), enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds. While all antisense compounds are oligomeric compounds, not all oligomeric compounds are antisense compounds.

As used herein, the term "antisense oligonucleotide" refers to an antisense compound that is an oligonucleotide.

As used herein, the term "natural antisense transcript" refers to an oligomeric compound encoded within a cell that is at least partially complementary to other RNA transcripts and/or other endogenous sense transcripts. In certain embodiments, the natural antisense transcript does not code for a protein. In certain embodiments, the natural antisense transcript contains a stop codon early in the transcript that prevents significant protein coding.

As used herein, the term "antisense activity" refers to any detectable and/or measurable activity attributable to the hybridization of an antisense compound to its target nucleic acid. Such detection and or measuring may be direct or indirect. For example, in certain embodiments, antisense activity is assessed by detecting and or measuring the amount of target protein. In certain embodiments, antisense activity is assessed by detecting and/or measuring the amount of target nucleic acids.

As used herein, the term "detecting antisense activity" or "measuring antisense activity" means that a test for detecting or measuring antisense activity is performed on a sample and compared to that of a control sample. Such detection and/or measuring may include values of zero.

As used herein, the term "control sample" refers to a sample that has not been contacted with a test compound. In certain embodiments, a control sample is obtained prior to administration of an oligomeric compound to an animal. In certain embodiments, a control sample is obtained from an animal to which oligomeric compound is not administered. In certain embodiments, a reference standard is used as a surrogate for a control sample.

As used herein, the term "mock treated sample" refers to a sample that has not been contacted with a test compound. In certain embodiments, a mock treated sample is a control sample comprising liquid vehicle. In certain embodiments, a mock treated sample is a control sample comprising aqueous vehicle. In specific embodiments, a mock treated sample is a control sample comprising saline, water, or buffered solutions.

As used herein, the term "motif" refers to a pattern of unmodified and modified nucleotides or linkages in an oligomeric compound.

As used herein the term "target gene" refers to a gene encoding a target.

As used herein the term targeting or "targeted to" refers to the association of an antisense compound to a particular target nucleic acid molecule or a particular region of nucleotides within a target nucleic acid molecule.

As used herein, the term "oligonucleotide specific for" or "oligonucleotide which targets" refers to an oligonucleotide having a sequence (i) capable of forming a stable complex with a portion of the targeted nucleic acid molecule, or (ii) capable of forming a stable duplex with a portion of an RNA transcript and/or natural antisense transcript of the targeted gene. Stability of the complexes and duplexes can be determined by theoretical calculations and/or in vitro assays.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

As used herein, the term "percent complementary" refers to the number of nucleobases of an oligomeric compound that have nucleobases complementarity with a corresponding nucleobase of another oligomeric compound or nucleic acid divided by the total length (number of nucleobases) of the oligomeric compound.

As used herein, the term "modulation" refers to a perturbation of function or activity when compared to the level of function or activity when compared to the level of the function or activity prior to modulation. For example, modulation includes the change, either an increase (stimulation or induction) or a decrease (inhibition or reduction) in gene expression. Modulation also includes up-regulation (stimulation or induction) or down-regulation (inhibition or reduction) of gene expression.

As used herein, the term “expression” refers to all the functions and steps by which a gene’s coded information is converted into structures present and operating in a cell. Such structures include, but are not limited to the products of transcription and translation.

Further in the context of this invention, “hybridization” refers to hydrogen bonding, which may be Watson-Crick, Hoögsteen or reversed Hoögsteen hydrogen bonding, between complementary nucleobases.

“Complementary” as used herein, refers to the capacity for precise pairing between two nucleobases. For example, adenine and thymine are complementary nucleobases which pair through the formation of hydrogen bonds.

The terms “complementary” and “specifically hybridizable” as used herein, refer to precise pairing or sequence complementarity between a first and a second nucleic acid-like oligomers containing nucleoside subunits. For example, if a nucleobase at certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, “specifically hybridizable” and “complementary” are terms which are used to indicate a sufficient degree of complementarity such that stable and specific binding occurs between a compound of the invention and a target nucleic acid molecule. It is understood that an oligomeric compound of the invention need not be 100% complementary to its target nucleic acid sequence to be specifically hybridizable. An oligomeric compound is specifically hybridizable when binding of the oligomeric compound to the target antisense molecule interferes with the normal function of the target antisense molecule to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of vitro assays, under conditions in which the assays are performed.

As used herein, the term “side effects” refers to physiological responses attributable to a treatment other than desired effects. In certain embodiments, side effects include, without limitation, liver function test abnormalities, injections site reactions, renal function abnormalities, liver toxicity, renal toxicity, central nervous system abnormalities, and myopathies.

As used herein, the term “SIRT1” refers to Silencing mating type information regulator 2 homolog and is a member of the SIRTuin deacetylase protein family. The amino acid sequence of SIRT1 may be found at Genbank Accession number NP.sub.-08509. SIRT1 is the human homolog of the yeast Sir2 protein and exhibits NAD-dependent deacetylase activity.

As used herein, the term “ABCA1” refers ATP-binding cassette transporter A1 (ABCA1) and is an integral membrane protein that exports cholesterol from cells and initiates the formation of mature HDL by facilitating apolipoprotein A-I (apoA-I) lipidation.

As used herein, the term “SCN1” refers sodium channel, voltage-gated, type I, alpha subunit.

The term “alkyl” as used herein refers to saturated or unsaturated, straight- or branched-chain hydrocarbon radicals derived from a hydrocarbon moiety containing between one and twenty carbon atoms by removal of a single hydrogen atom. Alkyl groups as used herein may optionally include one or more further substituent groups.

The term “halo” and “halogen” as used herein refer to an atom selected from fluorine, chlorine, bromine and iodine.

The term “cycloalkyl” as used herein refers to a monovalent group derived from a monocyclic or bicyclic saturated carbocyclic ring compound containing between three and twenty carbon atoms by removal of a single hydrogen atom. Cycloalkyl groups as used herein may optionally include one or more further substituent groups.

The alkyl group or cycloalkyl group may optionally be substituted by one or more of fluorine, chlorine, bromine, iodine, carboxyl, alkoxycarbonyl, alkylaminocarbonyl, di-(alkyl)-aminocarbonyl, hydroxyl, alkoxy, formyloxy, alkylcarbonyloxy, alkylthio, cycloalkyl or phenyl.

The term “aminoalkyl” as used herein, refers to an amino substituted alkyl radical. This term is meant to include alkyl groups having an amino substituent at any position and wherein the alkyl group attaches the aminoalkyl group to the parent molecule. The alkyl and/or amino portions of the aminoalkyl group can be further substituted with substituent groups.

As used herein, the term “alkoxy” refers to a radical formed between an alkyl group and an oxygen atom wherein the oxygen atom is used to attach the alkoxy group to a parent molecule. Alkoxy groups as used herein may optionally include further substituent groups.

As used herein, the term “alkenyl” refers to a straight or branched hydrocarbon chain radical containing up to twenty four carbon atoms and having at least one carbon-carbon double bond. Alkenyl groups as used herein may optionally include one or more further substituent groups.

As used herein, the term “aryl” refers to a mono- or polycyclic carbocyclic ring system radicals having one or more aromatic rings. Examples of aryl groups include, but are not limited to, phenyl, naphthly, tetrahydronaphthyl, tetrahydronaphthyl, indanyl, idenyl and the like. Aryl groups as used herein may optionally include further substituent groups.

As used herein, the term “acyl” refers to a radical formed by removal of a hydroxyl group from an organic acid and has the general formula —C(O)—X where X is typically aliphatic, acyclic or aromatic. Acyl groups may optionally include further substituent groups.

As used herein, the terms “substituent” and “substituent group” refer to groups that are typically added to other groups or parent compounds to enhance desired properties or give desired effects. Substituent groups can be protected or unprotected and can be added to one available sites in a parent compound. Substituent groups may also be further substituted with other substituent groups and may be attached directly or via a linking group such as an alkyl group to a parent compound.

2'-OH and 2'-H are utilized as an abbreviation for unmodified sugars, i.e. pentoribofuranosyl and pentodeoxyribofuranosyl sugars. For modified nucleosides, the abbreviations used are: 2'-O-alkyl for general alkyl groups at the 2' position of a pentofuranosyl structure. (e.g., with a specific alkyl being noted as 2'-OMe for methyl).

As used herein, the term “bicyclic nucleoside” refers to a nucleoside wherein the furanose portion of the nucleosides includes a bridge connection two atoms on the furanose ring, thereby forming a bicyclic ring system.

As used herein, the term “LNA” or “locked nucleic acid” refers to the a nucleoside wherein the 2' hydroxyl group of a ribosyl sugar ring is linked to the 4' carbon of the sugar ring, thereby forming a bicyclic nucleoside.

As used herein, the term "substituted at 2' position with O-methylene bound to the C4' carbon" refers to a bicyclic nucleoside wherein the bridge connecting the two atoms of the furanose ring bridges the 4' carbon atom and the 2' carbon atom of the furanose ring, thereby forming a bicyclic ring system.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. For example, S. M. Berge, et al. describes pharmaceutically acceptable salts in detail in J. Pharmaceutical Sciences, 66: 1-19 (1977), incorporated herein by reference for this purpose. The salts are prepared in situ during the final isolation and purification of the compounds described herein, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "cap structure" or "terminal cap structure" refers to chemical modifications, which have been incorporated at either terminus of an antisense compound.

As used herein, the term "analogs" refers to nucleotides includes synthetic nucleotides having modified base moieties and/or modified sugar moieties (see e.g., described generally by Scheit, Nucleotide Analogs, John Wiley, New York, 1980; Freier & Altmann, (1997) Nucl. Acid. Res., 25(22), 4429-4443, Toulme, J. J., (2001) Nature Biotechnology 19:17-18; Manoharan M., (1999) Biochemica et Biophysica Acta 1489:117-139; Freier S. M., (1997) Nucleic Acid Research, 25:4429-4443, Uhlman, E., (2000) Drug Discovery & Development, 3: 203-213, Herdewin P., (2000) Antisense & Nucleic Acid Drug Dev., 10:297-310); 2'-O, 3'-C-linked [3.2.0]bicycloarabinonucleosides (see e.g. N. K Christiensen., et al, (1998) J. Am. Chem. Soc., 120: 5458-5463; Prakash T P, Bhat B. (2007) Curr Top Med Chem. 7(7):641-9; Eun Jeong Cho, Joo-Woon Lee, Andrew D. Ellington Applications of Aptamers as Sensors Annual Review of Analytical Chemistry, July 2009, Vol. 2, Pages 241-264. Such analogs include synthetic nucleotides designed to enhance binding properties, e.g., duplex or triplex stability, specificity, or the like.

As used herein, the term "mammal" covers warm blooded mammals that are typically under medical care (e.g., humans and domesticated animals). Examples include feline, canine, equine, bovine, and human, as well as just human.

Overview

In certain embodiments, chemical modifications improve the potency and/or efficacy of antisense compounds, decreasing toxicological effects, decreasing the potential for side effects. In certain embodiments, antagoNATs comprising certain chemical modifications are less toxic than other oligomeric compounds comprising different modifications. Chemical modifications can alter oligonucleotide activity by, for example: increasing affinity of an antisense oligonucleotide for its target nucleic acid molecule, increasing nuclease resistance, altering the pharmacokinetics of the oligonucleotide and/or reducing toxicological effects.

Identifying a Natural Antisense Transcript

Some embodiments of the present invention describe an antagoNAT that targets a natural antisense transcript. In some embodiments, a scan of known gene databases, such as Genebank, is carried out to identify any potential naturally occurring antisense transcript. Certain scanning processes yield a non-coding RNA transcript within the intergenic region of a certain gene. In some embodiments, sequence identification and subsequent screening are used to identify single-stranded antisense oligonucleotides that inhibit expression of the certain gene.

Certain AntagoNATs

In certain embodiments, the antagoNAT of a composition described herein is an oligonucleotide that hybridizes with a natural antisense transcript. Certain oligonucleotides comprise modified nucleosides, unmodified nucleosides, and modified internucleoside linkages.

The compounds described herein according to some embodiments of this invention include one or more asymmetric center(s) and this gives rise to enantiomers, diastereomers, and other stereoisomeric configurations. The present invention includes all the enantiomers and diastereomers as well as mixtures thereof in any proportions. The invention also extends to isolated enantiomers or pairs of enantiomers. Methods of separating enantiomers and diastereomers are well known to persons skilled in the art.

Some embodiments of the present invention describe a composition comprising a pharmaceutically acceptable diluent or carrier and an antagoNAT, wherein the antagoNAT is 10 to 50 nucleoside subunits in length. In some embodiments, the antagoNAT is 10 to 45 nucleoside subunits in length, or 10 to 40 nucleoside subunits in length, or 10 to 35 nucleoside subunits in length, or 15 to 30 nucleoside subunits in length. In other embodiments, the antagoNAT is 18 to 30 nucleoside subunits in length. In other embodiments, the antagoNAT is 20 to 30 nucleoside subunits in length. In other embodiments, the antagoNAT is 25 to 30 nucleoside subunits in length. In other embodiments, the antagoNAT is 10 to 20 nucleoside subunits in length.

In other embodiments, the antagoNAT comprises at least one sugar modified nucleoside subunit at the 3' terminus and at least one sugar modified nucleoside subunit at the 5' terminus. In some embodiments, the antagoNAT further comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal nucleoside is modified. In further or additional embodiments, the antagoNAT comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal modified nucleoside is present between internal sugar unmodified nucleoside subunits. In some embodiments, the antagoNAT comprises an unmodified sugar nucleoside subunit at the 3' terminus or an unmodified sugar nucleoside subunit at the 5' terminus. In other embodiments, the antagoNAT comprises an unmodified sugar nucleoside subunit at the 3' terminus and an unmodified sugar nucleoside subunit at the 5' terminus. In other embodiments, the antagoNAT comprises a modified sugar nucleoside subunit at the 3' terminus and an unmodified sugar nucleoside subunit at the 5' terminus. In other embodiments, the antagoNAT comprises an unmodified sugar nucleoside subunit at the 3' terminus and a modified sugar nucleoside subunit at the 5' terminus.

In certain embodiments of the composition, there are no more than five internal unmodified nucleosides comprising 2'-deoxyribose sugars are consecutive, wherein (a) the 3' terminus segment comprises a bicyclic 2'-modified sugar nucleoside and the 5' terminus segment comprises a non-bicyclic 2'-modified sugar nucleoside; or (b) the 3' terminus segment comprises a non-bicyclic 2'-modified sugar nucleoside and the 5' terminus segment comprises a bicyclic 2'-modified sugar nucleoside.

In some embodiments, the composition comprises sugar modified and sugar unmodified nucleoside subunits, wherein the sugar modified and sugar unmodified nucleoside subunits each comprise a pyrimidine base or purine base. In other embodiments, the internal sugar modified nucleoside subunits each comprise a pyrimidine base or purine base. In further or additional embodiments, the internal sugar modified nucleoside subunits each comprise a pyrimidine base. Natural or unmodified bases or heterocyclic bases include the purine bases adenine (A), and guanine (G), and the pyrimidine nucleobases thymine (T), cytosine (C), and uracil (U). Many modified nucleobases or nucleobase mimetics known to those skilled in the art are amenable with the compounds described herein. In addition, modified nucleobases or heterocyclic bases are optionally included such as 7-deazapurine, 5-methylcytosine, 2-aminoadenine, 5-bromouracil, or hypoxanthine. In specific embodiments, the internal sugar modified nucleoside subunits each independently comprise a pyrimidine base selected from uracil, thymine, or cytosine.

Any composition described herein comprises sugar modified nucleoside subunits that are substituted at the 2' position with alkoxy, alkyl, halogen, amino, thiol, alkylamine, alkylthiol, alkylester, O-alkylene bound to the C4' carbon, or combinations thereof. Many modified sugar nucleosides known to those skilled in the art are amenable with the compounds described herein. In some embodiments, the sugar modified nucleoside subunits are each substituted at the 2' position with alkoxy, halogen, or O-alkylene bound to the C4' carbon. Suitable substituents at the 2' position include but are not limited to methoxy, fluoro, O-methoxyethyl, O-methylene bound to the C4' carbon (2'-$OCH_2$-4'), or O-ethylene bound to the C4' carbon (2'-$OCH_2CH_2$-4'). In other embodiments, modified sugar subunits comprises one of the following at the 2' position: OH; F; O-, S-, or N-alkyl; O-, S-, or N-alkenyl; O-, S-or N-alkynyl; or O alkyl-O-alkyl, wherein the alkyl, alkenyl and alkynyl may be substituted or unsubstituted C to CO alkyl or C2 to CO alkenyl and alkynyl. Particularly preferred are $-O(CH_2)_nOCH_3$, $-O[(CH_2)_nO]_mCH_3$, $-O(CH_2)_nNH_2$, $-O(CH_2)_nCH_3$, $-O(CH_2)_nONH_2$, and $-O([(CH_2)_nON(CH_2)_nCH_3)_2$ where n and m can be from 1 to about 10. Other oligonucleotides comprise one of the following at the 2' position: C to CO, (lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514, 785; 5,519,134; 5,567,811; 5,576,427; 5,591,722; 5,597,909; 5,610,300; 5,627,053; 5,639,873; 5,646, 265; 5,658,873; 5,670,633; and 5,700,920, each of which is herein incorporated by reference.

Any composition described herein comprises unmodified nucleoside subunit, wherein the sugar of the nucleoside is a ribose or 2'-deoxyribose sugar. In certain embodiments, the unmodified nucleoside subunits comprise ribose sugars. In other embodiments, the unmodified nucleoside subunits comprise 2'-deoxyribose sugars. In specific embodiments, the unmodified nucleoside subunits comprise ribose and 2'-deoxyribose sugars.

Any composition described herein comprises a backbone of phosphodiester, phosphotriester, phosphorothioate, phosphorodithiate, alkylphosphonate, phosphoramidate, boranophosphate, carbonate, carbamate, acetamidate, thioether, thioformacetal internucleotide linkages, or combinations thereof. In other embodiments, the antagoNAT comprises a backbone of phosphodiester and phosphorothioate internucleotide linkages. In specific embodiments, the antagoNAT comprises a backbone of phosphorothioate internucleotide linkages.

Some embodiments of the present invention describe an antagoNAT of Formula (I), or a salt thereof:

$$C\text{-}A_u\text{-}[B_v\text{-}A'_w]_x\text{-}B_y\text{-}A''_z\text{-}C \qquad \text{Formula (I)}$$

wherein:

each A, A', and A" independently has the structure of:

(Ia)

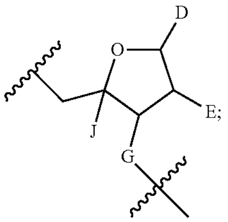

each B independently has the structure of:

(Ib)

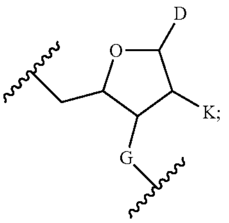

each C is independently hydroxy, phosphate, substituted or unsubstituted alkoxy, or any suitable 5' or 3' terminus cap;

each u, v, w, x, y and z are independently integers greater than or equal to one;

each D is a heterocyclic base;

each E is independently selected from the group consisting of substituted or unsubstituted alkyl, substituted or unsubstituted alkoxy, substituted or unsubstituted amine, halogen, substituted or unsubstituted aminoalkoxy, substituted or unsubstituted alkenyl, or thiol;

each G is independently $—OP(O)_2O—$, —OP(O)(OR)O—, —OP(O)(S)O—, —OP(O)(SR)O—, $—OP(S)_2O—$, —OP(R)(O)O—, $—OP(NR_2)(O)O—$, —OC(O)O—, $—OCH_2C(O)NHCH_2—$, $—OCH_2S—$, $—CH_2SCH_2—$, $—OP(O)(BH_3)O—$, $—NP(O)_2O—$, —OP(R)(O)O—, or absent when (Ia) is connected to C;

each R is independently hydrogen or substituted or unsubstituted alkyl;

each J is hydrogen or J and E taken together form a ring structure that optionally includes an additional heteroatom selected from N or O; and each K is independently hydroxy or hydrogen.

In some embodiments, any antagoNAT described herein comprises a heterocyclic base that is independently selected from a purine or pyrimidine base. In other embodiments, each heterocyclic base is independently selected from adenine, guanine, uracil, thymine, cytosine, 7-deazapurine, 2-aminoadenine, 5-methylcytosine, 5-bromouracil, or hypoxanthine. In certain specific embodiments, each heterocyclic base is independently selected from adenine, guanine, uracil, thymine, or cytosine. In other specific embodiments, the heterocyclic base of each A' is independently selected from uracil, thymine, or cytosine.

In some embodiments, an antagoNAT is described, wherein each A, A', or A" independently has the structure of:

(Ic)

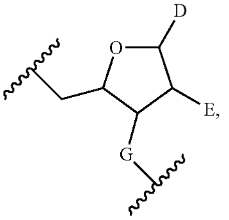

-continued (Id)

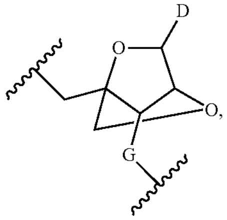

or (Ic)

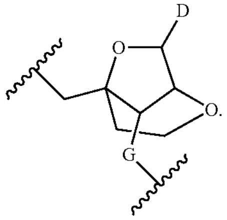

In some preferred compounds of the invention, each E is independently methoxy, ethoxy, O-methylethyl, or fluoro. In specific embodiments, each E is methoxy. In certain specific embodiments, each E is O-methylethyl.

In some preferred antagoNATs of the invention, each G is independently $—OP(O)_2O—$, —OP(O)(OR)O—, or —OP(O)(S)O—. In specific embodiments, each G is —OP(O)(S)O—. In other embodiments, G is a combination of $—OP(O)_2O—$ and —OP(O)(S)O—.

In some preferred antagoNATs of the invention, each C is hydroxy or a suitable terminus cap structure.

In certain preferred antagoNATs of the invention, v and y are independently integers of 1, 2, or 3 when K is hydroxy and x is at least one. In other embodiments, v and y are independently integers of 1, 2, 3, 4, or 5 when K is hydrogen, and (a) wherein at least one A has the structure of (Id) or (Ie) and at least one A" has the structure of (Ic); or (b) wherein at least one A has the structure of (Ic) and at least one A" has the structure of (Id) or (Ie).

Complementarity

It is understood in the art that incorporation of nucleotide affinity modification may allow for a greater number of mismatches compared to an unmodified compound. Similarly, antagoNAT sequences may be more tolerant to mismatches than other oligonucleotide sequences. In some embodiments, the antagoNAT hybridizes with a natural antisense transcript of a gene.

Any antagoNAT or compound described herein is at least about 50% complementary to the preselected natural antisense transcript. In certain embodiments, the antagoNATs of the present invention comprise at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence complementarity to a target region within the target nucleic acid sequence to which they are targeted. For example, an antagoNAT in which 18 of 20 nucleotides of the compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antagoNAT which is 18 nucleotides in length having four noncomplementary nucleotides which are flanked by two regions of complete complementarity with the target nucleic acid molecule would have 77.8% overall complementarity with the target nucleic acid molecule and would thus fall within the scope of the present invention. Percent complementarity of an antagoNAT with a region of a target nucleic acid molecule can be determined routinely using BLAST programs (basic local alignment search tools) and PowerBLAST programs known in the art (Altschul et al., (1990) J. Mol. Biol., 215, 403-410; Zhang and Madden, (1997) Genome Res., 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., (1981) 2, 482-489).

Selection of appropriate target nucleic acid molecules is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of target nucleic acid molecules that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

Methods

In certain embodiments of the present invention, provided herein is a method for modulating expression of a gene in a cell. In some embodiments, the method includes contacting the cells with an antagoNAT, wherein the antagoNAT is 10 to 30 nucleoside subunits in length. In some embodiments, the antagoNAT specifically hybridizes with a natural antisense transcript of the gene. In other embodiments, the antagoNAT includes at least one sugar modified nucleoside subunit at the 3' terminus and at least one sugar modified nucleoside subunit at the 5' terminus. In some embodiments, the antagoNAT further comprises internal sugar modified nucleoside subunits and internal sugar unmodified nucleoside subunits between the 5' nucleoside subunit and the 3' nucleoside subunit, wherein no more than three internal ribonucleosides are consecutive and at least one internal nucleoside is modified. In some embodiments, the antagoNAT additionally includes internal sugar modified nucleoside subunits and internal sugar unmodified nucleoside subunits between the 5' nucleoside subunit and the 3' nucleoside subunit, wherein no more than three internal ribonucleosides are consecutive and at least one internal modified nucleoside is present between internal sugar unmodified nucleoside subunits.

In some embodiments, any method of modulating gene expression described herein further comprises forming a hybrid comprising the antagoNAT and the natural antisense transcript, wherein the hybrid is not a substrate for ribonuclease cleavage. In certain embodiments, the method comprises sterically blocking the normal function of the natural antisense transcript, thereby modulating the function of the gene. In certain embodiments, the antagoNATs of the present invention comprise at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence complementarity to the natural antisense transcript. In other embodiments, expression of the gene is up-regulated in the cell with respect to a control cell. In certain embodiments, expression of the gene is down-regulated in the cell with respect to a control cell.

In some embodiments, the type of cell contacted with an antagoNAT according to a method described herein is a mammalian cell.

Further in accordance with certain embodiments of the present invention, there is provided a method of modulating function of a polynucleotide in a cell comprising contacting the cell with an antagoNAT. In some embodiments, the antagoNAT is 10 to 30 nucleoside subunits in length. In other embodiments, the antagoNAT hybridizes with the polynucleotide. In specific embodiments, the antagoNAT comprises at least one sugar modified nucleoside subunit at the 3' terminus and at least one sugar modified nucleoside subunit at the 5' terminus. In further or additional embodiments, the antagoNAT comprises internal sugar modified nucleoside subunits and internal sugar unmodified nucleoside subunits between the 5' nucleoside subunit and the 3' nucleoside subunit, wherein no more than three internal nucleosides comprising ribose sugars are consecutive and at least one internal modified nucleoside is present between the internal sugar unmodified nucleoside subunits.

In some embodiments, the polynucleotide targeted according to a method described herein is a natural antisense strand to a sense strand. In certain embodiments, the antagoNATs of the present invention comprise at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence complementarity to the polynucleotide.

In some embodiments, any method of modulating function of a polynucleotide described herein further comprises forming a hybrid comprising the antagoNAT and the polynucleotide, thereby modulating said function of said polynucleotide. In certain embodiments, the resultant hybrid is not a substrate for ribonuclease cleavage.

In some embodiments, the method comprises sterically blocking the normal function of the polynucleotide. In certain embodiments, expression of the sense strand is elevated in the cell with respect to a control. In other embodiments, expression of the sense strand is decreased in the cell with respect to a control.

In some embodiments, the type of cell contacted with an antagoNAT according to a method described herein is a mammalian cell.

The regulation of gene expression by targeting a natural antisense transcript has been described, e.g., in U. S. Pat. App. Pub. No. 2009/0258925, "Natural Antisense and Non-coding RNA Transcripts as Drug Targets", incorporated herein by reference in its entirety. This publication reports targeting natural antisense transcripts to up-regulate and down-regulate sense transcripts, which can be coding or noncoding. Natural antisense targeting is also described in, e.g.: U. S. Pat. App. Pub. No. 2010/0105760, "Treatment of Apolipoprotein-A1 Related Diseases by Inhibition of Natural Antisense Transcript to Apolipoprotein-A1"; WO 2010/065671, "Treatment of Vascular Endothelial Growth Factor (VEGF) Related Diseases by Inhibition of Natural Antisense Transcript to VEGF"; WO 2010/065662, "Treatment of Sirtuin 1 (SIRT1) Related Disease by Inhibition of Natural Antisense Transcript to Sirtuin 1"; WO 2010/102058, "Treatment of Sirtuin 1 (SIRT1) Related Disease by Inhibition of Natural Antisense Transcript to Sirtuin 1"; WO 2010/065792, "Treatment of Erythropoietin (EPO) Related Diseases by Inhibition of Natural Antisense Transcript to EPO"; WO 2010/065787, "Treatment of Tumor Suppressor Gene Related Diseases by Inhibition of Natural Antisense Transcript to the Gene"; WO 2010/093904, "Treatment of Brain Derived Neurotrophic Factor (BDNF) Related Diseases by Inhibition of Natural Antisense Transcript to BDNF", and; WO 2010/093906 GDNF, "Treatment of Glial Cell Derived Neurotrophic Factor (GDNF) Related Diseases by Inhibition of Natural Antisense Transcript to GDNF", all incorporated herein by reference.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

General

The sequences listed in the examples have been annotated to indicate the location and type of nucleoside and internucleoside linkage modifications. All the nucleosides that are not annotated in the examples are β-D-deoxyribonucleosides. Each modified nucleoside is preceded by a letter or symbol. In particular, "m" indicates a 2'-O-methyl group and "+" indicates a LNA or bicyclic nucleoside. The symbol "*" indicates a phosphorothioate internucleoside linkage.

Materials

RAW264.7 macrophage cells were purchased from ATCC and cultured in an Eagle Minimum Essential Medium supplemented with 10% FBS and 5% penicillin/streptomycin. Primary astrocytes were purchased from Sciencell Research Laboratories and cultured in Sciencell Astrocyte medium supplemented with 5% FBS and 2% astrocyte growth medium. HepG2 cells were grown in EMEM (ATCC cat #2003)+10% FBS. NIH 3T3 cells from ATCC were grown in DMEM (Mediatech cat#10-0 1 3-CV)+10% FCS (Mediatech cat #35-022-CV). 518A2 cells were grown in DMEM+5% FBS.

Small scale batches of antagoNATs for screening were manufactured by IDT Inc. (Coralville, Iowa). The oligonucleotides were applied to cells seeded in 6 well plates dropwise in OptiMEM+Lipofectamine mixture at the final concentration of 20 nM unless noted otherwise. After about 18 h incubation the media was replaced and the incubation continued for another 18-24 h when the cells were harvested for RNA isolation.

Example 1: Amidites for Oligonucleotide/Oligonucleoside Synthesis

2'-O-Methyl nucleoside amidites and 2'-OH nucleoside amidites are available from Glen Research, Sterling, Va. Other 2'-O-alkyl substituted nucleoside amidites are prepared as is described in U.S. Pat. Nos. 5,506,351, 5,466,786, or 5,514,786, herein incorporated by reference.

Example 2: Synthesis of 2'-O-Methyl Nucleoside Amidites i. 2'-O-Methyl-5-methyluridine 2,2'-anhydro-5-methyluridine (10.0 g, 0.0416 mol) is dissolved in methanol (80 mL) in a stainless steel bomb (100 mL capacity). Trimethyl borate is generated by adding solutions (1 M in THF) of borane to methanol and allowing the resulting hydrogen gas to evolve. Trimethyl borate (5.6 mL, 0.049 mol) is added. The bomb is sealed and placed in an oil bath at 150° C. which generates pressure. After 40 h, the bomb is cooled in ice, opened and the contents concentrated under reduced pressure.

ii. 5'-O-Dimethoxytriphenylmethyl-2'-O-methyl-5-methyluridine

2'-O-methyl-5-methyluridine (12 g) is co-evaporated in pyridine (2×50 mL) and dissolved in dry pyridine (50 mL). Dimethoxytriphenylmethyl chloride (18.1 g, 0.054 mol) is added. The flask is covered and allowed to stand for 45 min at room temperature. The reaction mixture is treated with methanol (10 mL) and the resultant solution is concentrated under reduced pressure. The residue is partitioned between ethyl acetate (2×400 mL) and saturated sodium bicarbonate solution (500 mL). The organic layers are combined, dried (sodium sulfate), filtered and concentrated.

Example 3: Synthesis of Oligonucleotide

Unsubstituted and substituted phosphodiester oligoribonucleotides are synthesized on an automated DNA synthesizer using standard phosphoramidite chemistry with oxidation by iodine.

Phosphorothioate oligonucleotides are synthesized as per the phosphodiester oligonucleotides except the standard oxidation reagent is replaced by 0.2 M solution of 3H-1,2-benzodithiole-3-one-1,1,-dioxide in acetonitrile for the stepwise thiation of the phosphite linkage. The thiation wait step is increased to 68 seconds and is followed by the capping step. After cleavage from the column and deblocking in concentrated ammonium hydroxide at 55° C. (18 h), the oligonucleotides are purified by precipitating twice with 2.5 volumes of ethanol from a 0.5 M NaCl solution. Analytical gel electrophoresis is accomplished in 20% acrylamide, 8 M urea, 454 mM Tris-borate buffer, pH 7.

Example 4: Chimeric Phosphorothioate Oligonucleotides

Chimeric oligoribonucleotides having 2'-O-alkyl phophorothioate and 2'-H phosphorothioate oligonucleotide segments are synthesized using an automated DNA synthesizer. Oligonucleotides are synthesized using the automated synthesizer and 5'-dimethoxytrityl-3'-O-phosphoramidite for the unmodified subunits and 5'-dimethoxytrityl-2'-O-methyl-3'-O-phosphoramidite for the 3' terminus and 5' terminus in addition to internal modified subunits. The standard synthesis cycle is modified by increasing the wait step after the delivery of tetrazole and base. The protecting groups on the exocyclic amines are phenoxyacetyl for adenine and guanine, benzoyl for cytosine, 2'-O-methyl adenine, and 2'-O-methyl cytosine, and isobutyryl for 2'-O-methyl guanine. The fully protected oligonucleotide is cleaved from the support and the phosphate group is deprotected in 3:1 ammonia/ethanol at room temperature overnight then lyophilized to dryness. Addition of methanolic ammonia at room temperature affords deprotected bases. The resultant is lyophilized to dryness and desalted on a size exclusion column.

Chimeric oligoribonucleotides having 2'-O-alkyl phophorothioate and 2'-OH phosphorothioate oligonucleotide segments are synthesized using an automated DNA synthesizer. Oligonucleotides are synthesized using the automated synthesizer and 5'-dimethoxytrityl-2'-tert-butyldimethylsilyl-3'-O-phosphoramidite for the unmodified subunits and 5'-dimethoxytrityl-2'-O-methyl-3'-O-phosphoramidite for the 3' terminus and 5' terminus in addition to internal modified subunits. The standard synthesis cycle is modified. The protecting groups on the exocyclic amines are phenoxyacetyl for adenine and guanine, benzoyl for cytosine, 2'-O-methyl adenine, and 2'-O-methyl cytosine, and isobutyryl for 2'-O-methyl guanine. The fully protected oligonucleotide is cleaved from the support and the phosphate group is deprotected in 3:1 ammonia/ethanol at room temperature overnight then lyophilized to dryness. Addition of methanolic ammonia at room temperature affords deprotected bases. Treatment with 1M TBAF in THF for 24 hours at room temperature deprotects the 2'-OH groups. The resultant is lyophilized to dryness and desalted on a size exclusion column.

Example 5: Identifying a Natural Antisense Transcript for ABCA1

In order to identify any potential naturally occurring ABCA1 antisense transcripts, a scan of known gene databases, such as UCSC genome browser and Genebank, was carried out. This yielded a non-coding RNA transcript, approximately 1 Kb in length, within the intergenic region of the ABCA1 gene, which was shown to be transcribed in the opposite, 5' to 3' direction (BF133827). Based on this sequence and subsequent, three single-stranded antisense oligonucleotides were demonstrated to be particularly effective in inhibiting expression of this transcript. The BF133827 sequence, containing the specific areas targeted by these antisense oligonucleotides, is presented in FIG. 1.

Example 6: In Vitro Screening of Antisense Oligonucleotides Targeting ABCA1 Antisense Transcript The effects of antisense oligonucleotides on ABCA1 expression were examined using a RAW264.7 mouse leukaemic macrophage cell line. FIG. 2 depicts the relative expression levels of ABCA1 mRNA observed 48 hours after transfection with each antisense oligonucleotide (50 nM). Of the three active antisense oligonucleotide sequences tested, quantitative RT-PCR analysis revealed a substantial increase of ABCA1 mRNA expression in cells transfected with both CUR1090 and CUR1091, compared to those treated with the control oligonucleotide (CUR586), with the most significant effect observed for CUR1090 (p=0.0004; 1-way ANOVA; n=4). To examine whether this up-regulation of mRNA expression translated to a corresponding increase in ABCA1 protein levels within these cells, western blot analysis was next carried out. After 48 hours following transfection with each antisense oligonucleotide, total cell protein was separated using SDS-PAGE and probed with a commercially available ABCA1 polyclonal antibody. This analysis revealed a band at the expected molecular weight of 220 kDa (FIG. 3*a*). Densitometric analysis confirmed a three-fold increase of ABCA1 expression in cells treated with CUR1090 compared to those treated with CUR586 (p=0.0024; 1-way ANOVA; n=3) (FIG. 3*b*).

Real-Time PCR Analysis of ABCA1 mRNA Expression

Total RNA was extracted from cell and tissue samples using Qiagen RNeasy columns. cDNA was prepared from 800 ng of Dnase-treated RNA using a Taqman Reverse Transcription Kit (Applied Biosystems). cDNA from each sample was amplified using a Taqman gene expression assay for mouse ABCA1 (Applied Biosystems, CA, USA). The relative differences between Ct values for ABCA1 and a reference gene (18s RNA) were calculated as ΔΔCt. All real-time PCR was carried out using the 7900HT Fast Real-Time PCR System (Applied Biosystems, CA, USA).

Sodium Dodecyl Sulphate-Polyacrylamide Gel Electrophoresis and Immunoblotting

Whole-cell and tissue protein was extracted using M-PER protein extraction reagent (Thermo Scientific) and total protein concentrations were determined for each sample using a BCA Protein Assay Kit (Pierce). Protein samples of equal concentrations were separated on a polyacrylamide Criterion gel and electrophoretically transferred to PVDF membranes. The PVDF membrane was blocked using 5% milk, diluted in 1× Tris.-Buffered Saline (containing 2 mM Tris, 500 nM sodium chloride, pH 7.5) for 1 h at room temperature and incubated overnight at 4° C. with a polyclonal rabbit anti-ABCA1 primary antibody (Novus), diluted 1:1000 in blocking buffer. The next day, the PVDF membrane was incubated for 1 h at room temperature with an anti-rabbit, horseradish peroxidase-linked secondary antibody (Cell Signalling), diluted 1:2000 in blocking buffer washed with TBS-T buffer. Protein bands were visualized using chemiluminescence peroxidase substrate and exposed to X-ray film. The X-ray films were scanned and quantitative densitometry of the electrophoretic bands was performed. PVDF membranes were also probed with a primary mouse anti-actin antibody. ABCA1 protein expression was determined by dividing ABCA1 densitometry values by those obtained for the actin loading control.

Example 7: Immunohistochemical Analysis of Macrophage ABCA1 Protein

To further characterize the increase in ABCA1 expression, the cellular distribution of ABCA1 was analyzed using immunohistochemistry. Oligonucleotide-treated RAW264.7 cells were fixed 48 hours after transfection and incubated overnight with a primary ABCA1 polyclonal antibody followed by an Alexa Fluor 488-conjugated secondary antibody. FIG. 4 demonstrates the relative expression levels of ABCA1 in cells treated with each sequence. As can be seen, a significant increase in fluorescent activity was detected in cells transfected with CUR1090, compared with control. Furthermore, in line with its important cellular function, the majority of this ABCA1 expression was evident close to or along the macrophage cell membrane.

Immunostaining of ABCA1 in RAW264.7 Cells

At 48 hours post-transfection, cells were fixed in culture with paraformaldehyde (4%) for 20 minutes, followed by 2-3 washes in PBS. The cells were then permeabilized with ethanol (95):acetic acid (5) for 20 minutes at −20° C., followed by 2-3 washes in PBS (5% FBS). A polyclonal rabbit anti-ABCA1 primary antibody (Novus), diluted 1:1000 in PBS (5% FBS), was added and samples were maintained overnight at 4° C. The next day, cell samples were blocked with PBS (5% FBS) for 20 minutes, followed by a 40 minute incubation at room temperature with an Alexa Fluor 488-conjugated secondary antibody. Following 2-3 washes with PBS, the coverslip was mounted using aqueous mounting medium, containing antifade. Nuclear staining was carried out using Hoechst blue, diluted in PBS (5% FBS). Fluorescence was analyzed by con-focal microscopy.

Figure 5:
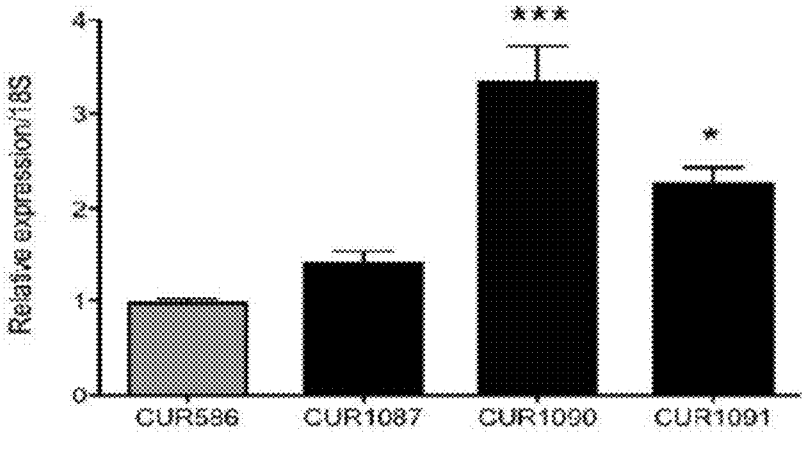
FIG. 5—RT-PCR analysis of astrocyte ABCA1 mRNA expression following treatment with ABCA1-AS antisense oligonucleotides (50 nM, n=3).
Figure 6A:
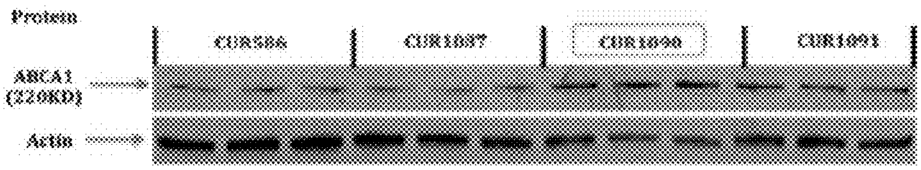
FIG. 6*a*—Western immunoblot analysis of astrocyte ABCA1 protein expression following treatment with ABCA1-AS antisense oligonucleotides (50 nM, n=3), using ABCA1 primary polyclonal antibody.
Figure 6B:
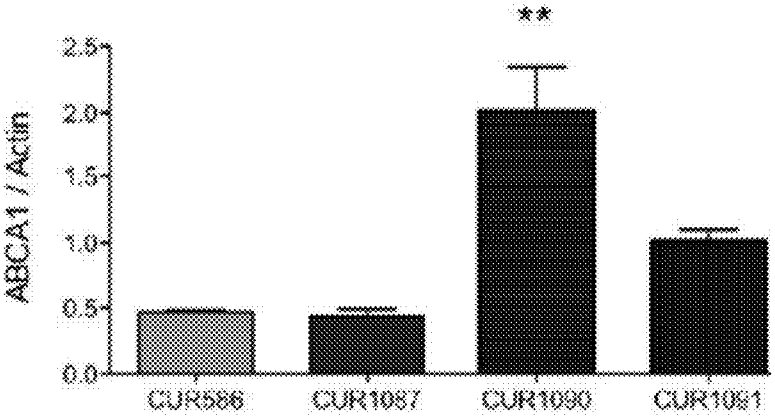
FIG. 6*b*—Densitometric analysis of the astrocyte Western immunoblot following treatment with ABCA1-AS antisense oligonucleotides (50 nM, n=3). Values represent mean±SEM. * indicates statistical significance compared to CUR586 control ($p<0.05$; 1-way ANOVA; n=3).

Example 8: In Vitro Screening of Antisense Oligonucleotides Targeting ABCA1 Antisense Transcript The effects of antisense oligonucleotides on ABCA1 expression were assessed using primary astrocytes. As can be seen in FIG. 5, quantitative real-time PCR analysis demonstrated a statistically significant up-regulation of ABCA1 mRNA expression in primary astrocytes transfected with CUR 1090 and CUR1091 compared to those treated with the control oligonucleotide (p=0.0003; 1-way ANOVA; n=3). A three-fold increase in ABCA1 transcription was observed for cells treated with CUR1090. In addition, western blot analysis confirmed a corresponding four-fold increase in protein levels within these cells (p=0.0007; 1-way ANOVA; n=3) (FIGS. 6*a* and 6*b*).

Example 9: AntagoNATs Targeting ABCA1 Antisense Transcript

Figure 8:
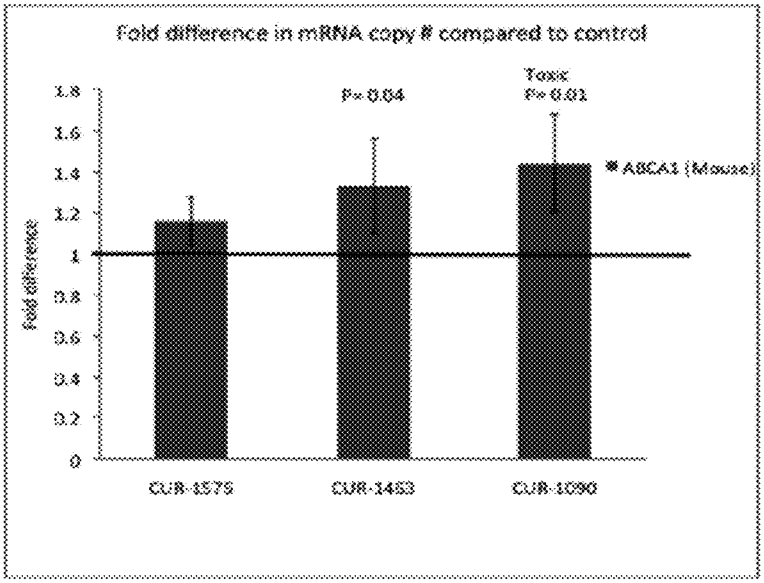
FIG. 8—RT-PCR Analysis of ABCA1 mRNA levels in mouse NIH 3T3 cells following treatment with AntagoNAT CUR1463.

CUR1090 was selected for further chemical modification. Two different 2'-O-methyl modified versions of CUR1090, based on CURNA's antagoNAT construct were synthesized, and tested in macrophage RAW264.7 cells. The sequences of these modified oligonucleotides are presented in Table 1. As control samples, RAW264.7 cells were also transfected with scrambled versions of both the original and modified active oligonucleotides (CUR 1461 and CUR1575).

levels in mouse NIH 3T3 cells compared to scrambled sequence control sample as assessed by RT-PCR analysis (FIG. 8). The antagoNAT CUR1463 with additional 2'-O-methyl modifications showed much lower toxicity than the same oligonucleotide sequence with phosphorothioate backbone modifications (CUR-1090).

Figure 9:
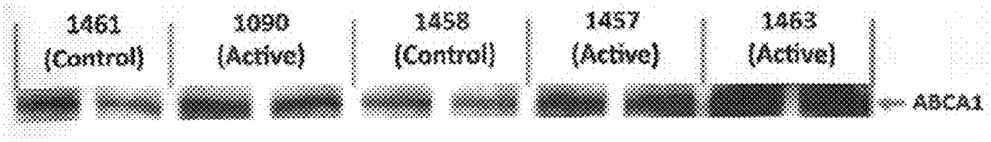
FIG. 9—Western Immunoblot Analysis of ABCA1 protein levels in mouse NIH 3T3 cells following treatment with AntagoNAT CUR1463.

Treatment of mouse NIH 3T3 cells with CUR1090, CUR1457 and CUR1463 led to an increase in ABCA1 protein levels relative to the two scrambled sequence control samples as assessed by Western immunoblot analysis (FIG. 9). The antagoNAT CUR1463 with internal sugar 2'-O-methyl modifications shows a greater increase in ABCA1 protein than CUR1457 which have 2'-O-methyl modifications only on each end.

Example 12: In-Vivo Testing of Active Antisense Oligonucleotide CUR1463 on ABCA1 Expression In Vivo Administration of ABCA1-AS Antisense Oligonucleotides In vivo studies were carried out using adult, four-month-old male C57BL6 mice. CUR1463 and CUR1575 were

TABLE 1

| Sequence ID | Sequence Name | Sequence |
|---|---|---|
| Sequences of 2'-Unmodified and 2'-Modified ABCA1-AS Antisense Oligonucleotides | | |
| SEQ ID NO: 13 | CUR-1087 | C*A*T*G*T*C*T*C*C*T*G*C*C*T*T*T*C*C*T*G*T |
| SEQ ID NO: 14 | CUR-1090 | G*G*A*C*A*G*G*G*T*A*G*C*A*A*C*G*C*C*A*T*T |
| SEQ ID NO: 15 | CUR-1091 | C*C*A*C*C*T*C*A*G*T*T*G*C*A*C*G*G*A*A |
| Chemically Modified Oligonucleotide Sequences | | |
| SEQ ID NO: 16 | CUR-1457 | mG*mG*mA*mC*mA*G*G*G*T*A*G*C*A*A*C*G*mC*mC*mA*mU*mU |
| SEQ ID NO: 17 | CUR-1463 | mG*mG*mA*C*A*G*G*G*mU*A*G*mC*A*A*mC*G*mC*C*mA*mU*mU |
| Control Oligonucleotide Sequences | | |
| SEQ ID NO: 18 | CUR-586 | C*T*G*A*C*T* A*C*C*T*C*T*T*G*A |
| SEQ ID NO: 19 | CUR-1458 | mA*mC*mC*mA*mU*G*G*T*G*C*G*C*G*A*A*A*mU*mG*mG*mC*mA |
| SEQ ID NO: 20 | CUR-1461 | A*C*C*A*T*G*G*T*G*C*G*C*G*A*A*A*T*G*G*C*A |
| SEQ ID NO: 21 | CUR-1575 | mA*mC*mC*A*mU*G*G*mU*G*C*G*C*mG*A*A*A*mU*G*mG*mC*mA |

Figure 7:
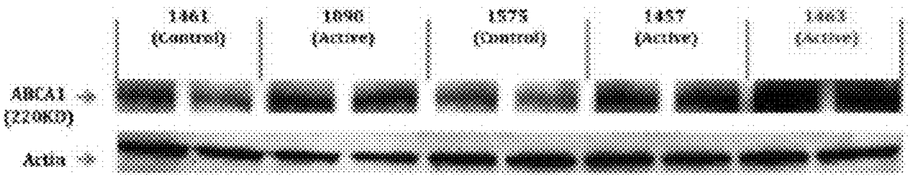
FIG. 7—ABCA1 protein expression in macrophages, at 48 hours following treatment with chemically modified ABCA1-AS antisense oligonucleotides, including an antagoNAT CUR1463.

Example 10: In Vitro Screening of AntagoNAT Targeting ABCA1 Antisense Transcript in Macrophages Treatment of macrophages with both CUR1575 and CUR1463 led to an increase in ABCA1 protein levels relative to the two scrambled sequence control samples (FIG. 7). Importantly, a further increase in ABCA1 protein expression was observed in cells transfected with CUR1463, compared to those treated with the unmodified, active CUR1090, indicating that the 2'-O-methyl antagoNAT modifications of this oligonucleotide increased its efficacy for up-regulating ABCA1 at the protein level. FIG. 7 shows ABCA1 protein expression in macrophages, at 48 hours following treatment with chemically modified ABCA1-AS antisense oligonucleotides.

Example 11: In Vitro Screening of AntagoNAT Targeting ABCA1 Antisense Transcript in Mouse NIH 3T3 Cells Treatment of mouse NIH 3T3 cells with CUR1090, CUR1575 and CUR1463 led to increased ABCA1 mRNA diluted in sterile PBS, and injecting intraperitoneally at a concentration of 5 or 50 mg/kg, in a final volume of 100 cc. Separate groups of mice were treated with either CUR1463 (5 or 50 mg/kg), CUR1575 (5 or 50 mg/kg) or a saline vehicle control twice a week, for four weeks. These mice were then sacrificed 24 hours after the final injection, and various peripheral organs, isolated brain regions, and serum samples were collected.

Analysis of mRNA Expression

Figure 10:
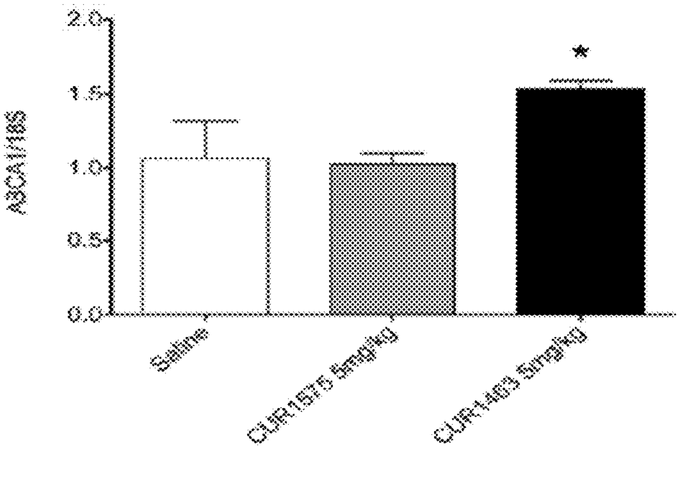
FIG. 10—Expression of ABCA1 mRNA in the livers of wild-type mice treated with ABCA-AS antisense oligonucleotides and antagoNAT (5 mg/kg), twice a week for four weeks. Values represent pooled data obtained over two repeated studies, and are expressed as mean±SEM. * indicates statistically significance differences between CUR1463 and both CUR1575 and saline controls ($p<0.05$; 1-way ANOVA; $4\leq n\leq 9$)
Figure 11:
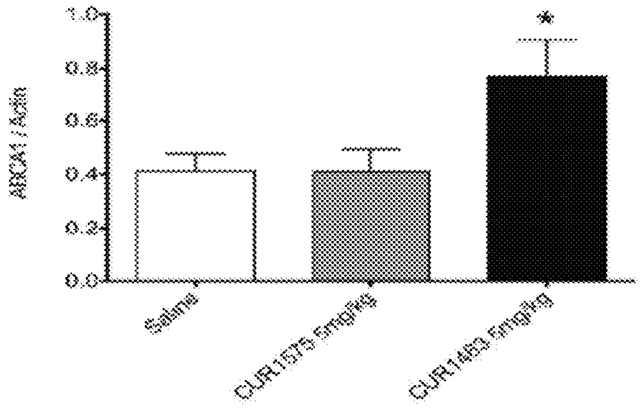
FIG. 11—Expression of ABCA1 protein in the livers of wild-type mice treated with ABCA1-AS antisense oligonucleotides (5 mg/kg), twice a week for four weeks, as assessed by densitometric analysis of the Western immunoblot assay. Values represent pooled data obtained over two repeated studies, and are expressed as mean±SEM.

ABCA1 has been found to play a key role in liver cholesterol homeostasis and studies using transgenic mice have suggested hepatic ABCA1 expression as a major source of HDL cholesterol in plasma. For this reason, ABCA1 mRNA expression was analyzed from liver samples collected from each treatment group. In line with previous in vitro results, treatment of mice with 5 mg/kg of CUR1463 led to a statistically significant increase in liver ABCA1 mRNA expression, compared to treatment with either saline or an equivalent dose of the CUR1575 control (p=0.0075; 1-way ANOVA; $4 \leq n \leq 9$) (FIG. 10). This experiment was repeated, with a separate cohort of animals receiving 5 mg/kg CUR1463 twice a week for four weeks. On both occasions, treatment with CUR1463 led to a statistically significant increase in liver ABCA1 levels, relative to a control. In addition to inducing an increase in mRNA expression, this 5 mg/kg dose of CUR1463 also showed an increase in ABCA1 protein expression within the liver, compared to vehicle or scrambled oligonucleotide controls ($p=0.0459$; 1-way ANOVA; $5 \leq n \leq 6$) (FIG. 11).

Quantification of HDL and LDL Cholesterol

To examine the functional significance of this increase in hepatic ABCA1 expression, total serum cholesterol, LDL cholesterol and HDL cholesterol levels were measured for all three treatment groups. Serum was isolated from blood samples by high-speed centrifugation for 5 minutes. Serum HDL and LDL cholesterol levels were determined using a HDL/LDL Cholesterol Quantification Kit (Biovision). HDL and LDL fractions were separated by adding a 2× Precipitation Buffer, followed by centrifugation. 50 μl of a reaction mixture (containing 44 μl cholesterol assay buffer, 2 μl cholesterol probe, 2 μl enzyme mix and 2 μl cholesterol esterase) was then added to each unknown sample, and all reactions were incubated, in the dark, for 1 hour at 37° C. Optical density was measured at 570 nm in a micro-titer plate reader. Serum HDL and LDL cholesterol levels were determined using a standard curve generated from samples of known cholesterol concentration.

Figure 12A:
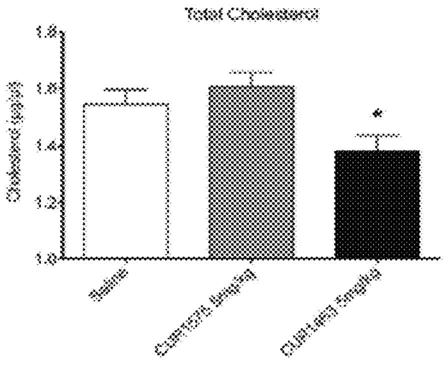
FIG. 12*a*—Total serum cholesterol in mice treated with ABCA1-AS antisense oligonucleotides. Values represent pooled data obtained over two repeated studies, and are expressed as mean±SEM. * indicates statistically significance differences between CUR1463 and both CUR1575 and saline controls ($p<0.05$; 1-way ANOVA; $5 \le n \le 10$).
Figure 12B:
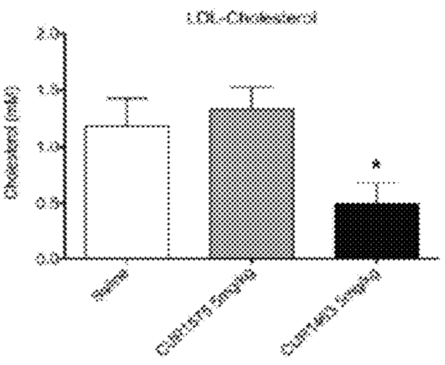
FIG. 12*b*—LDL-cholesterol in mice treated with ABCA1-AS antagoNAT. Values represent pooled data obtained over two repeated studies, and are expressed as mean±SEM. * indicates statistically significance differences between CUR1463 and both CUR1575 and saline controls ($p<0.05$; 1-way ANOVA; $5 \le n \le 10$).
Figure 13:
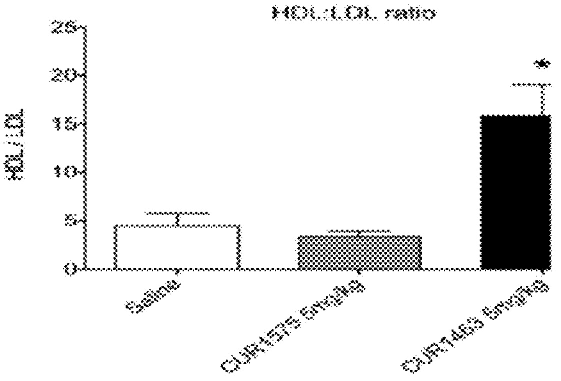
FIG. 13—Ratio of HDL:LDL in mice treated with ABCA1-AS antagoNAT (5 mg/kg), twice a week for four weeks. Values represent pooled data obtained over two repeated studies, and are expressed as mean±SEM. * indicates statistically significance differences between CUR1463 and both CUR1575 and saline controls ($p<0.05$; 1-way ANOVA; $5 \le n \le 10$).

As can be seen in FIGS. 12*a* and 12*b*, mice injected with 5 mg/kg CUR1463 showed not only a statistically significant reduction of total serum cholesterol, compared with either saline or the CUR1575 control ($p=0.0281$; 1-way ANOVA; $n=5$), but also a 50% reduction of serum LDL cholesterol ($p=0.0175$; 1-way ANOVA; $5 \leq n \leq 10$). Furthermore, these mice also showed an increase in the ratio of HDL cholesterol to LDL cholesterol ($p=0.0093$; 1-way ANOVA; $5 \leq n \leq 10$) (FIG. 13).

Quantification of Serum Triglyceride Content

Serum triglyceride levels were monitored using a Triglyceride assay kit (Cayman). This analysis was based on the enzymatic hydrolysis of the triglycerides by lipase to glycerol, the release of which could be measured, in the form of absorbance, by a coupled enzymatic reaction system. First, standards of known triglyceride concentrations were prepared from a provided triglyceride stock. 150 μl of a diluted enzyme buffer solution was added to 10 μl of each standard or unknown sample, followed by incubation for 15 minutes at room temperature. Absorbance was read at 540 nm. Triglyceride concentration (mg/dl) was calculated according to the manufacturer's recommendations.

Figure 14A:
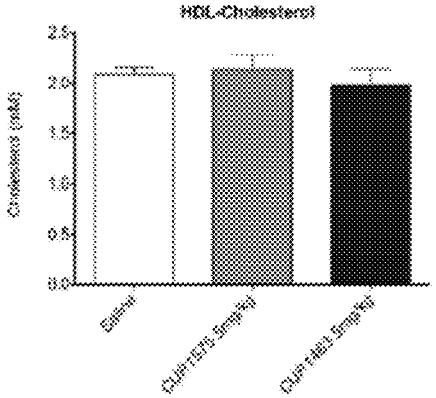
FIG. 14*a*—Serum HDL cholesterol in mice treated with ABCA1-AS antagoNAT (5 mg/kg), twice a week for four weeks. Values represent pooled data obtained over two repeated studies, and are expressed as mean±SEM.
Figure 14B:
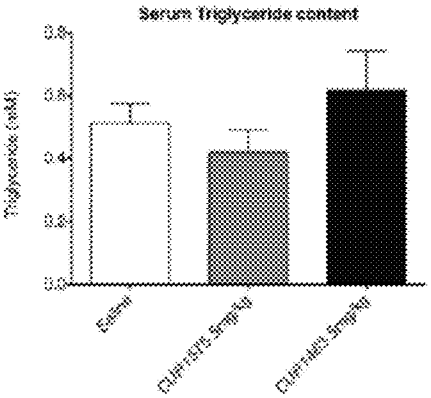
FIG. 14*b*—Triglyceride levels in mice treated with ABCA1-AS antagoNAT (5 mg/kg), twice a week for four weeks. Values represent pooled data obtained over two repeated studies, and are expressed as mean±SEM.

Importantly, treatment with CUR1463, while lowering serum LDL cholesterol, did not decrease atheroprotective HDL levels, nor did it lead to any changes in serum triglyceride content (FIGS. 14*a* and 14*b*).

Measuring Serum Alanine Transaminase (ALT) Activity

ALT activity was determined using the Alanine Transaminase Activity Assay Kit (Cayman). This analysis was achieved by monitoring the rate of NADH oxidation in a coupled reaction system employing lactate dehydrogenase (LDH), which was accompanied by a decrease in absorbance at 340 nm. This decrease was directly proportional to ALT activity. 190 μl of a reaction mixture (containing 150 μl ALT substrate, 20 μl ALT cofactor and 20 μl of either test or positive control samples) was incubated for 15 minutes at 37° C., following which 20 μl of ALT indicator was added. Each reaction was read at 340 nm once every minute for a period of 5 minutes. ALT activity (U/ml) was calculated according to the manufacturer's recommendations.

Figure 15:
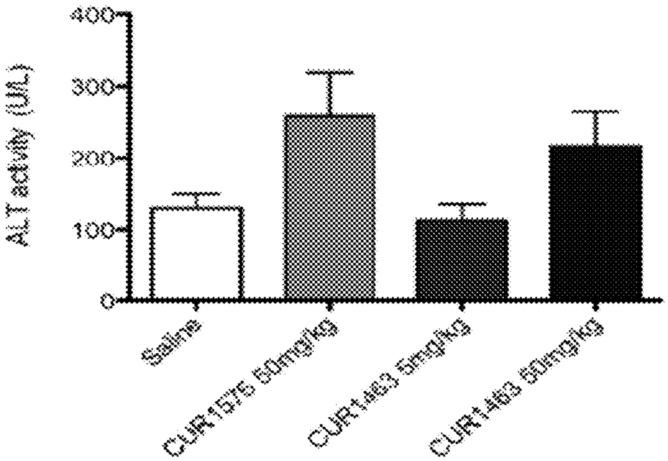
FIG. 15—Serum alanine transaminase (ALT) activity in mice treated with ABCA1-AS antagoNAT (5 mg/kg), twice a week for four weeks. Values represent pooled data obtained over two repeated studies, and are expressed as mean±SEM.

To examine for any potential toxicity of these antisense oligonucleotides, serum alanine transaminase (ALT) activity was also measured for all treatment groups. Serum ALT activity, which is used as a way of screening for liver damage, is represented in FIG. 15. As demonstrated, treatment with the effective dose (5 mg/kg) of CUR1463 led to significantly less ALT activity than the higher, apparently more hepatotoxic dose (50 mg/kg). More importantly, no differences in toxicity were found between the 5 mg/kg effective dose and the saline control, indicating that the effective treatment dose had no adverse liver effects.

Figure 16:
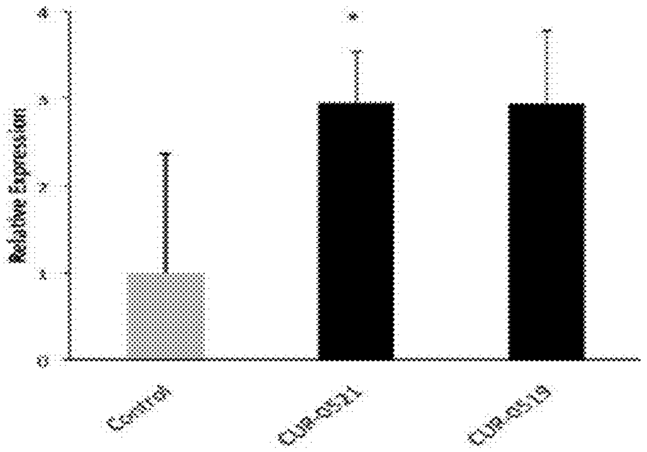
FIG. 16—ABCA1 mRNA expression in human 518A2 melanoma cells 48 hours after treatment with 20 nM siRNA (n=5). Values indicate mean+Std Dev. * indicates statistical significance.

Example 13: In Vitro Screening of Antisense Oligonucleotides Targeting the Human ABCA1 Antisense Transcript A human ABCA1 antisense transcript (AK311445) was identified using the UCSC genome browser. Initially two siRNAs were designed against this transcript to determine if this transcript regulates ABCA1 expression. siRNAs were transfected into human melanoma (518A2) cells at 20 nM. FIG. 16 shows that one of the siRNAs (CUR0521) increased ABCA1 mRNA expression by 3 fold compared to vehicle control ($P=0.05$). The siRNA CUR0519 also increased ABCA1 mRNA expression, but was not statistically significant ($P=0.06$).

Single stranded 2'-O-methyl modified antagoNATs were designed to target the human ABCA1 antisense transcript. The sequence of an antagoNAT and control oligonucleotides are presented in Table 2.

TABLE 2

Sequences of AntagoNAT and Control Oligonucleotides Targeted to ABCA1-AS Antisense Oligonucleotides

| | | |
|---|---|---|
| SEQ ID NO: 22 | CUR-1745 | +T*+C*T*C*T*C*T*G*G*+G*+A*+C |
| SEQ ID NO: 23 | CUR-1746 | +T*+T*A*C*C*T*T*C*A*+T*+A*+C |
| SEQ ID NO: 24 | CUR-1747 | +A*+A*+T*C*A*C*T*T*A*G*C*C*+A*+C*+T |
| SEQ ID NO: 25 | CUR-1716 | mG*mC*mC*T*C*T*T*C*T*A*T*G*G*G*T*C*T*mG*mU*mC |
| SEQ ID NO: 26 | CUR-1719 | mA*mA*mU*C*A*A*mU*G*G*C*mU*G*T*T*mC*T*C*mU*C*U*C*mU*G*G *mG*mA*mC |

Figure 17:
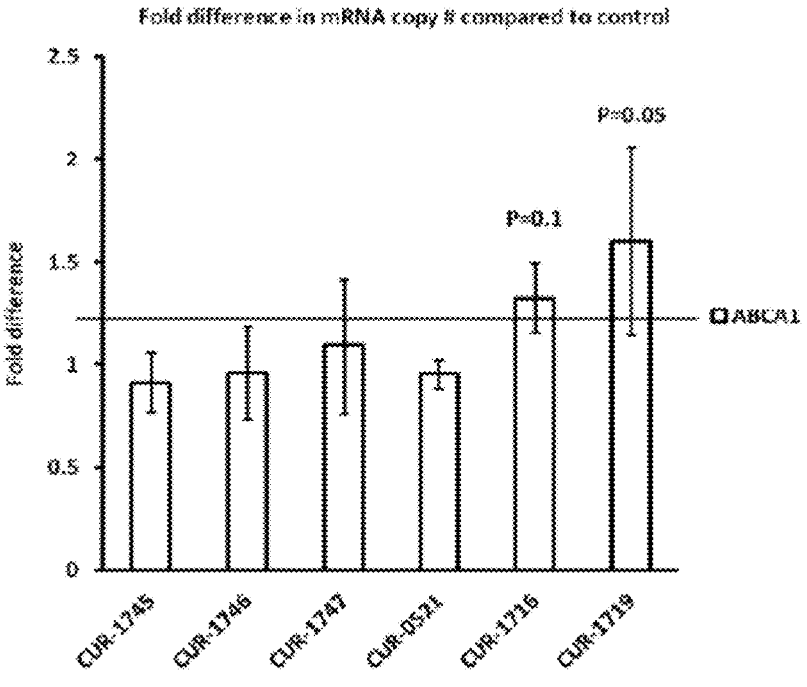
FIG. 17—RT-PCR analysis of ABCA1 mRNA levels in HepG2 cells. ABCA1 mRNA expression is increased with antagoNAT CUR-1719.

FIG. 17 shows that the ABCA1 mRNA expression is increased in human hepatocellular carcinoma (HepG2) cells treated with the antagoNAT CUR1719 compared to vehicle treated cells, as assessed by RT-PCR analysis of ABCA1 mRNA levels. 2'-Bicyclic modified gapmer configuration oligonucleotides (CUR1745 and CUR1747) and 2'-O-methyl gapmer configuration oligonucleotide (CUR1716) did not significantly elevate ABCA1 mRNA expression.

Figure 18:
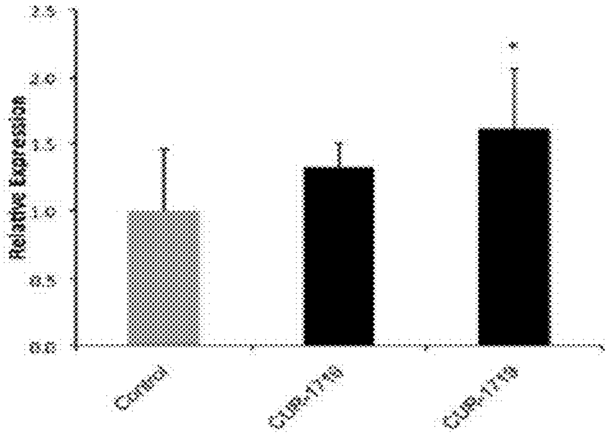
FIG. 18—ABCA1 mRNA expression in human HepG2 hepatocellular carcinoma cells 48 hours after treatment with 2' O-methyl modified antagoNATs. Values indicate mean+Std Dev. * indicates statistical significance.

Human hepatocellular carcinoma (HepG2) cells were treated with the antagoNATs at 20 nM concentration and incubated for 48 hours. FIG. 18 shows that antagoNAT CUR1719 yielded a 1.6-fold increase in ABCA1 mRNA expression compared to vehicle control ($P=0.05$). A second chemically modified oligonucleotide (CUR-1716) also increased ABCA1 expression, but was not statistically significant ($P=0.1$).

Figure 19A:
FIG. 19*a*—Western immunoblot analysis of ABCA1 protein expression in human epithelial colorectal adenocarcinoma (CaCo2) cells 48 hours following treatment of cells with ABCA1-AS antisense oligonucleotides (50 nM, n=3). ABCA1 primary polyclonal antibody (Novus) was used in the assay.
Figure 19B:
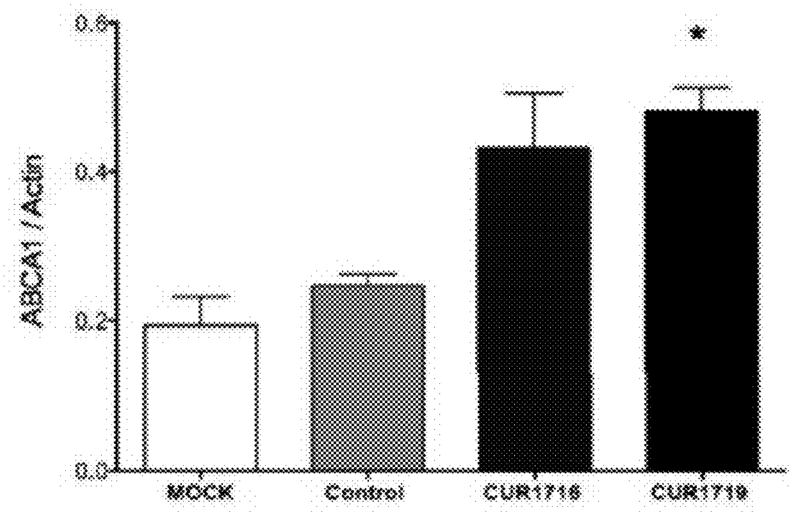
FIG. 19*b*—Densitometric analysis of CaCo2 Western immunoblot assay. Values represent mean±SEM. Data indicates statistical significance with an antagoNAT compared to vehicle treated cells and control oligonucleotide ($p<0.05$; 1-way ANOVA; n=3).

Human epithelial colorectal adenocarcinoma (CaCo2) cells were treated with antagoNATs and incubated for 48 hours. FIGS. 19*a* and 19*b* shows the relative ABCA1 protein expression of these cells, as assessed by Western immunoblot analysis. Cells treated with 50 nM CUR1719 demonstrated a 2.5-fold increase in ABCA1 protein expression in these human cells (p=0.0053; 1-way ANOVA; n=3), compared to vehicle treated cells and treatment with a control oligonucleotide. A similar increase in protein levels was also seen following treatment with CUR1716, but this result failed to reach significance.

Example 14: In Vitro Screening of Antisense Oligonucleotides Targeting the Human SCN1A Antisense Transcript The methods described for the design and analysis of ABCA1 antagoNATs were applied to the design and analysis of antagoNATs targeted to a human SCN1A antisense transcript. A human SCN1A antisense transcript was identified using the UCSC genome browser. Single stranded 2'-O-methyl modified antagoNATs were designed to target the human SCN1A antisense transcript. The sequences of antagoNATs and control oligonucleotides are presented in Table 3.

TABLE 3

Sequences of Chemically Modified Oligonucleotides Targeted to SCN1A-AS Antisense Oligonucleotide

| | | |
|---|---|---|
| SEQ ID NO: 27 | CUR-1763 | +G*+T*G*G*T*A*+T*A*G*G*A*A*+C*+T*+G |
| SEQ ID NO: 28 | CUR-1764 | mG*mU*mG*G*mU*A*mU*A*G*G*A*A*mC*T*G*G*mC*A*mG*mC*mA |
| SEQ ID NO: 29 | CUR-1770 | mG*mC*mC*A*G*T*mC*A*C*A*A*A*mU*T*mC*A*G*A*mU*mC*mA |

Figure 20:
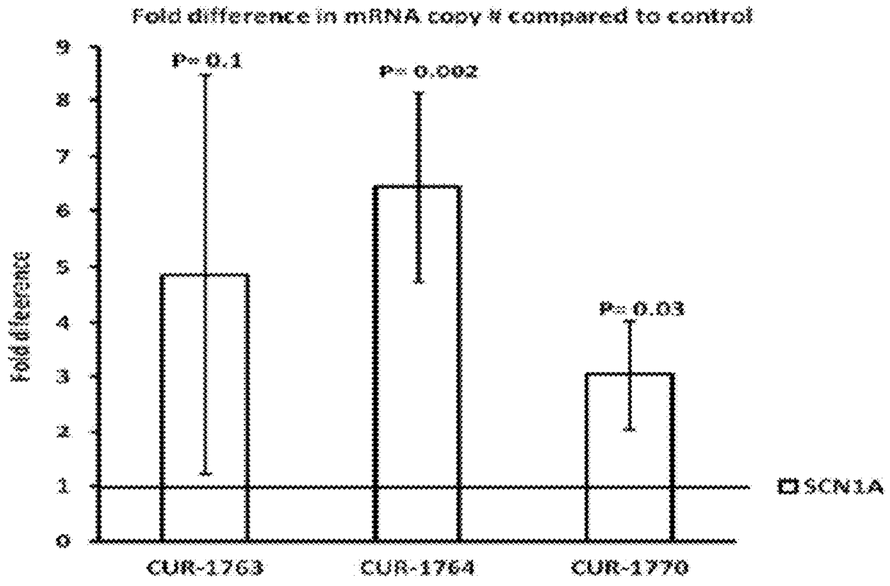
FIG. 20—RT-PCR analysis of SCN1A mRNA levels in HepG2 cells following treatment with an antagoNAT.

Human hepatocellular carcinoma (HepG2) cells were treated with antagoNATs targeted to the human SCN1A antisense transcript and incubated for 48 hours. FIG. 20 shows the relative SCN1A protein expression of these treated cells, as assessed by RT-PCR analysis of SCN1A mRNA levels. SCN1A mRNA expression is increased in HepG2 cells treated with the antagoNAT CUR-1764 compared to vehicle treated cells.

Example 15: In Vitro Screening of Antisense Oligonucleotides Targeting the Human SIRT1 Antisense Transcript The methods described for the design and analysis of ABCA1 antagoNATs were applied to the design and analysis of antagoNATs targeted to a SIRT1 antisense transcript. A SIRT1 antisense transcript was identified using the UCSC genome browser. Single stranded 2'-O-methyl modified antagoNATs were designed to target the SIRT1 antisense transcript. The sequences of antagoNATs and control oligonucleotides are presented in Table 4.

TABLE 4

Sequences of AntagoNAT and Control Oligonucleotides Targeted to SIRT1 Antisense Oligonucleotides

| | | |
|---|---|---|
| SEQ ID NO: 30 | CUR-1099 | +A*+C*C*C*T*C*C*T*T*C*C*T*+C*+C*+C |
| SEQ ID NO: 31 | CUR-1654 | mC*mA*mG*A*A*mU*T*T*mC*A*T*G*mG*mU*mA |
| SEQ ID NO: 32 | CUR-1655 | mA*mC*mA*G*G*mU*G*C*mU*C*A*G*mA*mA*mU |
| SEQ ID NO: 33 | CUR-1656 | mA*mC*mA*G*G*mU*G*C*T*mC*A*G*A*A*mU*T*T*mC*A*mU*G*mG *mU*mA |
| SEQ ID NO: 34 | CUR-1657 | +C*+A*G*A*A*+T*T*T*+C*A*T*G*+G*+T*+A |
| SEQ ID NO: 35 | CUR-1658 | +A*+C*A*G*G*+T*G*C*+T*C*A*G*+A*+A*+T |

Figure 21:
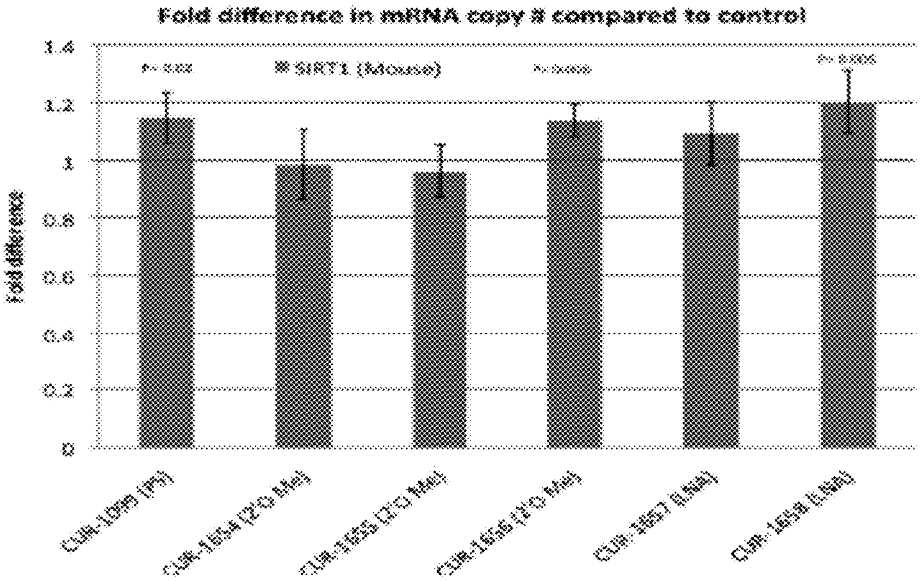
FIG. 21—RT-PCR analysis of SIRT1 mRNA levels in mouse NIH 3T3 cells following treatment with an antagoNAT.

Mouse NIH 3T3 cells were treated with antagoNATs targeted to a SIRT1 antisense transcript and incubated for 48 hours. FIG. 21 shows the relative SIRT1 protein expression of these treated cells, as assessed by RT-PCR analysis of SIRT1 mRNA levels.

Example 16: Upregulation of Mouse Sirt1 mRNA in NIH3T3 Cell Line by Treatment with Antisense Oligonucleotides Targeting Mouse Sirt1-Specific Natural Antisense Transcript In this Example, antisense oligonucleotides of different chemistries targeting mouse Sirt1-specific natural antisense transcript were screened in NIH3T3 cell line at a final concentration of 20 nM. This is a mouse cell cell line. The data below confirms that upregulation of Sirt1 mRNA through modulation of the function of the mouse Sirt1-specific natural antisense transcript.

Materials and Methods

3T3 mouse embryonic fibroblast cells from ATCC (cat# CRL-1658) were grown in Growth Media (Dulbecco's Modified Eagle's Medium (Cellgrow 10-013-CV)+10% Fetal Calf Serum (Cellgrow 35-22-CV)+penicillin/streptomycin (Mediatech cat# MT30-002-CI)) at 37° C. and 5% $CO_2$. The cells were treated with antisense oligonucleotides using the following method. The cells were replated at the density of approximately $10^5$/well into 6 well plates in Growth Media, dosed with 20 nM antisense oligonucleotides and incubated at 37° C. and 5% $CO_2$ overnight. Next day, the media in the 6 well plates was changed to fresh Growth Media (1.5 ml/well). All antisense oligonucleotides were manufactured by IDT Inc. (Coralville, Iowa) or Exiqon (Vedbaek, Denmark). The sequences for all oligonucleotides are listed in Table 5. Stock solutions of oligonucleotides were diluted to the concentration of 20 M in DNAse/RNAse-free sterile water. To dose one well, 2 µl of this solution was incubated with 400 µl of Opti-MEM media (Gibco cat#31985-070) and 4 µl of Lipofectamine 2000 (Invitrogen cat#11668019) at room temperature for 20 min and applied dropwise to one well of a 6 well plate with cells. Similar mixture including 2 µl of water instead of the oligonucleotide solution was used for the mock-transfected controls. Additionally an inactive oligonucleotide CUR-1462 at the same concentration was used as control. After about 18 h of incubation at 37° C. and 5% $CO_2$ the media was changed to fresh Growth Media. Forty eight hours after addition of antisense oligonucleotides the media was removed and RNA was extracted from the cells using SV Total RNA Isolation System from Promega (cat # Z3105) following the manufacturers' instructions. Six hundred nanograms of purified total RNA was added to the reverse transcription reaction performed using SuperScript VILO cDNA Synthesis Kit from Invitrogen (cat#11754-250) as described in the manufacturer's protocol. The cDNA from this reverse transcription reaction was used to monitor gene expression by real time PCR using ABI Taqman Gene Expression Mix (cat#4369510) and primers/probes designed by ABI (assays Mm01168521_ml for mouse Sirt1). The following PCR cycle was used: 50° C. for 2 min, 95° C. for 10 min, 40 cycles of (95° C. for 15 seconds, 60° C. for 1 min) using StepOne Plus Real Time PCR system (Applied Biosystems). The assay for 18S was manufactured by ABI (cat#4319413E). Fold change in gene expression after treatment with antisense oligonucleotides was calculated based on the difference in 18S-normalized dCt values between treated and mock-transfected samples.

TABLE 5

Sequences of AntagoNAT and Control Oligonucleotides Targeted to SIRT1 Antisense Oligonucleotides

| | | |
|---|---|---|
| SEQ ID NO: 30 | CUR-1099 | +A*+C*C*C*T*C*C*T*T*C*C*T*+C*+C*+C |
| SEQ ID NO: 31 | CUR-1654 | mC*mA*mG*A*A*mU*T*T*mC*A*T*G*mG*mU*mA |
| SEQ ID NO: 36 | CUR-1578 | mA*mC*mA*mG*mG*mU*G*C*T*C*A*G*A*A*T*T*T*C*mA*mU*mG*m G*mU*mA |
| SEQ ID NO: 37 | CUR-1748 | +A*+C*A*G*G*T*G*C*T*C*A*G*+A*+A*+T |
| SEQ ID NO: 38 | CUR-1749 | +A*+C*A*G*G*mU*G*C*T*mC*A*G*+A*+A*+T |
| SEQ ID NO: 39 | CUR-1750 | +C*+C*A*C*G*C*G*C*G*A*G*T*+A*+C*+A |

Figure 22:
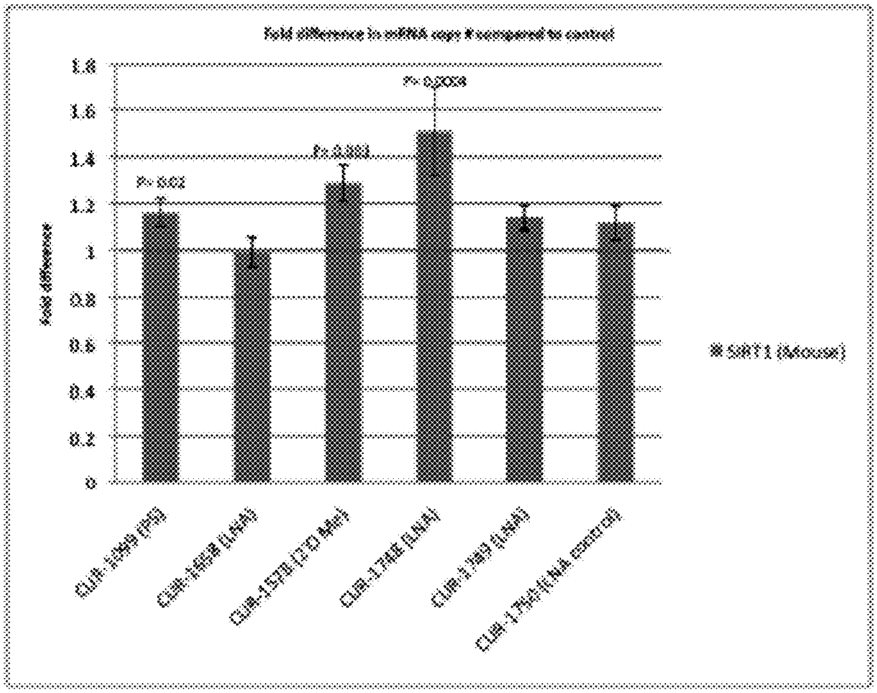
FIG. 22—FIG. 22 shows the mouse Sirt1 mRNA expression is up-regulated in NIH3T3 cells with a phosphothioate oligonucleotide (CUR-1099), 2'Omethyl gapmer/pyrimidine modified oligonucleotide (CUR-1578) and a LNA modified gapmer oligonucleotide (CUR-1748). The control LNA modified gapmer configuration oligonucleotide (CUR-1750) as well as the LNA modified gapmer oligonucleotides (CUR-1658 and CUR-1749) did not significantly up-regulate mouse Sirt1 mRNA expression.

Results:

Mouse Sirt1 mRNA levels in NIH3T3 cells after treatment with 20 nM of antisense oligonucleotides compared to mock-transfected control are shown in FIG. 22. As seen from the data some of the oligonucleotides (CUR-1099, CUR-1578, CUR-1748) when applied at 20 nM were active at upregulating the levels of mouse Sirt1 mRNA. Some of the oligonucleotides (CUR-1658, CUR-1749) designed against the mouse Sirt1 natural antisense sequence did not affect the Sirt1 mRNA levels in NIH3T3 cells. The mouse Sirt1 levels in NIH3T3 cells treated with an oligonucleotide with no homology to the mouse Sirt-1 natural antisense sequence but of similar LNA chemistry (CUR-1750) did not show any significant regulation.

Conclusions:

These differences are in agreement with literature data which indicates that binding of oligonucleotides may depend on the secondary and tertiary structures of the oligonucleotide's target sequence. The result with CUR-1750 confirms that the effects of CUR-1099, CUR-1578, CUR-1748 are specific and do not depend on the non-specific toxicity of these molecules.

What is claimed is:

1. A method of upregulating the expression of a single gene in a cell comprising contacting the cell with an antagoNAT, wherein the antagoNAT is a single stranded oligonucleotide comprising 12-27 nucleoside subunits and which:

is 100% complementary to and specifically hybridizes with a complementary 12-27 nucleotide region of a non-coding natural antisense transcript of the gene; and comprises at least one sugar modified nucleoside subunit at the 3' terminus and at least one sugar modified nucleoside subunit at the 5' terminus; and further comprises internal sugar modified nucleoside subunits and internal sugar unmodified nucleoside subunits between the 5' nucleoside subunit and the 3' nucleoside subunit, and at least one internal nucleoside is modified; and wherein said antagoNAT upregulates the expression of said gene and wherein the antagoNAT comprises a compound of Formula (I), or a salt thereof:

$$C\text{-}A_u\text{-}[B_v\text{-}A'_w]_x\text{-}B_y\text{-}A''_2\text{-}C \qquad \text{Formula (I)}$$

wherein each A, A', and A'' independently has the structure of:

(Ia)

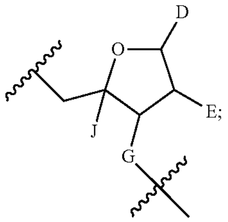

each B independently has the structure of:

(Ib)

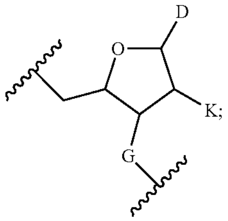

each C is independently hydroxy, phosphate, substituted or unsubstituted alkoxyl, or any suitable 5' or 3' terminus cap;

each u, v, w, x, y and z are independently integers greater than or equal to one;

each D is a heterocyclic base;

each E is independently selected from the group consisting of substituted or unsubstituted alkyl, substituted or unsubstituted alkoxy, substituted or unsubstituted amine, halogen, substituted or unsubstituted aminoalkoxy, substituted or unsubstituted alkenyl, or thiol;

each G is independently —$OP(O)_2O$—, —OP(O)(OR)O—, —OP(O)(S)O—, —OP(O)(SR)O—, —$OP(S)_2O$—, —OP(R)(O)O—, —$OP(NR_2)(O)O$—, —OC(O)O—, —$OCH_2C(O)NHCH_2$—, —$OCH_2S$—, —$CH_2SCH_2$—, —$OP(O)(BH_3)O$—, —$NP(O)_2O$—, —OP(R)(O)O—, or absent when (Ia) is connected to C;

each R is independently hydrogen or substituted or unsubstituted alkyl;

each J is hydrogen or J and E taken together form a ring structure that optionally includes an additional heteroatom selected from N or O; and each K is independently hydroxy or hydrogen and further wherein SEQ ID NOS: 13, 18, 19, 20, 21, 22, 23, 24, 25, 27, 31, 32, 34, 35, 38 and 39 are excluded and wherein the single gene is selected from the group consisting of SCN1A, SIRT1, ABCA1, VEGF, BDNF and GDNF.

2. The method according to claim 1 wherein the sugar modified and sugar unmodified nucleoside subunits each comprise a pyrimidine base or purine base and said modified sugar comprises a locked nucleic acid.

3. The method according to claim 1 wherein the internal sugar modified nucleoside subunits each comprises a pyrimidine base or purine base and wherein said internal modified subunits comprise at least one locked nucleic acid.

4. The method according to claim 1, wherein the sugar modified nucleoside subunits are each substituted at the 2' position with alkoxy, alkyl, halogen, amino, thiol, alkylamine, alkylthiol, alkylester, or O-alkylene bound to the C4' carbon.

5. The method according to claim 1, wherein the sugar modified nucleoside subunits are each substituted at the 2' position with alkoxy, halogen, or O-alkylene bound to the C4' carbon.

6. The method according to claim 1, wherein the sugar modified nucleoside subunits are each substituted at the 2' position with methoxy.

7. The method according to claim 1, wherein the sugar modified nucleoside subunits are each substituted at the 2' position with O-methoxyethyl.

8. The method according to claim 1, wherein the sugar modified nucleoside subunits are each substituted at the 2' position with O-methylene bound to the C4' carbon (2'-$OCH_2$-4') or O-ethylene bound to the C4' carbon (2'-$OCH_2CH_2$-4').

9. The method according to claim 1, wherein the unmodified nucleoside subunit comprises a ribose sugar.

10. The method according to claim 1, wherein the antagoNAT comprises a backbone of phosphodiester, phosphotriester, phosphorothioate, phosphorodithiate, alkylphosphonate, phosphoramidate, boranophosphate, carbonate, carbamate, acetamidate, thioether, thioformacetal internucleotide linkages, or combinations thereof.

11. The method according to claim 1, wherein the antagoNAT comprises a backbone of phosphodiester and phosphorothioate internucleotide linkages.

12. The method according to claim 1, wherein the antagoNAT comprises a backbone of phosphorothioate internucleotide linkages.

13. The method according to claim 1, wherein no more than five internal unmodified nucleosides with 2'-deoxyribose sugar moieties are consecutive, wherein (a) the 3' terminus segment comprises a bicyclic 2'-modified sugar nucleoside and the 5' terminus segment comprises a non-bicyclic 2'-modified sugar nucleoside; or (b) the 3' terminus segment comprises a non-bicyclic 2'-modified sugar nucleoside and the 5' terminus segment comprises a bicyclic 2'-modified sugar nucleoside.

14. The method according to claim 1 wherein the antagoNAT comprises a compound of Formula (I), or a salt thereof:

$$C\text{-}A_u\text{-}[B_v\text{-}A'_w]_x\text{-}B_y\text{-}A''_z\text{-}C \qquad \text{Formula (I)}$$

wherein each A, A', and A" independently has the structure of:

(Ia)

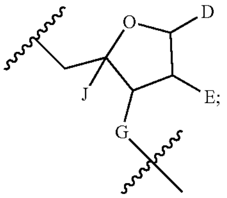

each B independently has the structure of:

(Ib)

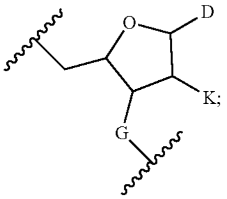

each C is independently hydroxy, phosphate, substituted or unsubstituted alkoxyl, or any suitable 5' or 3' terminus cap;

each u, v, w, x, y and z are independently integers greater than or equal to one;

each D is a heterocyclic base;

each E is independently selected from the group consisting of substituted or unsubstituted alkyl, substituted or unsubstituted alkoxy, substituted or unsubstituted amine, halogen, substituted or unsubstituted aminoalkoxy, substituted or unsubstituted alkenyl, or thiol;

each G is independently —$OP(O)_2O$—, —OP(O)(OR)O—, —OP(O)(S)O—, —OP(O)(SR)O—, —$OP(S)_2O$—, —OP(R)(O)O—, —$OP(NR_2)(O)O$—, —OC(O)O—, —$OCH_2C(O)NHCH_2$—, —$OCH_2S$—, —$CH_2SCH_2$—, —$OP(O)(BH_3)O$—, —$NP(O)_2O$—, —OP(R)(O)O—, or absent when (Ia) is connected to C;

each R is independently hydrogen or substituted or unsubstituted alkyl;

each J is hydrogen or J and E taken together form a ring structure that optionally includes an additional heteroatom selected from N or O; and each K is independently hydroxy or hydrogen and wherein the upregulated targets are selected from the group consisting of SCN1A, BDNF, GDNF, or ABCA1 and further wherein SEQ ID NOS:13, 18, 19, 20, 21, 22, 23, 24, 25, 27, 31, 32, 34, 35, 38 and 39 are excluded.

15. The method according to claim 14 wherein each heterocyclic base is independently selected from a purine or pyrimidine base and wherein a internucleoside linkage is selected from a phosphorthioate.

16. The method according to claim 14 wherein each heterocyclic base is independently selected from adenine, guanine, uracil, thymine, cytosine, 2-aminoadenine, 5-methylcytosine, 5-bromouracil, or hypoxanthine and wherein at least one internucleoside linkage is selected from a phosphorothiate.

17. The method of claim 14, wherein each heterocyclic base is independently selected from adenine, guanine, uracil, thymine, or cytosine.

18. The method of claim 14, wherein the heterocyclic base of each A' is independently selected from uracil, thymine, or cytosine.

19. The method of claim 14, wherein each A, A', or A" independently has the structure of:

(Ic)

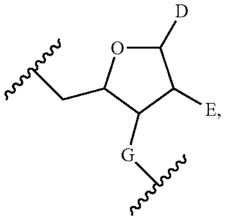

(Id)

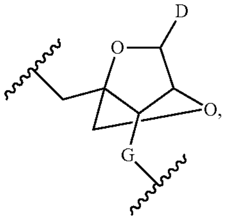

or (Ie)

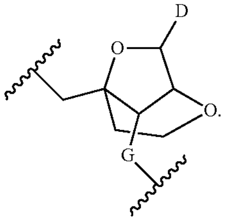

20. The method of claim 14, wherein each E is independently methoxy, ethoxy, O-methylethyl, or fluoro.

21. The method of claim 14, wherein each E is methoxy.

22. The method of claim 14, wherein each E is O-methylethyl.

23. The method of claim 14, wherein each G is independently —$OP(O)_2O$—, —OP(O)(OR)O—, or —OP(O)(S)O—.

24. The method of claim 14, wherein each G is —OP(O)(S)O—.

25. The method of claim 14, wherein each C is hydroxy.

26. The method of claim 14, wherein v and y are independently integers of 1, 2, or 3 when K is hydroxy and x is at least one.

27. The method of claim 14, wherein v and y are independently integers of 1, 2, 3, 4, or 5 when K is hydrogen, and (a) wherein at least one A has the structure of (Id) or (Ie) and at least one A" has the structure of (Ic); or (b) wherein at least one A has the structure of (Ic) and at least one A" has the structure of (Id) or (Ie).

* * * * *